US011932595B2

(12) United States Patent
Uesugi et al.

(10) Patent No.: US 11,932,595 B2
(45) Date of Patent: Mar. 19, 2024

(54) VDR-SILENT VITAMIN D DERIVATIVE AS INHIBITORS OF SREBP AND PHARMACEUTICAL USE THEREOF

(71) Applicants: KYOTO UNIVERSITY, Kyoto (JP); NATIONAL UNIVERSITY CORPORATION TOKYO UNIVERSITY OF AGRICULTURE AND TECHNOLOGY, Fuchu (JP); TEIKYO UNIVERSITY, Tokyo (JP); THE UNIVERSITY OF TOKYO, Tokyo (JP)

(72) Inventors: Motonari Uesugi, Kyoto (JP); Yasushi Takemoto, Kyoto (JP); Kazuo Nagasawa, Tokyo (JP); Atsushi Kittaka, Tokyo (JP); Fumihiro Kawagoe, Tokyo (JP); Hayato Nakagawa, Tokyo (JP)

(73) Assignee: KYOTO UNIVERSITY, NATIONAL UNIVERSITY CORPORATION TOKYO UNIVERSITY OF AGRICULTURE AND TECHNOLOGY, TEIKYO UNIVERSITY and THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 17/478,871

(22) Filed: Sep. 17, 2021

(65) Prior Publication Data

US 2022/0081381 A1 Mar. 17, 2022

Related U.S. Application Data

(60) Provisional application No. 63/080,010, filed on Sep. 17, 2020.

(51) Int. Cl.
| | |
|---|---|
| *C07C 31/137* | (2006.01) |
| *A61P 35/00* | (2006.01) |
| *C07C 215/68* | (2006.01) |
| *C07D 209/48* | (2006.01) |
| *C07D 249/06* | (2006.01) |
| *C07D 257/04* | (2006.01) |
| *C07D 401/04* | (2006.01) |
| *C07D 409/04* | (2006.01) |

(52) U.S. Cl.
CPC ............ *C07C 31/137* (2013.01); *A61P 35/00* (2018.01); *C07C 215/68* (2013.01); *C07D 209/48* (2013.01); *C07D 249/06* (2013.01); *C07D 257/04* (2013.01); *C07D 401/04* (2013.01); *C07D 409/04* (2013.01)

(58) Field of Classification Search
CPC .. C07C 31/137; C07D 249/06; C07D 401/14; C07D 409/04
See application file for complete search history.

(56) References Cited

U.S. PATENT DOCUMENTS

2018/0265463 A1    9/2018  Watanabe et al.

FOREIGN PATENT DOCUMENTS

| JP | 60-64924 A | 4/1985 |
|---|---|---|
| WO | WO 1990/10620 | 9/1990 |

OTHER PUBLICATIONS

Sicinski, et al. Bioorganic & Medicinal Chemistry (1999), 7(12), 2877-2889 (abstract); retrieved from STN; Accession No. 2000: 71439 ZCAPLUS.*
Cancer and Metastasis Reviews (1998), 17(1),91-106.*
Science (1999) , vol. 286 , 531-537.*
Cancer [online], [retrieved on Jul. 6, 2007]. Retrieved from the internet , URL http:/Awww.nlm.nih.gov/medlineplus/cancer.html>.*
Fujishima et al., "Efficient Synthesis and Biological Evaluation of all A-Ring diastereomers of 1α,25-dihydroxyvitamin D3 and its 20-Epimer," Bioorganic & Medicinal Chemistry 2000, 8(1), 123-134.
Kawagoe et al., "Discovery of a Vitamin D Receptor-Silent Vitamin D Derivative That Impairs Sterol Regulatroy Element-Bidning Proetin In Vivo," J. Med Chem. 2021, 64, 9, 5689-5709.
Kawagoe et al., "Design and Synthesis of Fluoro Anologues of Vitamin D," Int. J. Mol. Sci. 2021, 22, 8191, pp. 1-25; https://doi.org/10.3390/ijms22158191.
Marczak et al., "Synthesis and Biological Activity of ther 1,25-Dihydroxyvitamin D3 Diastereomer with Unnatural Configuration at the Rings C/D Side-Chain Moiety," Bioorganic & Medicinal Chemistry Letters 2001, 11(1), 63-66.
Michalak et al., "Total Synthesis of a CD-Ring: Side-Chain Building Block for Preparing 17-epi-Calcitriol Derivatives from the Hajos-Parrish Dione," Journal of Organic Chemistry 2011, 76(16), 6906-6911.
Nagata et al., "Synthetic Chemical Probes That Dossect Vitamin D Activities," ACS Chemical Biology, ACS Chem Biology, 2019, 14, 2851-2858. ACS Chem Biol 2019, 14, 2851-2858.
Oves et al. "Versatile synthesis and biological evaluation of 1,3-diamino-substituted 1α,25-dihydroxyvitamin D3 analogues," Bioorganic & Medicinal Chemistry 2006, 14(4), 928-937.
Ryoden et al. "Endogenous Compounds which Inhibit SREBP Activation," Proceedings of the 133th Annual Meeting of the Pharmaceutical Society of Japan 2013, 133th, 29K-pm09S. (See ISR and IPRP).
Shimazaki et al. "Analogs of 1α, 25-dihydroxyvitamin D3 with high potency in induction of osteoclastogenesis and prevention of dendritic cell differentiation: Synthesis and biological evaluation of 2-substituted 19-norvitamin D analogs," Bioorganic & Medicinal Chemistry 2006, 14(13), 4645-4656.

(Continued)

*Primary Examiner* — Shawquia Jackson
(74) *Attorney, Agent, or Firm* — SQUIRE PATTON BOGGS (US)

(57) ABSTRACT

Provided are vitamin $D_3$ derivatives of formula (I), pharmaceutical compositions thereof, and pharmaceutical or medical uses thereof for treating metabolic disease, a liver disease, obesity, diabetes, cardiovascular disease, or cancer in a patient in need thereof.

21 Claims, 7 Drawing Sheets

(56) References Cited

OTHER PUBLICATIONS

Suhara et al. "Design and Efficient Synthesis of New Stable 1α,25-Dihydroxy-19-norvitamin D3 Analogues Containing Amide Bond", Bioorganic & Medicinal Chemistry Letters (2002), 12(24), 3533-3536.
Suhara et al., "Synthesis of Novel 1, 25-Dihydroxy-19-Norvitamin $D_3$ with an Amide Conjugate", Heterocycles (2004), 62, 423-436.
Wang et al., "Vitamin D receptor agonist doxercalciferol modulates dietary fat-induced renal disease and renal lipid metabolism", American J. of Physiology Renal Physiology 2011, 300, F801-810.
International Search Report and Written Opinion for PCT International Application No. PCT/US2021/05100, dated Dec. 9, 2021, 17 pages.
Fujii et al., "Structural development of p-carborane-based potent non-secosteroidal vitamin D analogs," Bioorganic.vol. 22, No. 21, Nov. 1, 2014 (Nov. 1, 2014), pp. 5891 5901, XP055867089,Amsterdam, NLISSN: 0968-0896, DOI: 10.1016/j.bmc. 2014.09.020.
Sicinski et al., "Synthesis and biological activity of 22-iodo and (E)-20(22)-dehydro analogues of 1 [alpha],25-dihydroxyvitamin D3," Bioorganic, Elsevier, Amsterdam, NL, vol. 7, No. 12, Jun. 5, 2017 (Jun. 5, 2017), pp. 2877-2889, XP085050448JSSN: 0968-0896, DOI: 10.1016/S0968-0896(99)00249-7.

\* cited by examiner

VDR-SILENT VITAMIN D DERIVATIVE AS INHIBITORS OF SREBP AND PHARMACEUTICAL USE THEREOF

CROSS-REFERENCES TO RELATED APPLICATIONS

This application is a U.S. Non-Provisional application, claiming the benefit of U.S. Provisional Application No. 63/080,010, filed on Sep. 17, 2020, the entire contents of which are herein incorporated by reference.

FIELD OF DISCLOSURE

Provided are novel vitamin $D_3$ derivatives and pharmaceutical or medical use thereof for treating a disease selected from metabolic disease, a liver disease, diabetes, cancer, obesity and cardiovascular disease in a subject in need thereof.

BACKGROUND

The fundamental actions of vitamin $D_3$ and its metabolites are to maintain calcium and phosphorous homeostasis in animals. The activity is achieved by the direct binding of $1\alpha,25$-dihydroxyvitamin $D_3$ [$1\alpha,25(OH)_2D_3$], a hydroxylated metabolite of vitamin $D_3$, to the vitamin D receptor (VDR). (Kato, S. *J. Biochem.* 2000, 127, 717-722; Jurutka, P. W.; Whitfield, G. K. et al. *Rev. Endocr. Metab. Disord.* 2001, 2, 203-216). VDR is a vitamin D-specific member of the nuclear receptor family of transcription factors that controls expression of a myriad of genes involved in calcium/phosphorous homeostasis (Veldurthy, V. et al. *Bone Res.* 2016, 4, #16041), cell differentiation and growth (Samuel, S. et al. *Nutrition Rev.* 2008, 66, S116-S124), and immune responses (White, J. H. *Rev. Endocr. Metab. Disord.* 2012, 13, 21-29; Cantorna, M. T. et al. *Am. J. Clin. Nutr.* 2004, 80, 1717S-1720S; Aranow, C. *J. Invest. Med.* 2011, 59, 881-886). The biological importance of VDR and the existence of $1\alpha,25(OH)_2D_3$ as a potent lead agonist has rendered VDR an attractive target for pharmaceutical development. Several thousands of vitamin D analogues have chemically been synthesized, and eight synthetic VDR ligands have achieved clinical uses: for example, calcipotriol for psoriasis (Calverley, M. *J. Tetrahedron*, 1987, 43, 4609-4619), for secondary hyperparathyroidism paricalcitol (Slatopolsky, E. et al. *Am. J. Kidney Dis.* 1995, 26, 852-860), and eldecalcitol for osteoporosis (Kubodera, N. *Curr. Bioactive Compds.* 2006, 2, 301-315).

The majority of the synthetic vitamin D analogues contain modified side chains on the CD ring or substitutions of the functional groups on the A-ring, as indicated below:

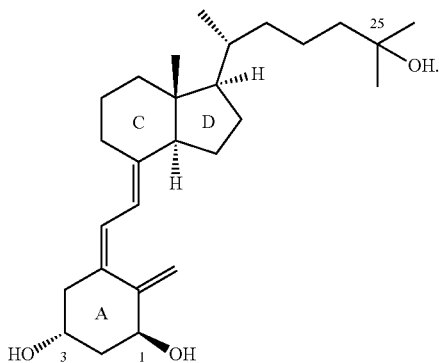

However, these analogues usually maintain three the hydroxy groups or their equivalents at C1, C3, and C25 positions that are required for the interaction with VDR (Rochel, N. et al. *Mol. Cell* 2000, 5, 173-179). Recently, introduction of a large substituent at the CD-ring side chain afforded a VDR-antagonist or partial agonist that lacked calcemic action (Nakabayashi, M. et al. *J. Med. Chem.* 2008, 51, 5320-5329; Kudo, T. et al. *J. Med. Chem.* 2014, 57, 4073-4087; Anami, Y. et al. *J. Med. Chem.* 2014, 57, 4351-4367). (For VDR-antagonists with a large substituent on the lactam side-chain DLAMs, see Nakano, Y. et al. *J. Med. Chem.* 2006, 49, 2398-2406. For antagonists with a long alkyl side-chain ZK-159222, see Herdick, M. et al. *J. Biol. Chem.* 2000, 275, 16506-16512. For antagonists with a small α,β-unsaturated lactone ring on the side-chain of TEI-9647 analogues, see Saito, N. et al. *J. Med. Chem.* 2006, 49, 7063-7075.) Also, truncation of the side chain of vitamin $D_3$ led to the discovery of an in vivo active VDR ligand that lacked calcemic action (Plum, L. A. et al. *Proc. Natl. Acad. Sci. U S A.* 2004, 101, 6900-6904). However, the synthetic efforts of vitamin D analogues has long been centered on VDR as a pharmacological target.

Another genomic target of vitamin $D_3$ has recently emerged. The inventors previously reported that 25-hydroxyvitamin $D_3$ [$25(OH)D_3$, 1, FIG. 1], a major circulating form of vitamin $D_3$, inhibits the activation of sterol regulatory element-binding proteins (SREBPs), a family of master transcription factors for lipogenesis, by interacting with SCAP, a specific escort protein for SREBP (Brown, M. S.; Goldstein, J. L. *Cell* 1997, 89, 331-340; Goldstein, J. L. et al. *Cell* 2006, 124, 35-46). SREBPs are involved in lipid homeostasis and control of lipid metabolism in all tissues, by regulating expression of the genes related to biosynthesis and uptake of fatty acids, triglycerides, cholesterol, and phospholipids. The association of $25(OH)D_3$ with SCAP induces degradation of both SCAP and SREBP to block the expression of SREBP-controlled lipogenic genes (Asano, L. et al. *Cell Chem. Biol.* 2017, 24, 207-217).[21] A low µM dose of $25(OH)D_3$ inhibits cellular lipogenesis by limiting the expression of SREBP-responsive genes in cultured cells, suggesting that $25(OH)D_3$ serves as a starting point of designing SREBP inhibitors.

Because of their central roles in lipid metabolism, SREBPs are strongly linked to metabolic syndromes. For example, high insulin levels, induced by high calorie diets or obesity, hyper-activate SREBPs, causing triglyceride accumulation and inducing fatty liver diseases. Hyper-activation of SREBPs also increases cholesterol levels and suppresses insulin receptor substrate-2, leading to hyperlipidemia, arteriosclerosis, and insulin resistance. Furthermore, activation of SREBPs is often correlated with the growth of cancers and the ability of hepatitis virus to cause fatty liver diseases (J. A. Menendez and R. Lupu, *Nat. Rev. Cancer*, 2007, 7, 763-777; A. J. Brown, *Biochem. 1*, 2008, 416, e15-e17). SREBP1 hyperactivation also contributes to other metabolic diseases and conditions, such as obesity, diabetes mellitus, dyslipidemia, hepatosteatosis, atherosclerosis, and inflammation and fibrosis in various organs (Shimano, H. et al. 2017). The involvement of SREBP activation in multiple diseases has made these transcription factors attractive pharmaceutical targets. To date, the only known "endogenous" molecules that directly inhibit the SREBP activation pathway are sterols.

Although no small-molecule inhibitors of SREBP/SCAP have been approved for clinical uses, SREBP has now highly been regarded as a promising drug target for fatty liver diseases (Shimano, H.; Sato, R. *Nature Rev. Endocri-* nol. 2017, 13, 710-730) and cancers (DeBose-Boyd, R. A.; Ye, J. *Trends Biochem. Sci.* 2018, 43, 358-368; Röhrig, F.; Schulze, A. *Nature Rev. Cancer* 2016, 16, 732-749; Chen, M. et al. An aberrant SREBP-dependent lipogenic program promotes metastatic prostate cancer. *Nature Genet.* 2018, 50, 206-218; Liu, M. et al. Transcriptional profiling reveals a common metabolic program in high-risk human neuroblastoma and mouse neuroblastoma sphere-forming cells. *Cell Reports* 2016, 17, 609-623), which are characterized as having abnormal or increased lipid metabolism (Baenke, F. et al. 2013, 6, 1353-1363; Guo, D. et al. *Curr. Pharm. Des.* 2014, 20, 2619-2626; Wen, Y-A. et al. *Cell Death & Disease* 2018, 9, #265; Cheng, X. et al. *Curr. Top. Med. Chem.* 2018, 18, 484-493; Yin, F. et al. *Cell Death & Disease* 2019, 10, #672; Freed-Pastor, W. A. et al. *Cell* 2012, 148, 244-258.). It has also been described that SREBP has a role in several disease-linked physiological processes not directly related with lipid homeostasis, including innate immunity (Im, S-S. *Cell Metab.* 2011, 13, 540-549) and virus infection (Yuan, S. *Nature Commun.* 2019, 10, 120). One prominent class of synthetic SREBP inhibitors includes fatostatin and its drug-like derivative FGH10019 (Kamisuki, S. *Chem. Biol.* 2009, 16, 882-892; Kamisuki, S. I *Med. Chem.* 2011, 54, 4923-4927), which have extensively been used as pharmacological tools for interrogating the roles of SREBP/SCAP in disease conditions (Kusnadi, A. et al. *Immunity* 2019, 51, 241-257; Guo, C. et al. *Immunity* 2018, 49, 842-856; Bertolio, R. et al. *Nature Commun.* 2019, 10, 1326; Syafruddin, S. E. et al. *Nature Commun.* 2019, 10, 1152; Talebi, A. et al. *Nature Commun.* 2018, 9, 2500; Nguyen, Van T. M. et al. *Nature Commun.* 2015, 6, 10044; van der Kant, R. et al. *Cell Stem Cell* 2019, 24, 363-375; Chen, M. et al. *Nature Genet.* 2018, 50, 206-218; Liu, M. et al. *Cell Reports* 2016, 17, 609-623). None of these experimental SREBP inhibitors have yet reached clinical approval.

Toward the goal of providing SREBP inhibitors which have little or no VDR activity, the synthesis and biological evaluation of vitamin $D_3$ analogues, in which the C1 and/or C3 position(s) of the A-ring were substituted, have previously been reported (WO2016/103722). Among them, compound 3

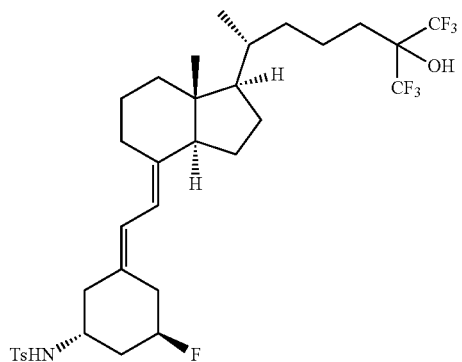

selectively impaired SREBP/SCAP without eliciting VDR activity in cultured cells (Nagata, A. *ACS Chem. Biol.* 2019, 14, 2851-2858). However, the utility of compound 3 in vivo was limited due to its residual calcemic activity at high doses and its low bioavailability.

What is needed are new, structurally-distinct chemical scaffolds with potentially different pharmacological properties to meet the specific requirements of target disease conditions.

SUMMARY

It is the object of this disclosure to provide synthetic vitamin D analogues which are SREBP inhibitors which may have very weak or negligible VDR activity and/or improved drug-like properties, The compounds disclosed herein, in which the structure of the A-ring of $25(OH)D_3$ is completely replaced, are inhibitors of SREBP(s). Certain compounds also have very weak or negligible VDR activity. It is also the object of this disclosure that the compounds provided are useful for treating a disease such as metabolic disease including non-alcoholic steatohepatitis (NASH); a liver disease including fatty liver disease; diabetes; cancer; obesity; cardiovascular disease; and the like.

In one aspect, provided is a compound of the following general formula (I):

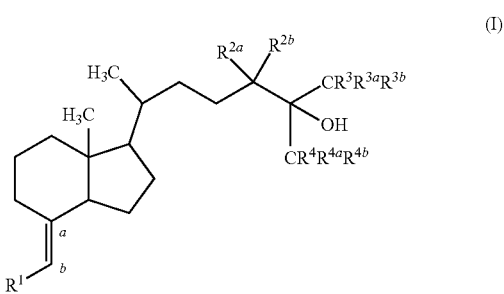

(I)

or a stereoisomer, mixture of stereoisomers, and/or a pharmaceutically acceptable salt thereof, wherein the double bond from a to b is in the E-configuration or Z-configuration;

$R^1$ is hydrogen;

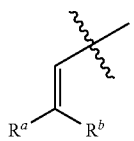

where $R^a$ and $R^b$ together with the carbon to which they are attached form an unsubstituted $C_5$-$C_7$-cycloalkyl group; —$CH_2$—S-(heteroaryl); —$CH_2$-(1,3-dioxo-isoindolin-2-yl);

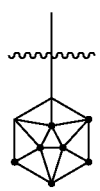

(ortho-carboranyl); —$CH_2$—NH-(phenyl); or

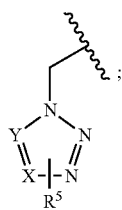

$R^{2a}$, $R^{2b}$, $R^3$, $R^{3a}$, $R^{3b}$, $R^4$, $R^{4a}$, and $R^{4b}$ are independently selected from hydrogen and halo;

one of X and Y is $CR^5$ and the other is CH; or one of X and Y is $CR^5$ and the other is N;

$R^5$ is hydrogen; $C_1$-$C_6$-alkyl; hydroxy-$C_1$-$C_6$-alkyl; aryl optionally substituted with 1, 2, or 3 $R^{5a}$ groups; or 5- or 6-membered heteroaryl optionally substituted with 1, 2, or 3 $R^{5a}$ groups;

each $R^{5a}$ is independently hydrogen, alkyl, haloalkyl, or halo; and wherein each phenyl and heteroaryl group are independently optionally substituted with 1, 2, 3, 4, or 5 groups independently selected from the group consisting of halogen, halo-$C_{1-4}$ alkyl, —S-(halo-$C_{1-4}$ alkyl), $C_{1-4}$ alkoxy, halo-$C_{1-4}$ alkoxy, nitro, cyano, and $C_{1-4}$ alkoxycarbonyl; and provided that the compound is not

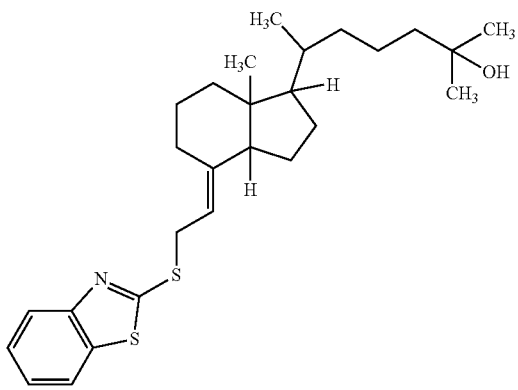 [SMILES: CC(CCCC(C)(C)O)C1CCC2/C(=C/CSc3nc4ccccc4s3)CCCC21C]

or a stereoisomer, mixture of stereoisomers, and/or a pharmaceutically acceptable salt thereof.

In still another aspect, provided is a pharmaceutical composition, comprising as the active ingredient the compound of Formula (I) or a pharmaceutically acceptable salt thereof and a pharmaceutically acceptable carrier.

In another aspect, provided is a method for treating a disease selected from metabolic disease including non-alcoholic steatohepatitis; a liver disease including fatty liver disease; obesity; diabetes; cardiovascular disease; hyperlipidemia (including hypertriglyceridemia and hypercholesterolemia); or cancer (including prostate cancer, liver cancer, bile duct cancer, bone cancer, breast cancer, colon cancer, colorectal cancer, endometrial cancer, esophageal cancer, hematological cancer (including a lymphoma and a leukemia), kidney cancer, lung cancer, ovarian cancer, pancreatic cancer, head and neck squamous cell carcinoma, squamous cell skin cancer, skin melanoma, and uveal melanoma) in a subject, comprising the step of administering to the subject in need thereof a therapeutically effective amount of the compound of Formula (I) or a pharmaceutically acceptable salt thereof or administering to the subject in need thereof a therapeutically effective amount of a pharmaceutical composition, comprising as the active ingredient the compound of Formula (I) or a pharmaceutically acceptable salt thereof, and a pharmaceutically acceptable carrier.

In another aspect, provided is a method for inhibiting SREBPs in a subject, comprising the step of administering to the subject in need thereof a therapeutically effective amount of the compound of Formula (I) or a pharmaceutically acceptable salt thereof or administering to the subject in need thereof a therapeutically effective amount of a pharmaceutical composition, comprising as the active ingredient the compound of Formula (I) or a pharmaceutically acceptable salt thereof, and a pharmaceutically acceptable carrier.

In still another aspect, provided is a use of the compound of Formula (I) or a pharmaceutically acceptable salt thereof in the manufacture of a medicament for the treatment of metabolic disease including non-alcoholic steatohepatitis; a liver disease including fatty liver disease; diabetes; hyperlipidemia (including hypertriglyceridemia and hypercholesterolemia); cancer (including prostate cancer, liver cancer, bile duct cancer, bone cancer, breast cancer, colon cancer, colorectal cancer, endometrial cancer, esophageal cancer, hematological cancer (including a lymphoma and a leukemia), kidney cancer, lung cancer, ovarian cancer, pancreatic cancer, head and neck squamous cell carcinoma, squamous cell skin cancer, skin melanoma, and uveal melanoma); obesity; or cardiovascular disease.

In still another aspect, provided is the compound of Formula (I) or a pharmaceutically acceptable salt thereof for use in the treatment of metabolic disease including non-alcoholic steatohepatitis; a liver disease including fatty liver disease; diabetes; hyperlipidemia (including hypertriglyceridemia and hypercholesterolemia); cancer (including prostate cancer, liver cancer, bile duct cancer, bone cancer, breast cancer, colon cancer, colorectal cancer, endometrial cancer, esophageal cancer, hematological cancer (including a lymphoma and a leukemia), kidney cancer, lung cancer, ovarian cancer, pancreatic cancer, head and neck squamous cell carcinoma, squamous cell skin cancer, skin melanoma, and uveal melanoma); obesity; hyperlipidemia (including hypertriglyceridemia and hypercholesterolemia); or cardiovascular disease.

In still another aspect, provided is a compound of the following formula:

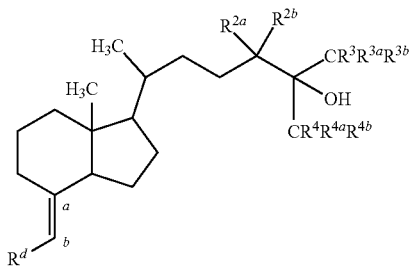

where
$R^{2a}$, $R^{2b}$, $R^3$, $R^{3a}$, $R^{3b}$, $R^4$, $R^{4a}$, and $R^{4b}$ are independently selected from hydrogen and halo; and
$R^d$ is

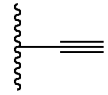

or —$N_3$.

In still another aspect, provided is a method for preparing the compound of Formula (I) or a pharmaceutically acceptable salt thereof, wherein R¹ is

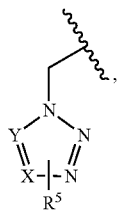

comprising
a) treating a compound of the following formula:

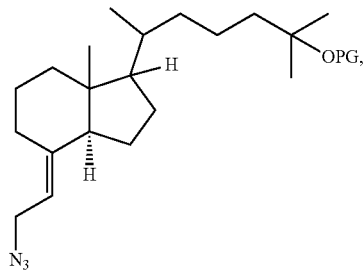

or a stereoisomer or mixture of stereoisomers thereof, where PG is a protecting group, with

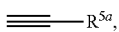

and removing the protecting group;
b) optionally purifying or isolating the Compound of Formula I.

DETAILED DESCRIPTION

Definitions

Figure 1:
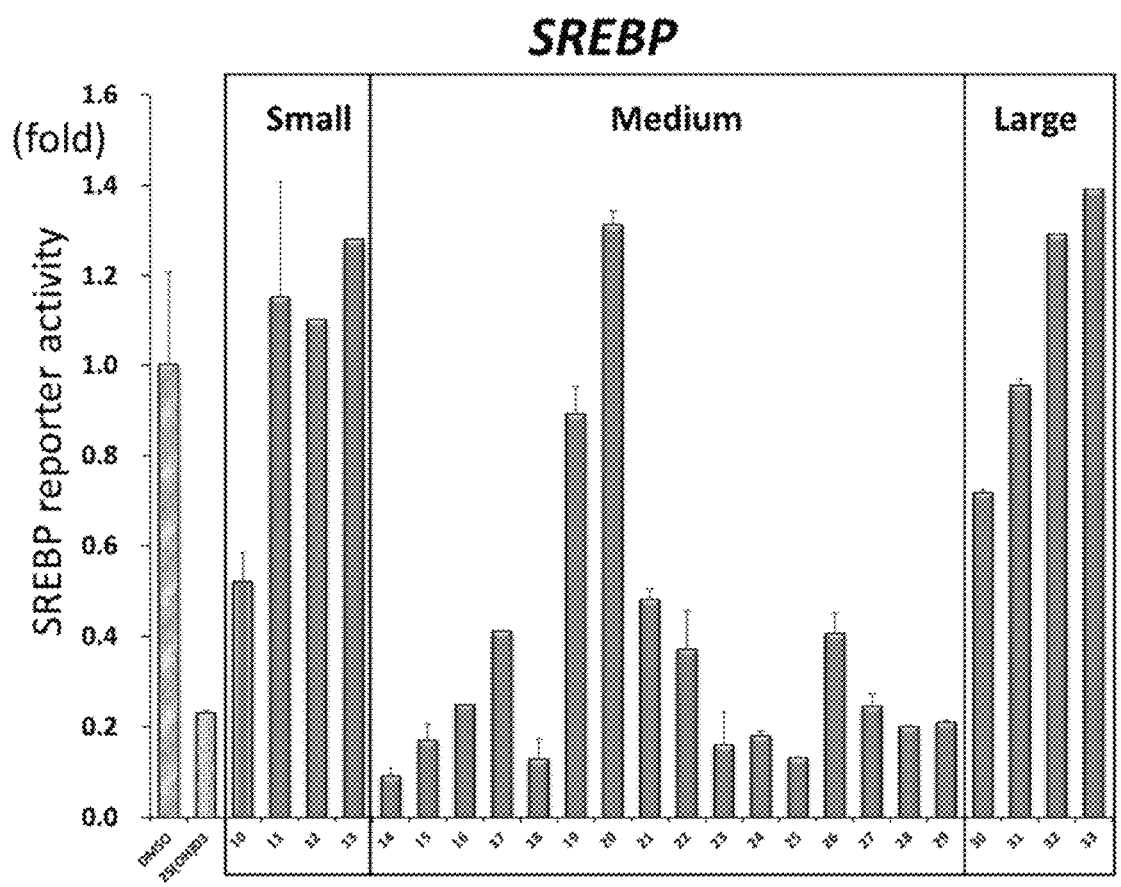
FIG. 1 shows the effects of Compounds 10-33 on SREBP activation.

The term "C$_{1-4}$ alkoxy" used herein refers to an —OR group where R is C$_{1-4}$ alkyl, as defined herein.

The term "alkyl" used herein refers to a straight- or branched-chain hydrocarbon group in some embodiments, having 1 to 12 carbon atoms, in some embodiments, having 1 to 6 carbon atoms, and in some embodiments, having 1 to 4 carbon atoms. In some embodiments, alkyl is methyl, ethyl, n-propyl, isopropyl, n-butyl, isobutyl, or tert-butyl.

The term "cycloalkyl" used herein refers to a saturated aliphatic monocyclic hydrocarbon ring having 3 to 10 carbon atoms, in some embodiments, having 5 to 7 carbon atoms, and in some embodiments, having 3 to 6 carbon atoms. In some embodiments, the cycloalkyl group is cyclopropyl, cyclobutyl, cyclopentyl, or cyclohexyl.

The term "aryl" used herein refers to a monovalent group of monocyclic aromatic hydrocarbon ring or bicyclic aromatic hydrocarbon ring having 6 to 10 carbon atoms. In some embodiments, the aryl group is phenyl.

The term "halogen" or "halo" used herein refers to fluorine atom, chlorine atom, bromine atom, iodine atom, etc.

The term "halo-C$_{1-4}$ alkyl" used herein refers a C$_{1-4}$ alkyl group substituted with at least one (in some embodiments, 1-5, 1-4, 1-3, 1-2, 1, 2, 3, 4, or 5) halo which are independently selected.

The term "halo-C$_{1-4}$ alkoxy" used herein refers to an —OR group where R is halo-C$_{1-4}$ alkyl, as defined herein.

The term "C$_{1-4}$ alkoxycarbonyl" used herein refers to a —C(O)R group, where R is C$_{1-4}$ alkoxy as defined herein.

The term "heteroaryl" used herein refers to a monocyclic or bicyclic, monovalent aromatic cyclic group having 5 to 10 ring atoms where at least one (in some embodiments 1, 2 3, or 4) atom is a heteroatom independently selected from nitrogen, oxygen and sulfur and where the remaining atoms are carbon atoms. In some embodiments, heteroaryl is a 5 to 6-membered heteroaryl group. In some embodiments, the heteroaryl is pyrrolyl, furanyl, thienyl, isoxazolyl, isothiazolyl, pyrazolyl, oxazolyl, thiazolyl, imidazolyl, pyridyl, pyrimidinyl, indolyl, isoindolyl, benzothiazolyl, benzoxazolyl, quinolinyl, isoquinolinyl, pyrazinyl, pyridazinyl, triazolyl, tetrazolyl. In some embodiments, heteroaryl is thienyl or pyridyl.

The term "hydroxy-$C_1$-$C_6$-alkyl" used herein refers to a $C_1$-$C_6$-alkyl group, as defined herein, substituted with 1, 2, or 3 hydroxy groups (in some embodiments, one hydroxy). In some embodiments, hydroxy-$C_1$-$C_6$-alkyl is 3-hydroxy-propyl, 4-hydroxy-butyl, 5-hydroxy-pentyl.

The optionally substituted aryl and optionally substituted heteroaryl refer to the above mentioned aryl and heteroaryl which may be optionally substituted with the same or different at least one group (in some embodiments, 1-4 groups 1-3 groups, 1-2 groups, 4 groups, 3 groups, 2 groups, or 1 group) selected from the group consisting of halogen, halo-$C_{1-4}$ alkyl, —S-(halo-$C_{1-4}$ alkyl), $C_{1-4}$ alkoxy, halo-$C_{1-4}$ alkoxy, nitro, cyano, $C_{1-4}$ alkoxycarbonyl, and $C_6$-10 aryl (where the aryl is not further substituted). In some embodiments, the optionally substituted aryl and optionally substituted aryl are aryl and heteroaryl substituted with the same or different 1 to 4 group(s) independently selected from the group consisting of chloro, fluoro, bromo, methyl, methoxy, trifluoromethyl, methoxycarbonyl, trifluoromethoxy, nitro, cyano, —S—CF3, and phenyl.

All of the embodiments disclosed herein include any stereoisomer or mixture of stereoisomers and/or pharmaceutically acceptable salts thereof, unless otherwise specifically indicated.

The compounds of Formula (I) may have asymmetric centers. Compounds of Formula (I) containing an asymmetrically substituted atom may be isolated in optically active or racemic forms. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. All chiral, diastereomeric, all mixtures of chiral or diastereomeric forms, and racemic forms are within the scope of this disclosure, unless the specific stereochemistry or isomeric form is specifically indicated. It will also be understood by a person of ordinary skill in the art that when a compound is denoted as (R) stereoisomer, it may contain the corresponding (S) stereoisomer as an impurity and vice versa.

Certain compounds of Formula (I) can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth.

Provided are the following embodiments.

Embodiment 1: Provided is a compound of formula (I) as described in the Summary.

Embodiment 1A: Provided is a compound of formula (I-P)

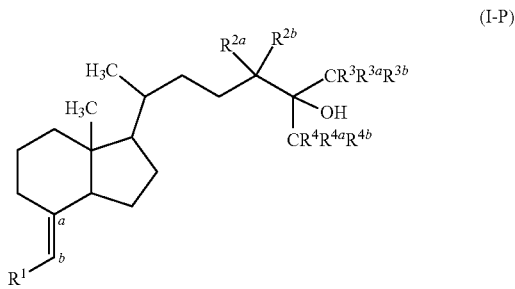

(I-P)

or a stereoisomer, mixture of stereoisomers, and/or a pharmaceutically acceptable salt thereof, wherein the double bond from a to b is in the E-configuration or Z-configuration;

$R^1$ is hydrogen;

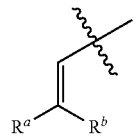

where $R^a$ and $R^b$ together with the carbon to which they are attached form an unsubstituted $C_5$-$C_7$-cycloalkyl group; —$CH_2$—S-(heteroaryl); —$CH_2$-(1,3-dioxo-isoindolin-2-yl);

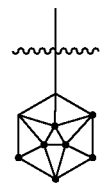

(ortho-carboranyl); —$CH_2$—NH-(phenyl); or

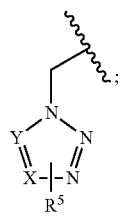

$R^{2a}$, $R^{2b}$, $R^3$, $R^{3a}$, $R^{3b}$, $R^4$, $R^{4a}$, and $R^{4b}$ are independently selected from hydrogen and halo; one of X and Y is $CR^5$ and the other is CH; or one of X and Y is $CR^5$ and the other is N;

$R^5$ is hydrogen; $C_1$-$C_6$-alkyl; hydroxy-$C_1$-$C_6$-alkyl; aryl optionally substituted with 1, 2, or 3 $R^{5a}$ groups; or 5- or 6-membered heteroaryl optionally substituted with 1, 2, or 3 $R^{5a}$ groups;

each $R^{5a}$ is independently hydrogen, or halo; and
wherein each phenyl and heteroaryl group are independently optionally substituted with 1, 2, 3, 4, or 5 groups independently selected from the group consisting of halogen, halo-$C_{1-4}$ alkyl, —S-(halo-$C_{1-4}$ alkyl), $C_{1-4}$ alkoxy, halo-$C_{1-4}$ alkoxy, nitro, cyano, and $C_{1-4}$ alkoxycarbonyl; and
provided that the compound is not

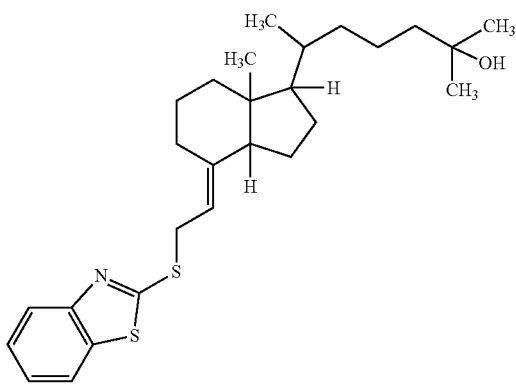 [SMILES: CC(CCCC(C)(C)O)C1CCC2/C(=C/CSc3nc4ccccc4s3)CCCC21C]

or a stereoisomer, mixture of stereoisomers, and/or a pharmaceutically acceptable salt thereof.

Embodiment 1B: Provided is a Compound of Embodiment 1, or a stereoisomer, mixture of stereoisomers, and/or a pharmaceutically acceptable salt thereof, wherein the double bond from a to b is in the E-configuration or Z-configuration;
$R^1$ is hydrogen; $R^1$ is

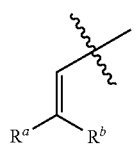

where $R^a$ and $R^b$ together with the carbon to which they are attached form an unsubstituted $C_5$-$C_7$-cycloalkyl group; $R^1$ is —$CH_2$—S-(heteroaryl) where the heteroaryl is optionally substituted with 1, 2, 3, 4, or 5 groups independently selected from the group consisting of halogen, halo-$C_{1-4}$ alkyl, —S-(halo-$C_{1-4}$ alkyl), $C_{1-4}$ alkoxy, halo-$C_{1-4}$ alkoxy, nitro, cyano, and $C_{1-4}$ alkoxycarbonyl; $R^1$ is —$CH_2$-(1,3-dioxo-isoindolin-2-yl); $R^1$ is

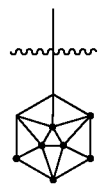

(ortho-carboranyl); $R^1$ is —$CH_2$—NH-(phenyl) where the phenyl is optionally substituted with 1, 2, 3, 4, or 5 groups independently selected from the group consisting of halogen, halo-$C_{1-4}$ alkyl, —S-(halo-$C_{1-4}$ alkyl), $C_{1-4}$ alkoxy, halo-$C_{1-4}$ alkoxy, nitro, cyano, and $C_{1-4}$ alkoxycarbonyl; $R^1$ is or

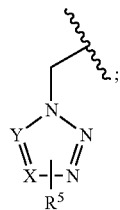

$R^{2a}$, $R^{2b}$, $R^3$, $R^{3a}$, $R^{3b}$, $R^4$, $R^{4a}$, and $R^{4b}$ are independently selected from hydrogen and halo;
one of X and Y is $CR^5$ and the other is CH; or one of X and Y is $CR^5$ and the other is N;
$R^5$ is hydrogen; $C_1$-$C_6$-alkyl; hydroxy-$C_1$-$C_6$-alkyl; aryl optionally substituted with 1, 2, or 3 $R^{5a}$ groups; or 5- or 6-membered heteroaryl optionally substituted with 1, 2, or 3 $R^{5a}$ groups; and
each $R^{5a}$ is independently hydrogen, alkyl, haloalkyl, or halo; and
provided that the compound is not

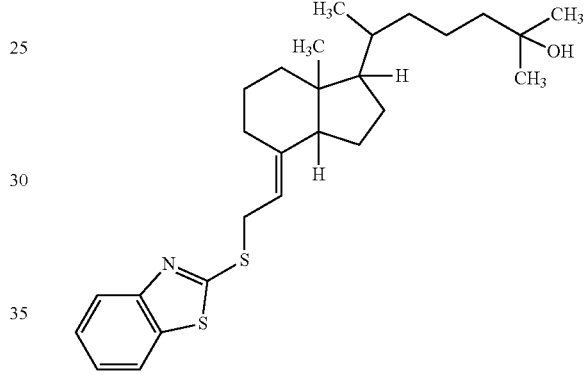

or a stereoisomer, mixture of stereoisomers, and/or a pharmaceutically acceptable salt thereof.

Embodiment 2: Provided is the Compound of Embodiment 1, 1A, or 1B, wherein
$R^1$ is hydrogen, —$CH_2$—S-(heteroaryl), —$CH_2$-(1,3-dioxo-isoindolin-2-yl),

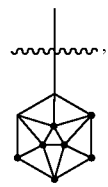

—$CH_2$—NH-(phenyl), or

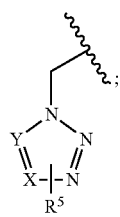

$R^{2a}$, $R^{2b}$, $R^3$, $R^{3a}$, $R^{3b}$, $R^4$, $R^{4a}$, and $R^{4b}$ are independently selected from hydrogen and halo; one of X and Y is $CR^5$ and the other is CH; or one of X and Y is $CR^5$ and the other is N;

$R^5$ is hydrogen; $C_1$-$C_6$-alkyl; hydroxy-$C_1$-$C_6$-alkyl; aryl optionally substituted with 1, 2, or 3 $R^{5a}$ groups; or 5- or 6-membered heteroaryl optionally substituted with 1, 2, or 3 $R^{5a}$ groups; and each $R^{5a}$ is independently hydrogen, alkyl, haloalkyl, or halo; and wherein each phenyl and heteroaryl group are independently optionally substituted with 1, 2, 3, 4, or 5 groups independently selected from the group consisting of halogen, halo-$C_{1-4}$ alkyl, —S-(halo-$C_{1-4}$ alkyl), $C_{1-4}$ alkoxy, halo-$C_{1-4}$ alkoxy, nitro, cyano, and $C_{1-4}$ alkoxycarbonyl.

In some or any embodiments of item 2, the phenyl and the heteroaryl groups are not substituted.

Embodiment 3A: Provided is the compound of Embodiment 1, 1B, or 2, wherein one $R^{5a}$ is hydrogen and the other $R^{5a}$ are independently hydrogen, alkyl, haloalkyl, or halo; or a stereoisomer, mixture of stereoisomers, and/or a pharmaceutically acceptable salt thereof.

Embodiment 3B: Provided is the compound of Embodiment 1, 1B, or 2, wherein two $R^{5a}$ are each hydrogen and the third $R^{5a}$ is alkyl, haloalkyl, or halo; or a stereoisomer, mixture of stereoisomers, and/or a pharmaceutically acceptable salt thereof.

Embodiment 3C: Provided is the compound of Embodiment 1, 1B, or 2, wherein one $R^{5a}$ is hydrogen and the other two $R^{5a}$ are independently alkyl, haloalkyl, or halo; or a stereoisomer, mixture of stereoisomers, and/or a pharmaceutically acceptable salt thereof.

Embodiment 3D: Provided is the compound of Embodiment 1, 1A, 1B, or 2, wherein two $R^{5a}$ are each hydrogen and the third $R^{5a}$ is halo; or a stereoisomer, mixture of stereoisomers, and/or a pharmaceutically acceptable salt thereof.

Embodiment 3E: Provided is the compound of Embodiment 1, 1A, 1B, or 2, wherein two $R^{5a}$ are each hydrogen and the third $R^{5a}$ is halo; or a stereoisomer, mixture of stereoisomers, and/or a pharmaceutically acceptable salt thereof.

Embodiment 4: Provided is the compound of any one of Embodiments 1-3E, wherein the Compound according to Formula (I) is according to Formula (Ia):

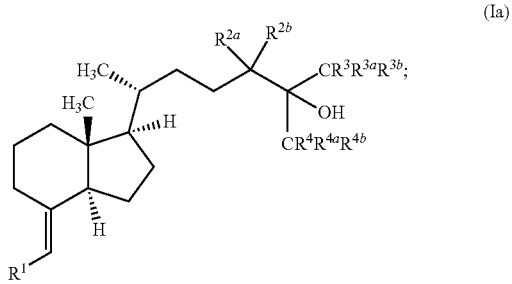

(Ia)

or a stereoisomer, mixture of stereoisomers, and/or a pharmaceutically acceptable salt thereof.

Embodiment 5: Provided is the compound of any one of Embodiments 1-4, wherein
$R^1$ is

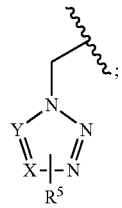

or a stereoisomer, mixture of stereoisomers, and/or a pharmaceutically acceptable salt thereof.

Embodiment 6: Provided is the Compound of any one of Embodiments 1-5, wherein one of X and Y is $CR^5$ and the other is CH; or a stereoisomer, mixture of stereoisomers, and/or a pharmaceutically acceptable salt thereof.

Embodiment 7: Provided is the Compound of any one of Embodiments 1-6, wherein X is $CR^5$ and Y is CH; or a stereoisomer, mixture of stereoisomers, and/or a pharmaceutically acceptable salt thereof.

Embodiment 8: Provided is the Compound of any one of Embodiments 1-5, wherein one of X and Y is $CR^5$ and the other is N; or a stereoisomer, mixture of stereoisomers, and/or a pharmaceutically acceptable salt thereof.

Embodiment 9: Provided is the Compound of any one of Embodiments 1-5 and 8, wherein X is $CR^5$ and Y is N; or a stereoisomer, mixture of stereoisomers, and/or a pharmaceutically acceptable salt thereof.

Embodiment 10: Provided is the Compound of any one of Embodiments 1-5 and 8, wherein Y is $CR^5$ and X is N; or a stereoisomer, mixture of stereoisomers, and/or a pharmaceutically acceptable salt thereof.

Embodiment 11: Provided is the Compound of any one of Embodiments 1-10, wherein $R^5$ is $C_1$-$C_6$-alkyl; phenyl optionally substituted with 1, 2, or 3 $R^{5a}$ groups; or 5-membered heteroaryl optionally substituted with 1, 2, or 3 $R^{5a}$ groups; or a stereoisomer, mixture of stereoisomers, and/or a pharmaceutically acceptable salt thereof.

Embodiment 12: Provided is the Compound of any one of Embodiments 1-11, wherein $R^5$ is aryl optionally substituted with 1, 2, or 3 $R^{5a}$ groups; or 5-membered heteroaryl optionally substituted with 1, 2, or 3 $R^{5a}$ groups; or a stereoisomer, mixture of stereoisomers, and/or a pharmaceutically acceptable salt thereof.

Embodiment 13: Provided is the Compound of any one of Embodiments 1-12, wherein $R^5$ is phenyl optionally substituted with 1, 2, or 3 $R^{5a}$ groups; or a stereoisomer, mixture of stereoisomers, and/or a pharmaceutically acceptable salt thereof.

Embodiment 14: Provided is the Compound of any one of Embodiments 1-12, wherein $R^5$ is 5-membered heteroaryl optionally substituted with 1, 2, or 3 $R^{5a}$ groups; or a stereoisomer, mixture of stereoisomers, and/or a pharmaceutically acceptable salt thereof. In an embodiment, provided is the Compound of any one of Embodiments 1-12, wherein $R^5$ is 6-membered heteroaryl optionally substituted with 1, 2, or 3 $R^{5a}$ groups; or a stereoisomer, mixture of stereoisomers, and/or a pharmaceutically acceptable salt thereof.

Embodiment 15: Provided is the Compound of any one of Embodiments 1-14, wherein $R^{2a}$ and $R^{2b}$ are independently hydrogen or fluoro; or a stereoisomer, mixture of stereoisomers, and/or a pharmaceutically acceptable salt thereof.

Embodiment 16: Provided is the Compound of any one of Embodiments 1-14, wherein $R^{2a}$ and $R^{2b}$ are independently halo; or a stereoisomer, mixture of stereoisomers, and/or a pharmaceutically acceptable salt thereof.

Embodiment 17: Provided is the Compound of any one of Embodiments 1-14, wherein $R^{2a}$ and $R^{2b}$ are each fluoro; or a stereoisomer, mixture of stereoisomers, and/or a pharmaceutically acceptable salt thereof.

Embodiment 18: Provided is the Compound of any one of Embodiments 1-14, wherein $R^{2a}$ and $R^{2b}$ are each hydrogen; or a stereoisomer, mixture of stereoisomers, and/or a pharmaceutically acceptable salt thereof.

Embodiment 19: Provided is the Compound of any one of Embodiments 1-18, wherein $R^3$, $R^{3a}$, $R^{3b}$, $R^4$, $R^{4a}$, and $R^{4b}$ are each hydrogen; or a stereoisomer, mixture of stereoisomers, and/or a pharmaceutically acceptable salt thereof.

Embodiment 20: Provided is the Compound of any one of Embodiments 1-18, wherein $R^3$, $R^{3a}$, $R^{3b}$, $R^4$, $R^{4a}$, and $R^{4b}$ are each independently halo; or a stereoisomer, mixture of stereoisomers, and/or a pharmaceutically acceptable salt thereof.

Embodiment 21: Provided is the Compound of any one of Embodiments 1-18, wherein $R^3$, $R^{3a}$, $R^{3b}$, $R^4$, $R^{4a}$, and $R^{4b}$ are each fluoro; or a stereoisomer, mixture of stereoisomers, and/or a pharmaceutically acceptable salt thereof.

Embodiment 22: Provided is the Compound of any one of Embodiments 1-21, wherein the bond from a to b is in the E-configuration; or a stereoisomer, mixture of stereoisomers, and/or a pharmaceutically acceptable salt thereof.

Embodiment 22a: Provided is the Compound of any one of Embodiments 1-14, wherein at least one of $R^{2a}$, $R^{2b}$, $R^3$, $R^{3a}$, $R^{3b}$, $R^4$, $R^{4a}$, and $R^{4b}$ is halo (in some embodiments, fluoro), at least two of $R^{2a}$, $R^{2b}$, $R^3$, $R^{3a}$, $R^{3b}$, $R^4$, $R^{4a}$, and $R^{4b}$ are independently halo (in some embodiments, fluoro), at least three of $R^{2a}$, $R^{2b}$, $R^3$, $R^{3a}$, $R^{3b}$, $R^4$, $R^{4a}$, and $R^{4b}$ are independently halo (in some embodiments, fluoro), at least four of $R^{2a}$, $R^{2b}$, $R^3$, $R^{3a}$, $R^{3b}$, $R^4$, $R^{4a}$, and $R^{4b}$ are independently halo (in some embodiments, fluoro), at least five of $R^{2a}$, $R^{2b}$, $R^3$, $R^{3a}$, $R^{3b}$, $R^4$, $R^{4a}$, and $R^{4b}$ are independently halo (in some embodiments, fluoro), or at least six of $R^{2a}$, $R^{2b}$, $R^3$, $R^{3a}$, $R^{3b}$, $R^4$, $R^{4a}$, and $R^{4b}$ are independently halo (in some embodiments, fluoro). In an embodiment, provided is the Compound of any one of items 1-13, wherein one of $R^{2a}$, $R^{2b}$, $R^3$, $R^{3a}$, $R^{3b}$, $R^4$, $R^{4a}$, and $R^{4b}$ is halo (in some embodiments, fluoro), two of $R^{2a}$, $R^{2b}$, $R^3$, $R^{3a}$, $R^{3b}$, $R^4$, $R^{4a}$, and $R^{4b}$ are independently halo (in some embodiments, fluoro), three of $R^{2a}$, $R^{2b}$, $R^3$, $R^{3a}$, $R^{3b}$, $R^4$, $R^{4a}$, and $R^{4b}$ are independently halo (in some embodiments, fluoro), four of $R^{2a}$, $R^{2b}$, $R^3$, $R^{3a}$, $R^{3b}$, $R^4$, $R^{4a}$, and $R^{4b}$ are independently halo (in some embodiments, fluoro), five of $R^{2a}$, $R^{2b}$, $R^3$, $R^{3a}$, $R^{3b}$, $R^4$, $R^{4a}$, and $R^{4b}$ are independently halo (in some embodiments, fluoro), or six of $R^{2a}$, $R^{2b}$, $R^3$, $R^{3a}$, $R^{3b}$, $R^4$, $R^{4a}$, and $R^{4b}$ are independently halo (in some embodiments, fluoro).

Embodiment 23: Provided is the compound of Embodiment 1, selected from the group consisting of:

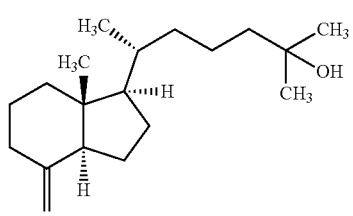

10

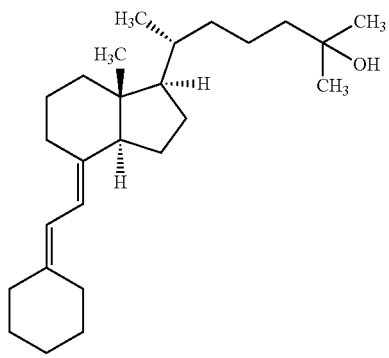

14

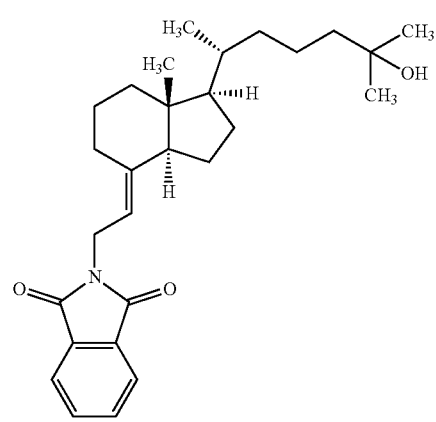

16

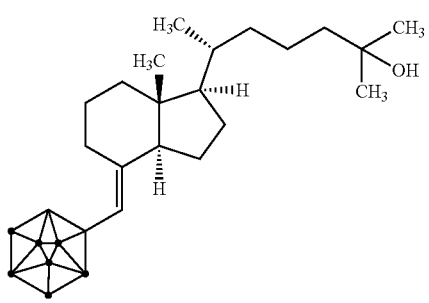

17

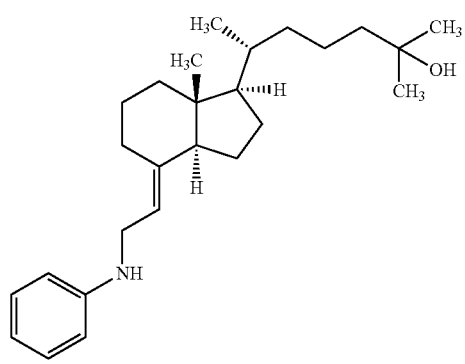

18

-continued
21
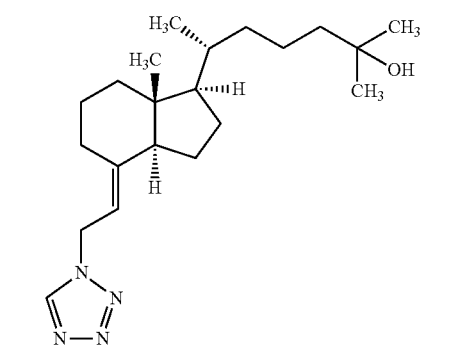
22
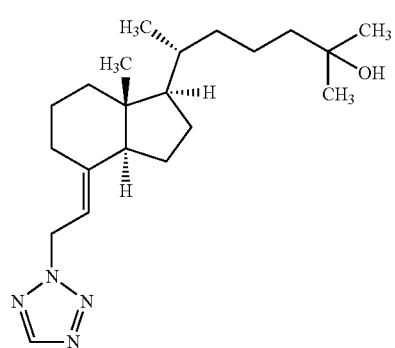
23
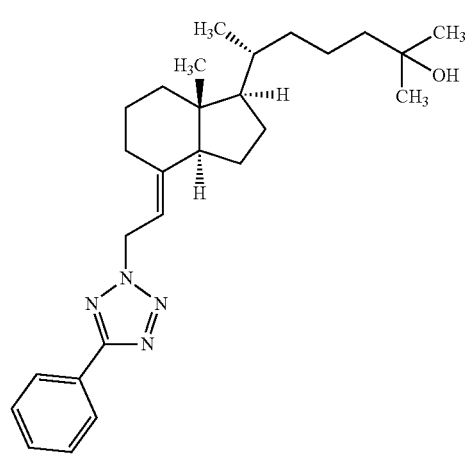
24
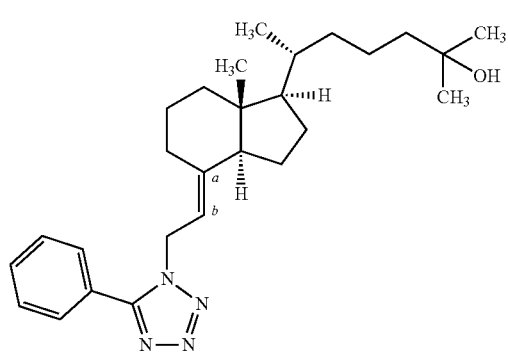
-continued
25
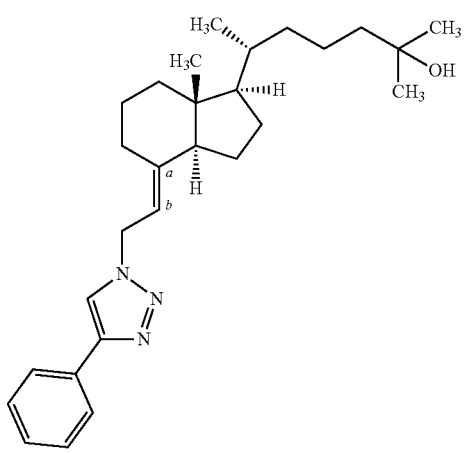
26
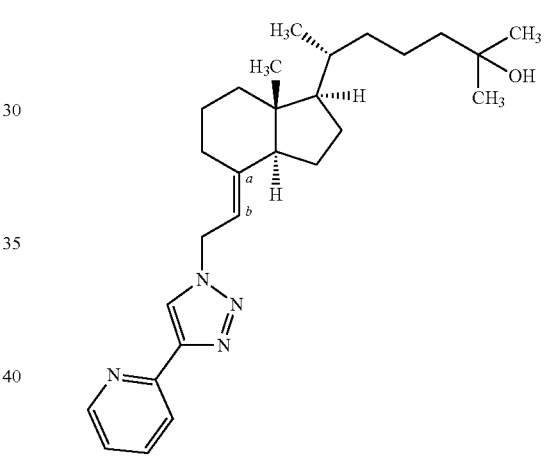
27
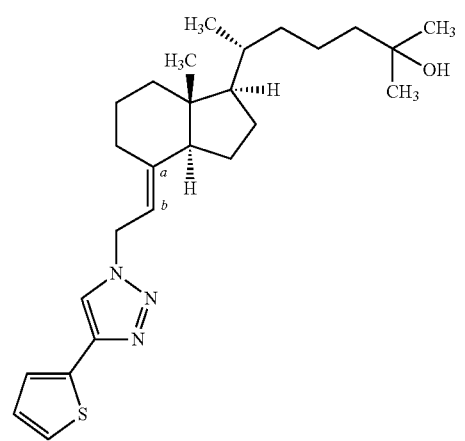

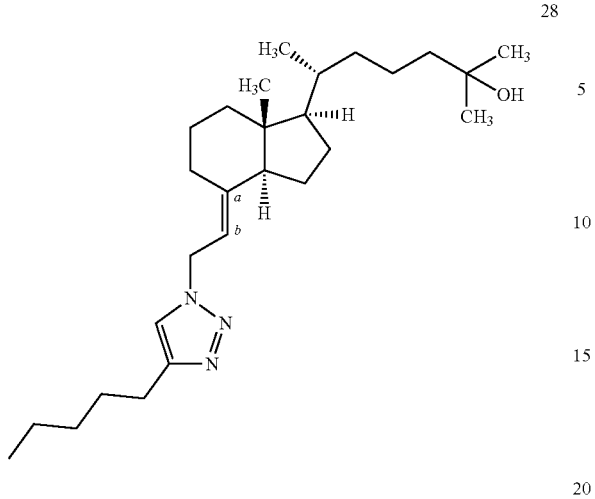
28
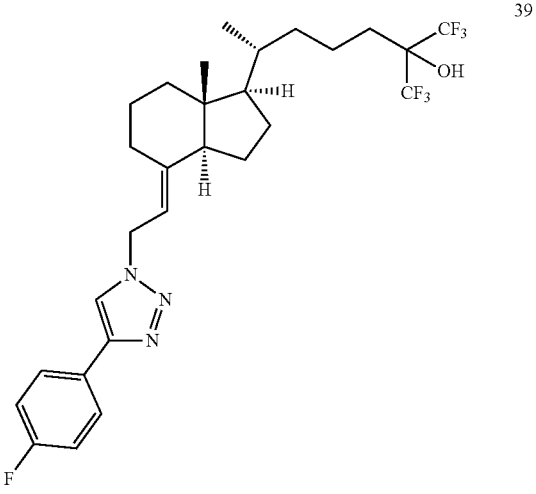
39
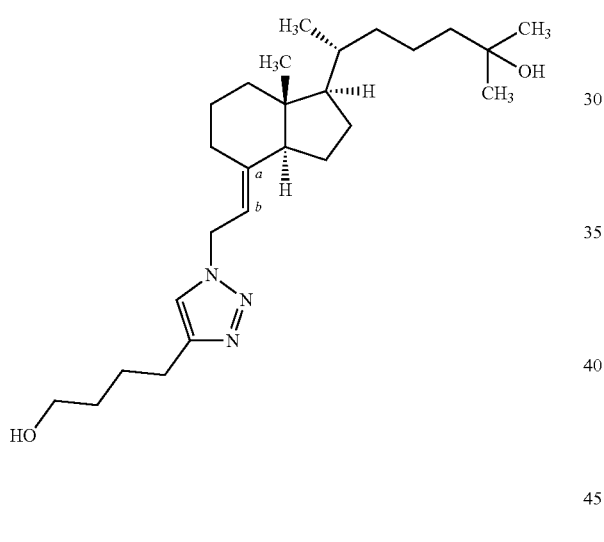
29
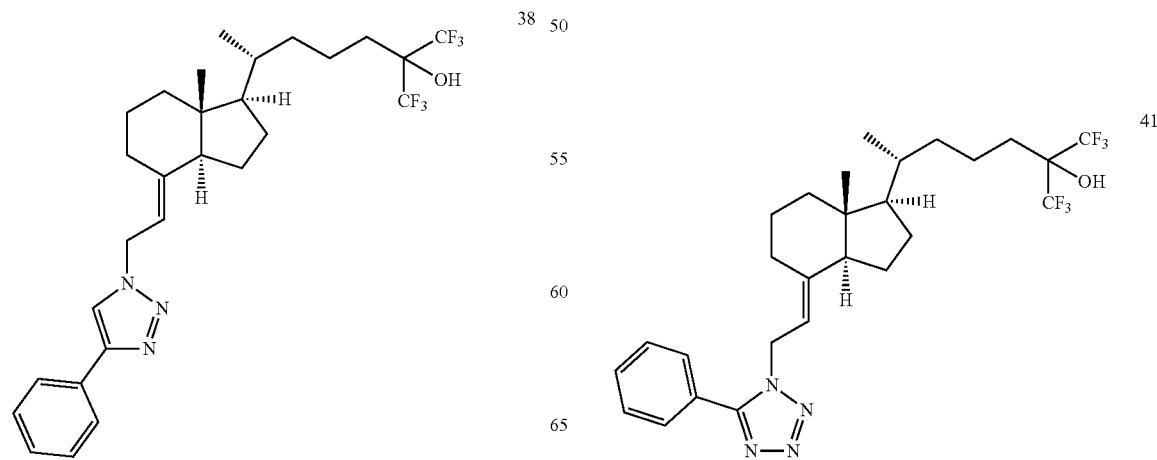

46
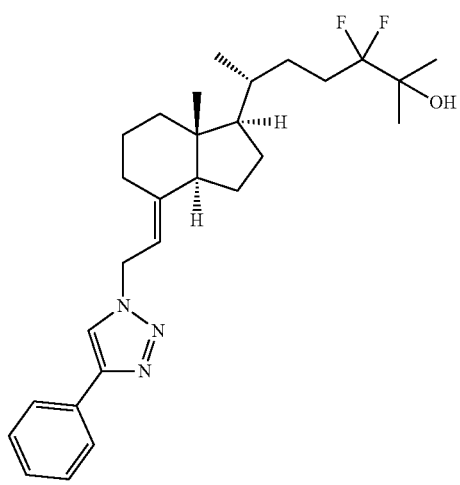
47
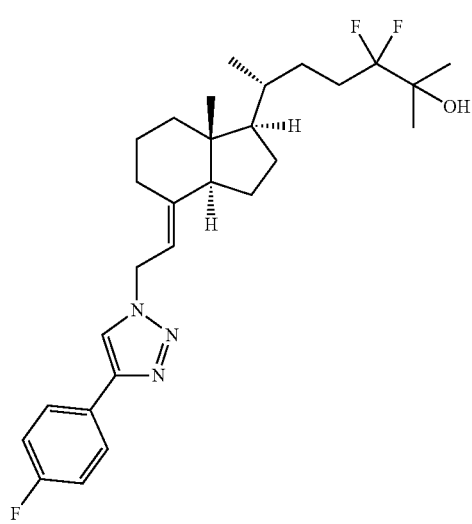
48
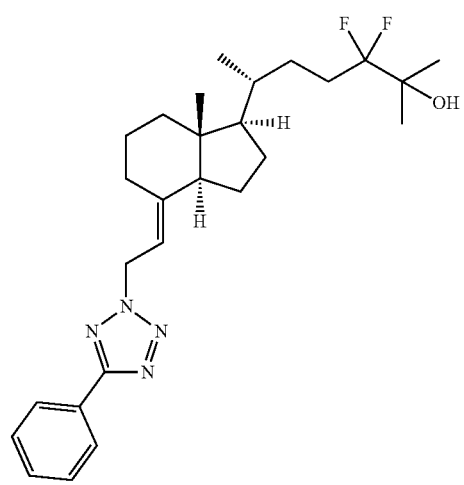
49
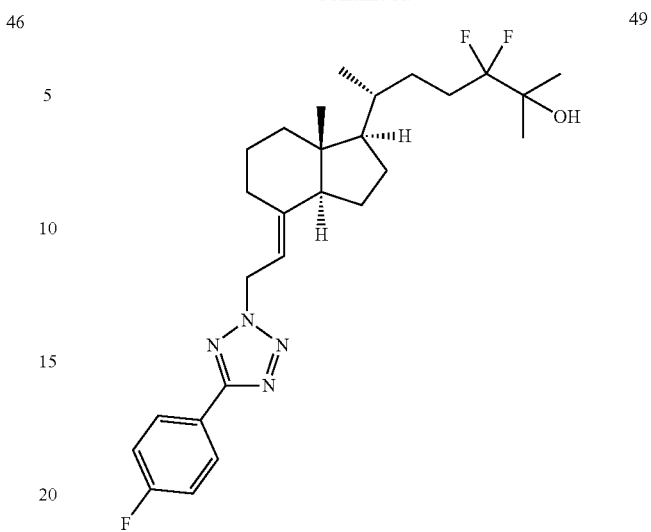
50
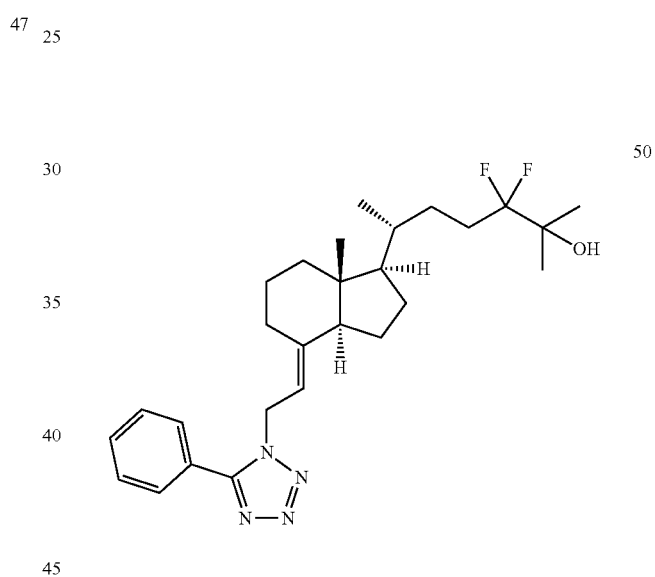
51
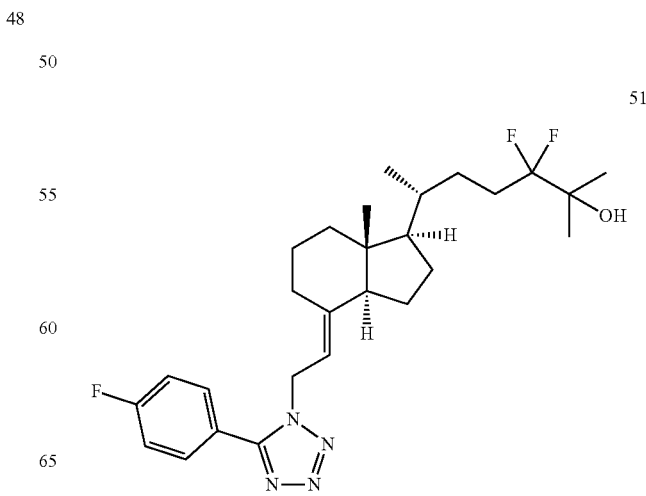

52
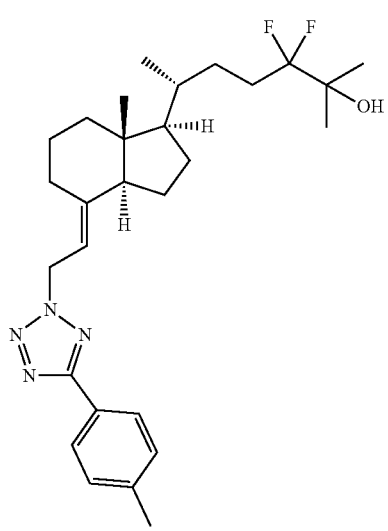
53
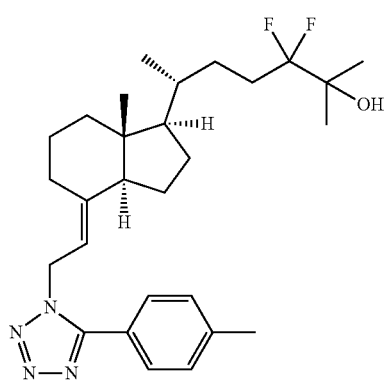
54
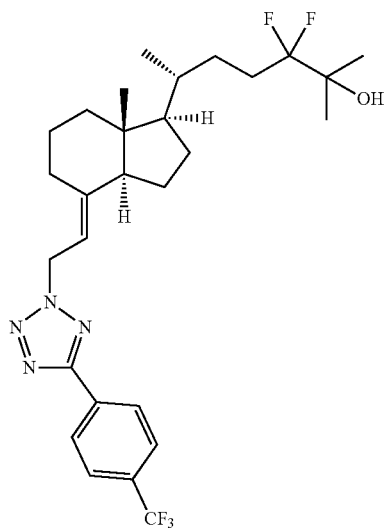
55
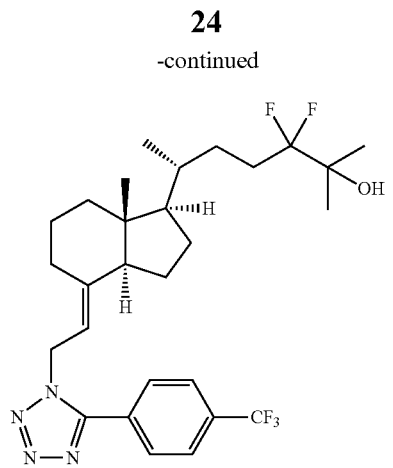
56
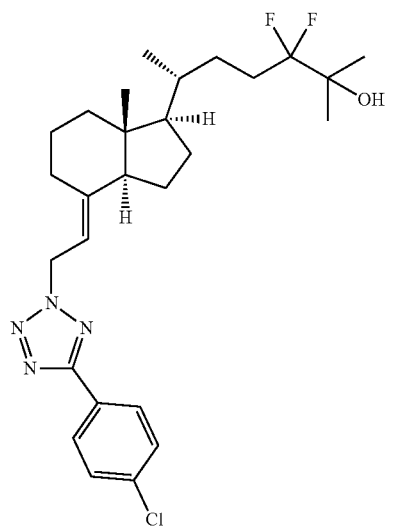
57
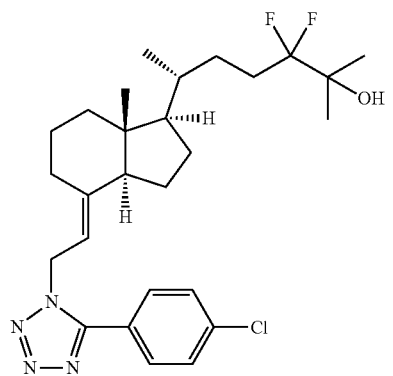

58
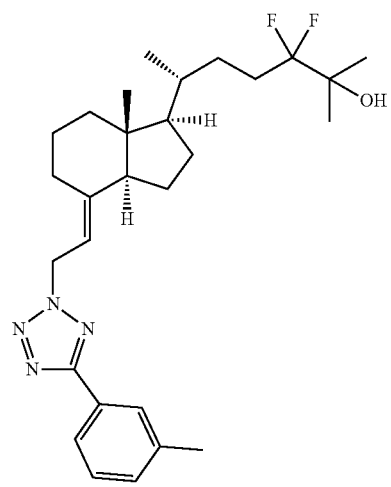
59
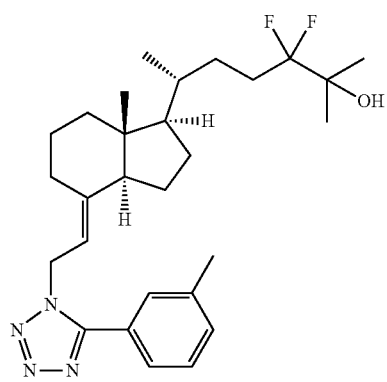
60
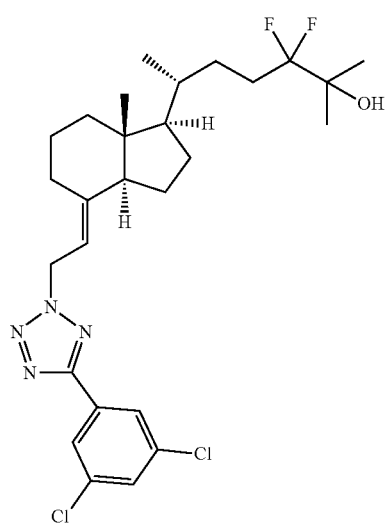
61
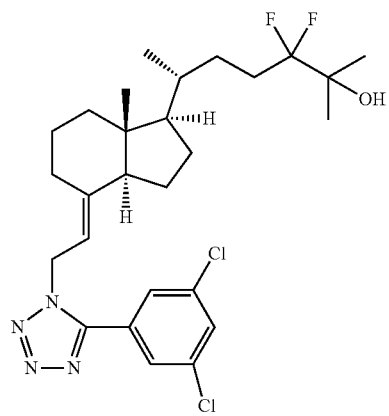
62
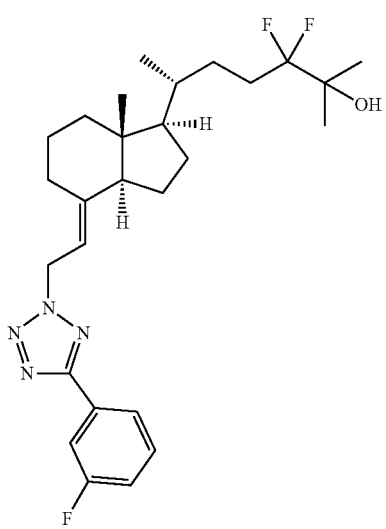
63
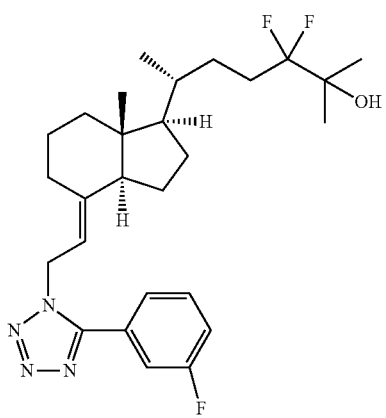

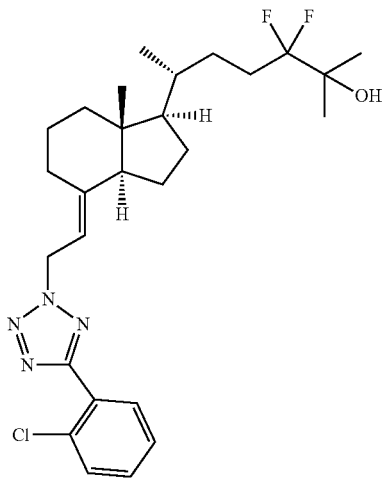

64

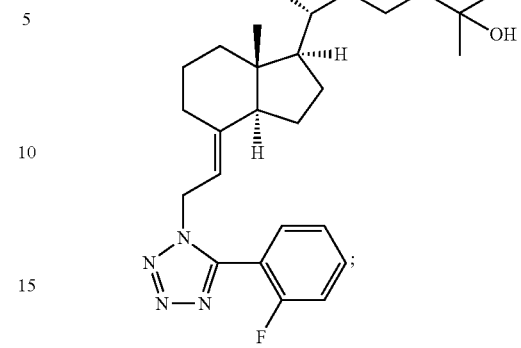

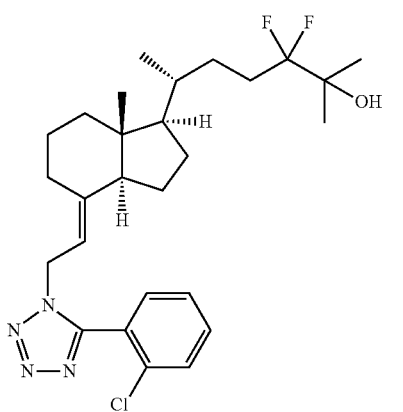

65

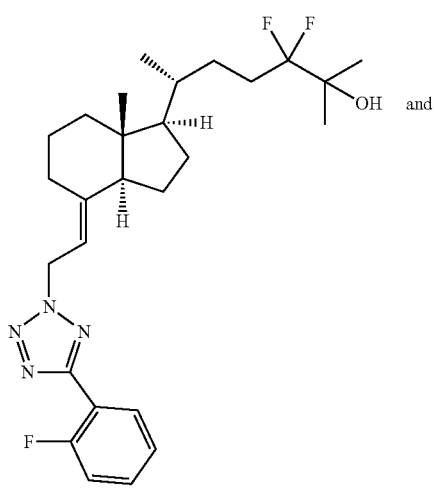

66 or a stereoisomer, mixture of stereoisomers, and/or a pharmaceutically acceptable salt thereof.

Embodiments 24: Provided is a pharmaceutical composition comprising a therapeutically effective amount of a compound of any one of Embodiments 1-23, or a stereoisomer, mixture of stereoisomers, and/or a pharmaceutically acceptable salt thereof; and a pharmaceutically acceptable carrier.

Embodiments 25: Provided is a method for inhibiting SREBPs in a subject, comprising the step of administering to the subject in need thereof a therapeutically effective amount of the compound of any one of Embodiments 1 to 23 or a pharmaceutically acceptable salt thereof, or a therapeutically effective amount of the pharmaceutical composition of Embodiment 24.

Embodiments 26: Provided is a method for treating metabolic disease, a liver disease, obesity, diabetes, cardiovascular disease, hyperlipidemia, or cancer in a subject, comprising the step of administering to the subject in need thereof a therapeutically effective amount of the compound of any one of Embodiments 1 to 23 or a pharmaceutically acceptable salt thereof, or a therapeutically effective amount of the pharmaceutical composition of Embodiment 24.

Embodiments 27: Provided is a use of the compound of any one of Embodiments 1 to 23 or a pharmaceutically acceptable salt thereof or the pharmaceutical composition of Embodiment 24 in the manufacture of a medicament for the treatment of metabolic disease, a liver disease, obesity, diabetes, cardiovascular disease, hyperlipidemia, or cancer.

Embodiments 28: Provided is a compound of any one of Embodiments 1 to 23 or a pharmaceutically acceptable salt thereof or a pharmaceutical composition of Embodiment 24 for use in the treatment of a metabolic disease, a liver disease, obesity, diabetes, cardiovascular disease, or hyperlipidemia, cancer.

Embodiments 29: Provided is the method or use of any one of Embodiments 26-28 wherein the cancer is selected from prostate cancer, liver cancer, bile duct cancer, bone cancer, breast cancer, colon cancer, colorectal cancer, endometrial cancer, esophageal cancer, hematological cancer (including a lymphoma and a leukemia), kidney cancer, lung cancer, ovarian cancer, pancreatic cancer, head and neck squamous cell carcinoma, squamous cell skin cancer, skin melanoma, and uveal melanoma. In an embodiment of embodiment 30, provided is the method or use of any one of Embodiments 26-28 wherein the cancer is selected from prostate cancer, liver cancer, breast cancer, skin melanoma, and uveal melanoma.

Embodiments 30: Provided is a method of Embodiments 26 or a use of Embodiments 27 and 28, wherein the disease is obesity, non-alcoholic steatohepatitis (NASH), fatty liver disease, or cancer.

Embodiments 31: In any one of Embodiments 26, 27, and 28, wherein the disease is hypertriglyceridemia. In any one of Embodiments 26, 27, and 28, wherein the disease is hypercholesteremia.

Embodiments 32: Provided is a compound of any one of Embodiments 1 to 23 or a pharmaceutically acceptable salt thereof or a pharmaceutical composition of Embodiment 24 for use in therapy.

The pharmaceutically acceptable salt used herein refers to any salts which are known in the art and do not have excess toxicity. In particular, the pharmaceutically acceptable salt may include a salt with an inorganic acid, an organic acid, an inorganic base, or an organic base. Such an inorganic acid includes hydrofluoric acid, hydrochloric acid, hydrobromic acid, hydroiodic acid, nitric acid, sulfuric acid, and phosphoric acid. Such an organic acid includes acetic acid, trifluoroacetic acid, benzoic acid, p-toluenesulfonic acid, citric acid, oxalic acid, maleic acid, fumaric acid, lactic acid, malic acid, succinic acid, and tartaric acid. Such an inorganic base includes lithium, sodium potassium, magnesium, calcium, aluminum, and zinc. Such an organic base includes arginine and lysine. In some or any embodiments, the pharmaceutically acceptable salt is a salt with an inorganic acid, and in particular hydrochloride.

The pharmaceutically acceptable carrier used herein includes various conventional organic or inorganic carrier substances, in some embodiments, substances in solid preparations such as excipients, disintegrators, binders, glidants and lubricants, commonly used in the art, and substances in liquid preparations such as solvents, solubilizing agents, suspending agents, isotonizing agents, buffers and soothing agents, commonly used in the art. Additives commonly used in the art such as preservatives, antioxidants, colorants, and edulcorants may be added to a pharmaceutical composition disclosed herein, if needed.

The compound of Formula (I) may be orally or parenterally administered in a therapeutically effective amount to mammals such as mice, rats, hamsters, guinea pigs, rabbits, cats, dogs, pigs, cattle, horses, sheep, monkeys, and human. While the therapeutically effective amount of the compound of Formula (I) may vary depending on subjects, diseases, dosage forms, routes of administration, and the like, the therapeutically effective amount of the compound of Formula (I) generally ranges for example from about 0.01 mg through about 0.1 mg to about 1 g through about 10 g per day, which may be administered once or several times in a divided amount.

For the avoidance of doubt, it is confirmed that in the general description above and throughout, the proposal of general preferences and options in respect of different features of the compounds, methods, use, and compositions constitutes in the usual way the proposal of general combinations of those general preferences and options for the different features, insofar as they are combinable and compatible and are put forward in the same context.

Preparation of the Compounds Disclosed Herein

A method for preparing the compound of Formula (I) or a pharmaceutically acceptable salt thereof is illustrated as below, but is not limited thereto. For example, the schemes as below show illustrative preparation methods for exemplary compounds disclosed herein. Compounds obtained in each step may be isolated or purified by known methods including distillation, recrystallization, column chromatography, etc., if needed, and may be also used in the next step without isolation or purification.

$^1$H and $^{13}$C NMR spectra were recorded on JEOL AL-400 NMR (400 MHz) and ECP-600 NMR (600 MHz) spectrometers. $^1$H NMR spectra were referenced with $(CH_3)_4Si$ ($\delta$ 0.00 ppm) as an internal standard. $^{13}$C NMR spectra were referenced with deuterated solvent ($\delta$ 77.0 ppm for $CDCl_3$ and 49.3 ppm for $CD_3OD$). IR spectra were recorded on the JASCO FT-IR-800 Fourier transform infrared spectrophotometer. High-resolution mass spectra were obtained on a SHIMADZU LCMS-IT-TOF mass spectrometer with a positive electrospray ionization (ESI) method. Optical rotations were measured on a JASCO DIP-370 digital polarimeter. Column chromatography was performed on silica gel 60N (Kanto Chemical Co., Inc., 100-210 μm) or silica gel 60 (Merck, 0.040-0.063 mm). Preparative thin-layer chromatography was performed on silica gel 60 F254 (Merck, 0.5 mm). All experiments were performed under anhydrous conditions and an argon atmosphere unless otherwise stated.

The following general schemes can be used to prepare Compounds of Formula (I).

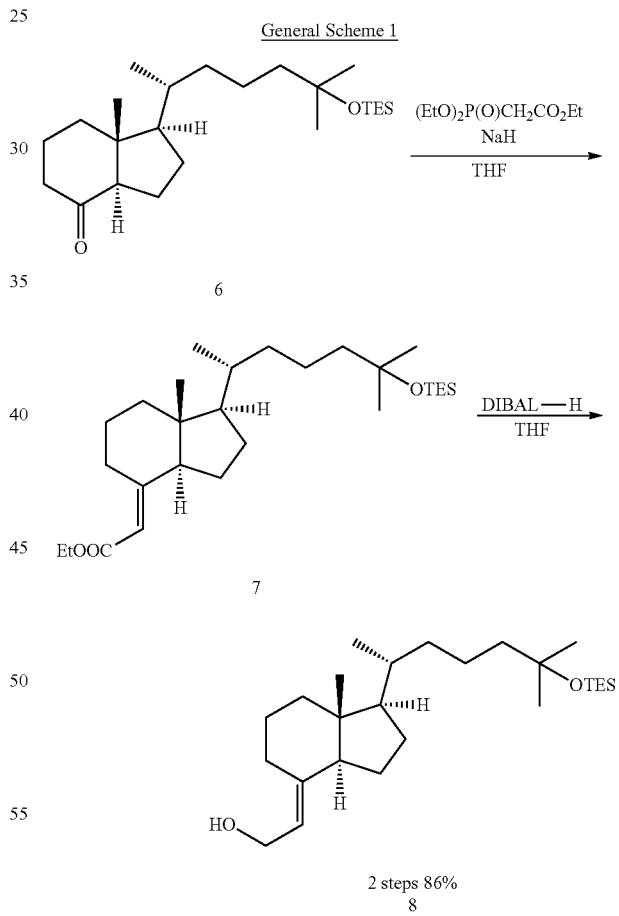

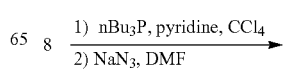

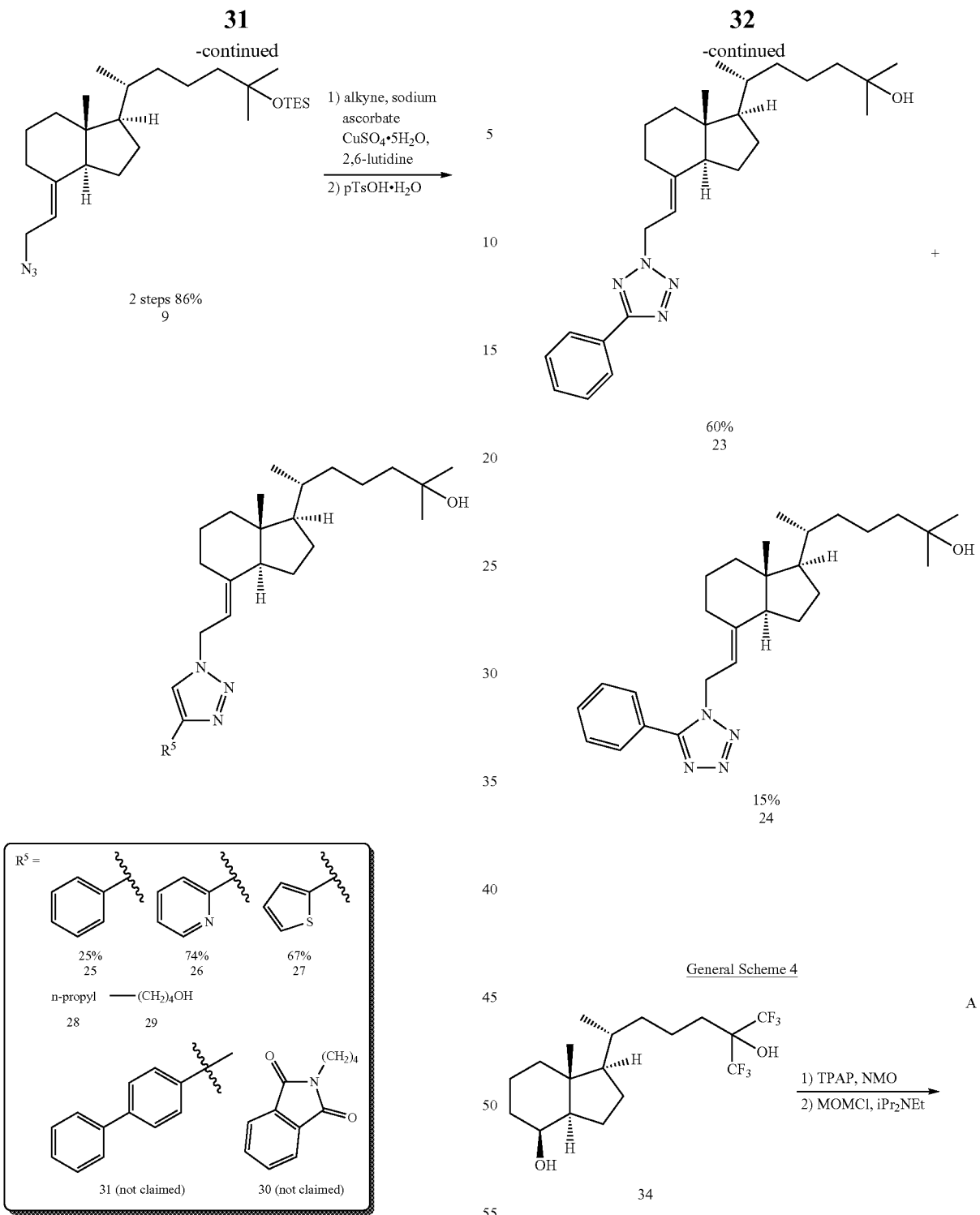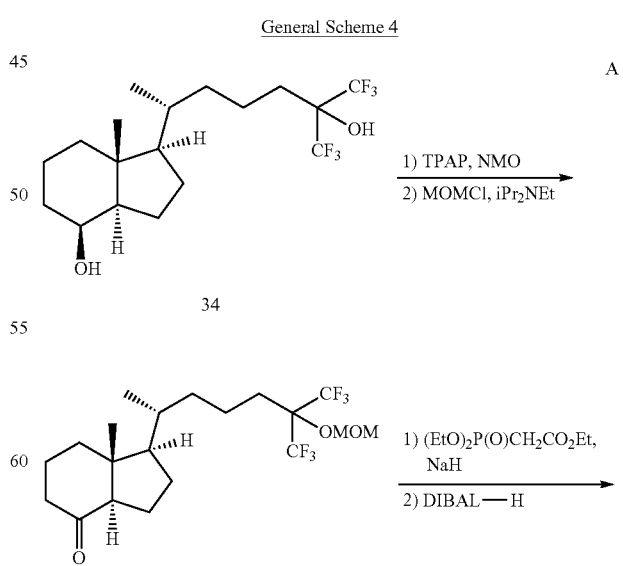

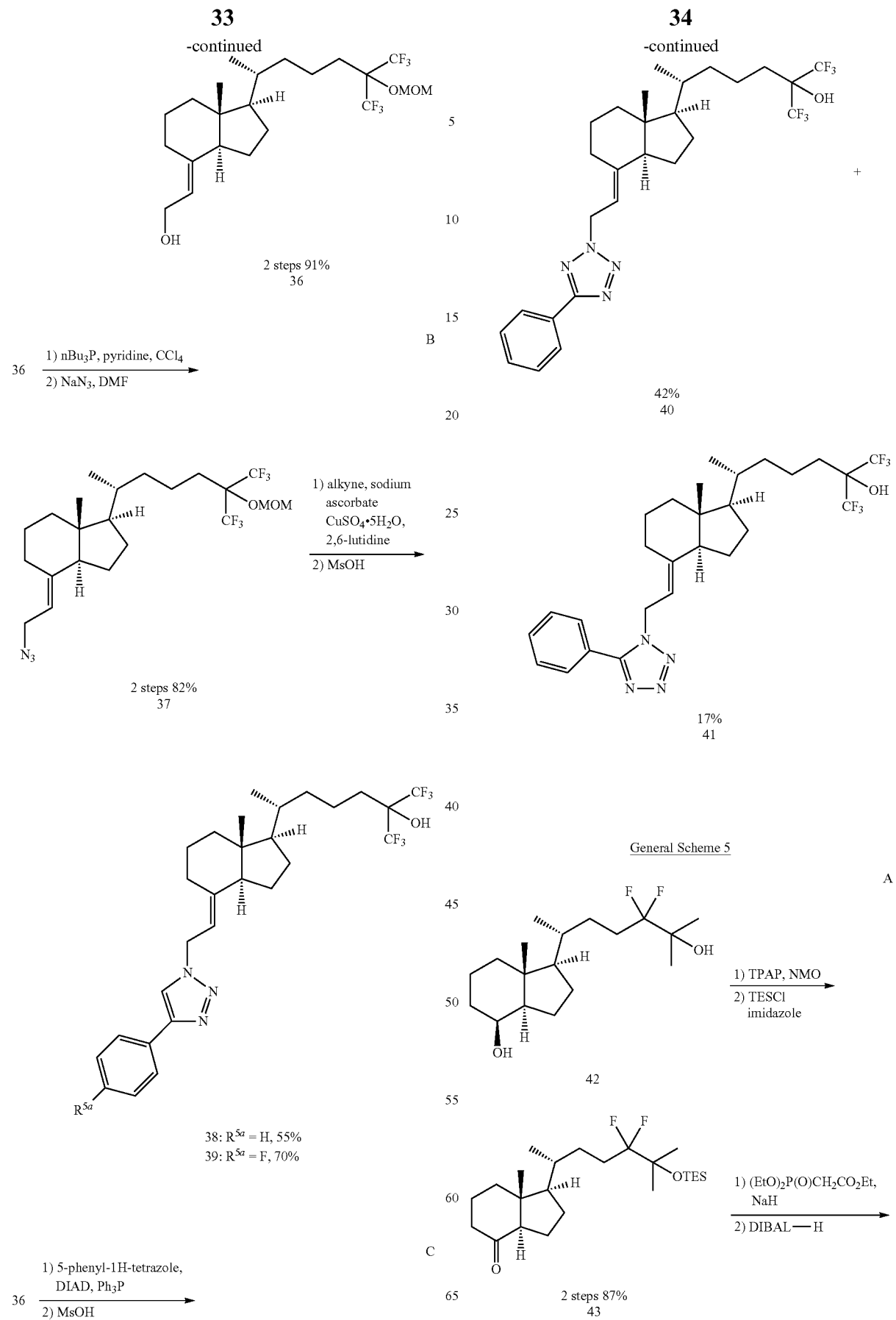

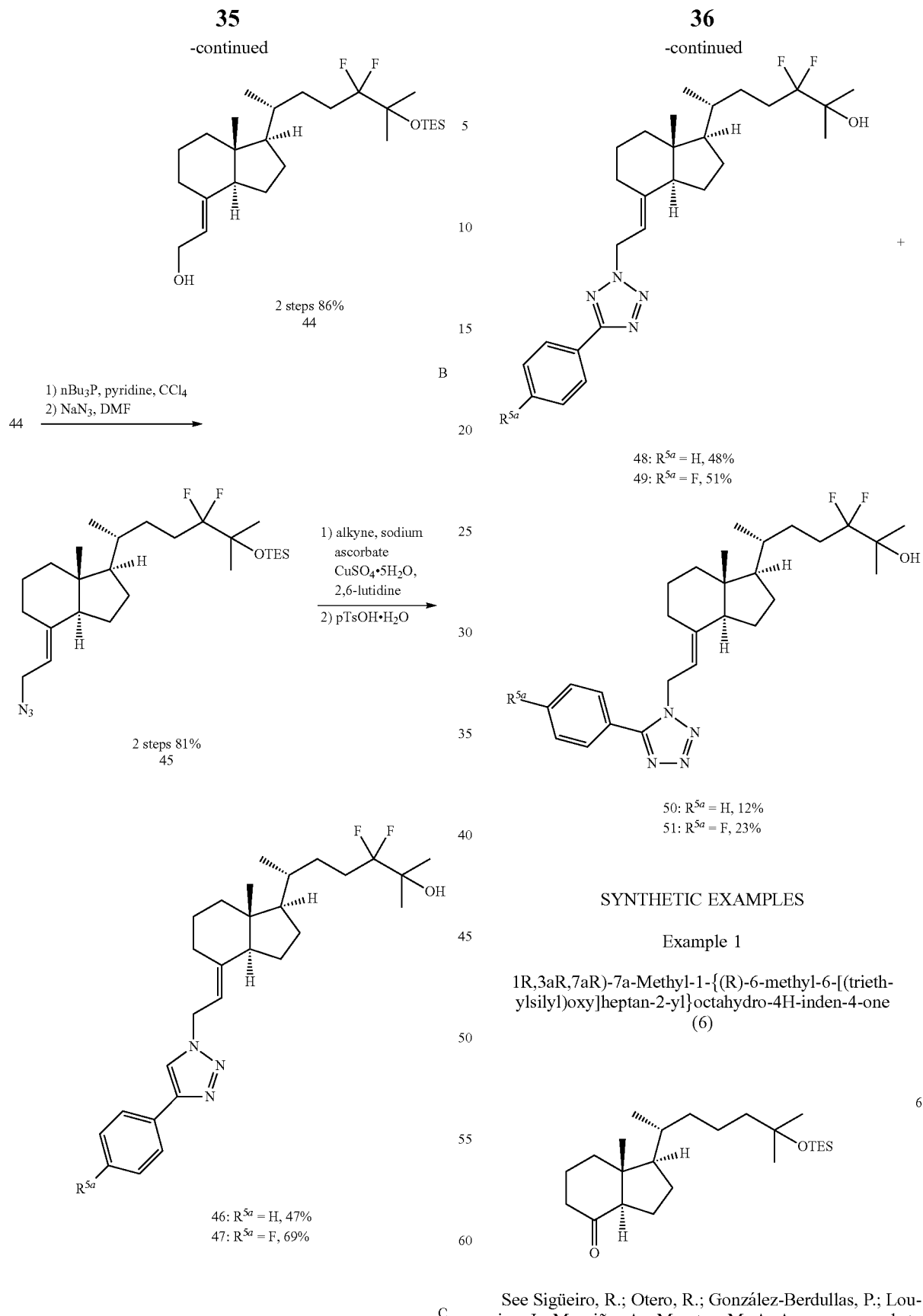
SYNTHETIC EXAMPLES
Example 1
1R,3aR,7aR)-7a-Methyl-1-{(R)-6-methyl-6-[(triethylsilyl)oxy]heptan-2-yl}octahydro-4H-inden-4-one (6)
See Sigüeiro, R.; Otero, R.; González-Berdullas, P.; Loureiro, J.; Mouriño, A.; Maestro, M. A. A new approach to 19-nor-A-ring phosphine oxide for the convergent synthesis of 19-nor-calcitriol. *J Steroid Biochem. Mol. Biol.* 2017, 173, 86-88.

(R)-2-Methyl-6-[(1R,3aS,7aR)-7a-methyl-4-methyleneoctahydro-1H-inden-1-yl]heptan-2-ol (10 KK-023)

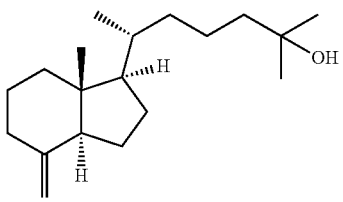

10 KK-023

To the suspension of the methyltriphenylphosphonium bromide (90.5 mg, 0.253 mmol) in THF (2 mL) was added n-BuLi (146 µL, 1.65 M in hexane, 0.241 mmol) at −78° C. and stirred at the same temperature for 15 min and 0° C. for 20 min. To the mixture was added 8-keto CD ring (6) (50.0 mg, 0.127 mmol) in THF (2 mL) and stirred at the same temperature for 1 h. After the reaction was quenched with H$_2$O and saturated aqueous NH$_4$Cl at 0° C., the mixture was extracted with EtOAc twice, dried over Na$_2$SO4, filtered, and concentrated. The obtained residue was used for the next reaction without further purification.

Tetrabutylammonium fluoride (381 µL, 1 M in THF, 0.381 mmol) was added to a solution of the above crude residue in THF (5 mL). The mixture was stirred at room temperature for 24 h. After the reaction was quenched with H$_2$O and saturated aqueous NH$_4$Cl at room temperature, the mixture was extracted with EtOAc three times, dried over Na$_2$SO$_4$, filtered, and concentrated. The residue was purified by flash column chromatography on silica gel (hexane:EtOAc=5:1) to obtain 10 KK-023 (9.6 mg, 27%, 2 steps) as a colorless oil.

10 KK-023: [α]D$^{27}$+63.5 (c 0.754, CHCl$_3$); IR (neat) 3360, 1649, 1469, 1378, 1148, 885 cm-1; $^1$H NMR (400 MHz, CDCl3) δ 0.56 (s, 3H), 0.94 (d, J=6.4 Hz, 3H), 1.02-1.09 (m, 1H), 1.21-1.64 (m, 1H), 1.84-2.01 (m, 4H), 2.26 (dd, J=4.1, 13.3 Hz, 1H), 4.46 (d, J=1.8 Hz, 1H), 4.72 (d, J=1.8 Hz, 1H); $^{13}$C NMR (100 MHz, CDCl$_3$) δ 11.7, 18.8, 20.8, 22.2, 23.7, 27.7, 29.2, 29.4, 35.4, 36.1, 36.4, 40.2, 44.4, 45.1, 55.3, 56.3, 71.1, 105.0, 149.6; HRMS (ESI$^+$) calcd for C$_{19}$H$_{33}$ [M-OH]$^+$ 261.2577, found 261.2577.

Example 2

2-[(1R,3aS,7aR,E)-7a-methyl-1-{(R)-6-methyl-6-[(triethylsilyl)oxy] heptan-2-yl}octahydro-4H-inden-4-ylidene]ethan-1-ol (8)

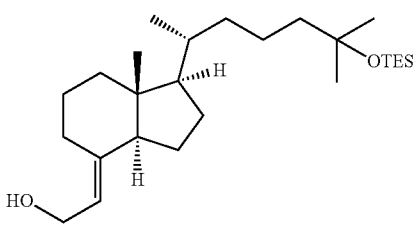

8

See Ono, K.; Yoshida, A.; Saito, N.; Fujishima, T.; Honzawa, S.; Suhara, Y.; Kishimoto, S.; Sugiura, T.; Waku, K.; Takayama, H.; Kittaka, A. Efficient synthesis of 2-modified 1α,25-dihydroxy-19-norvitamin D3 with Julia olefination: high potency in induction of differentiation on HL-60 cells. J. Org. Chem. 2003, 68, 7407-7415.

(R)-6-[(1R,3aS,7aR,E)-4-(2-hydroxyethylidene)-7a-methyloctahydro-1H-inden-1-yl]-2-methylheptan-2-ol (11 KK-025)

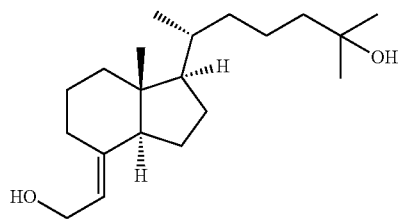

11 KK-025

See Asano, L.; Watanabe, M.; Ryoden, Y.; Usuda, K.; Yamaguchi, T.; Khambu, B.; Takashima, M.; Sato, S.; Sakai, J.; Nagasawa, K.; Uesugi, M. Vitamin D metabolite, 25-hydroxyvitamin D, regulates lipid metabolism by inducing degradation of SREBP/SCAP. Cell Chem. Biol. 2017, 24, 207-217.

Example 3

(R)-6-{(1R,3aS,7aR,E)-4-[2-(Benzo[d]thiazol-2-ylthio)ethylidene]-7a-methyloctahydro-1H-inden-1-yl}-2-methylheptan-2-ol (15 KK-026)

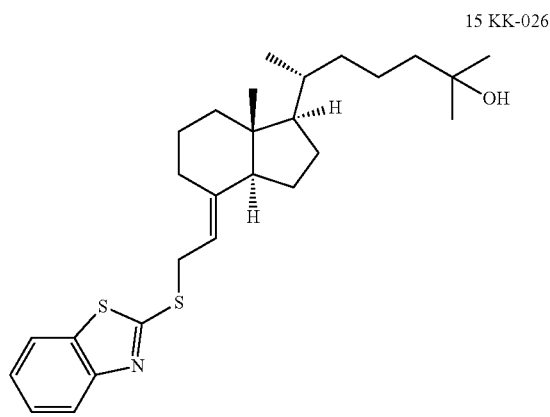 [SMILES: C[C@H](CCCC(C)(C)O)[C@H]1CC[C@H]2/C(=C/CSc3nc4ccccc4s3)CCC[C@]12C]

15 KK-026

To a solution of 2-mercaptobenzothiazole (29.7 mg, 0.178 mmol), Ph$_3$P (29.9 mg, 0.114 mmol), and 8 (30.7 mg, 0.073 mmol) in CH$_2$Cl$_2$ (10 mL) was added diisopropyl azodicarboxylate (60 µL, 1.9 M in toluene, 0.114 mmol) at 0° C., and the mixture was stirred at the same temperature for 2 h. After the reaction was quenched with H$_2$O at 0° C., the mixture was extracted with CH$_2$Cl$_2$ three times, dried over Na$_2$SO4, filtered, and concentrated. The residue was roughly purified by flash column chromatography on silica gel (hexane:EtOAc=10:1) to obtain the crude sulfide.

Tetrabutylammonium fluoride (111 µL, 1 M in THF, 0.111 mmol) was added to a solution of the above crude sulfide in THF (5 mL). The mixture was stirred at room temperature for 21 h. After the reaction was quenched with H₂O and saturated aqueous NH₄Cl at room temperature, the mixture was extracted with EtOAc three times, washed with brine, dried over Na₂SO4, filtered, and concentrated. The residue was purified on a preparative silica gel TLC plate (hexane: EtOAc=5:1) to obtain 15 KK-026 (16.1 mg, 50%, 2 steps) as a colorless oil.

15 KK-026: $[\alpha]_D^{27}$ +77.3 (c 1.24, CHCl3); IR (neat) 3390, 1457, 1427, 1377, 1238, 996, 756 cm-1; ¹H NMR (400 MHz, CDCl3) δ 0.49 (s, 3H), 0.93 (d, J=6.4 Hz, 3H), 1.00-1.08 (m, 1H), 1.21-1.73 (m, 21H), 1.81-2.00 (m, 3H), 1.81-2.00 (m, 3H), 2.74-2.78 (m, 1H), 4.02 (dd, J=7.1, 12.4 Hz, 1H), 4.13 (dd, J=7.8, 12.8 Hz, 1H), 5.20 (t, J=8.0 Hz, 1H), 7.28 (td, J=1.4, 8.2 Hz, 1H), 7.41 (td, J=1.4, 7.8 Hz, 1H), 7.75 (dd, J=1.4, 7.8 Hz, 1H), 7.86 (d, J=7.8 Hz, 1H); 13C NMR (100 MHz, CDCl3) δ 11.7, 18.8, 20.8, 22.1, 23.5, 27.6, 28.8, 29.2, 29.3, 31.3, 36.0, 36.3, 40.3, 44.4, 45.6, 55.7, 56.4, 71.1, 113.1, 120.9, 121.4, 124.1, 126.0, 135.2, 146.1, 153.3, 167.2; HRMS (ESI⁺) calcd for C27H40NOS2 [M+H]⁺ 458.2546, found 458.2578.

Example 4

2-(2-{(1R,3aS,7aR,E)-1-[(R)-6-Hydroxy-6-methyl-heptan-2-yl]-7a-methyloctahydro-4H-inden-4-ylidene}ethyl)isoindoline-1,3-dione (16 KK-027)

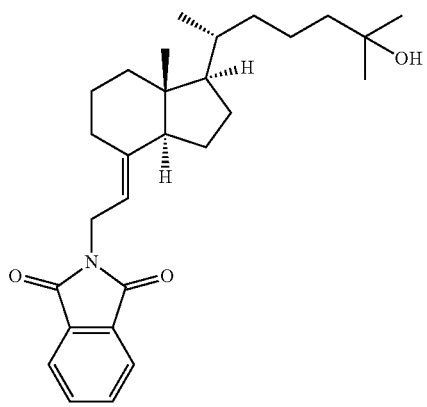

16 KK-027

To a solution of phthalimide (69.6 mg, 0.473 mmol), Ph₃P (29.9 mg, 0.473 mmol), and 8 (100.0 mg, 0.237 mmol) in THF (5 mL) was added diisopropyl azodicarboxylate (249 μL, 1.9 M in toluene, 0.473 mmol) at 0° C., and the mixture was stirred at the room temperature for 10 min. After the reaction was quenched with H₂O, the mixture was extracted with EtOAc three times, washed with brine, dried over Na₂SO₄, filtered, and concentrated. The residue was roughly purified by flash column chromatography on silica gel (hexane:EtOAc=6:1) to obtain the crude phthalimide product.

p-Toluenesulfonic acid monohydrate (113.1 mg, 0.595 mmol) was added to a solution of the above crude phthalimide in MeOH (10 mL). The mixture was stirred at room temperature for 30 min under air. After the reaction was quenched with H₂O and saturated aqueous NaHCO₃ at room temperature, the mixture was extracted with EtOAc three times, dried over Na₂SO₄, filtered, and concentrated. The residue was purified by flash column chromatography on silica gel (EtOAc only) to obtain 16 KK-027 (57.8 mg, 56% 2 steps) as a colorless oil.

16 KK-027: $[\alpha]_D^{27}$+44.7 (c 0.98, CHCl₃); IR (neat) 3394, 1715, 1394, 1088, 941, 724 cm⁻¹; ¹H NMR (600 MHz, CDCl₃) δ 0.49 (s, 3H), 0.92 (d, J=6.6 Hz, 3H), 0.99-1.05 (m, 1H), 1.17-1.64 (m, 19H), 1.66-1.71 (m, 2H), 1.80-1.86 (m, 1H), 1.92 (t, J=9.6 Hz, 1H), 1.92 (dt, J=3.0, 11.4 Hz, 1H), 2.91-2.95 (m, 1H), 4.27-4.37 (m, 2H), 5.20 (t, J=7.2 Hz, 1H), 7.67-7.70 (m, H), 7.81-7.84 (m, 2H); 13C NMR (100 MHz, CDCl₃) δ 11.8, 18.8, 20.8, 22.1, 23.4, 27.6, 28.8, 29.2, 29.3, 35.1, 36.0, 36.3, 40.3, 44.4, 45.4, 55.6, 56.4, 71.1, 113.7, 123.1, 132.3, 133.7, 144.5, 168.1; HRMS (ESI⁺) calcd for C₂₈H₃₉NO₃Na [M+Na]⁺ 460.2822, found 460.2850.

Example 5

2-({2-[(1R,3aS,7aR,E)-7a-methyl-1-{(R)-6-methyl-6-[(triethylsilyl)oxy]heptan-2-yl}octahydro-4H-inden-4-ylidene]ethyl}sulfonyl)benzo[d]thiazole (A)

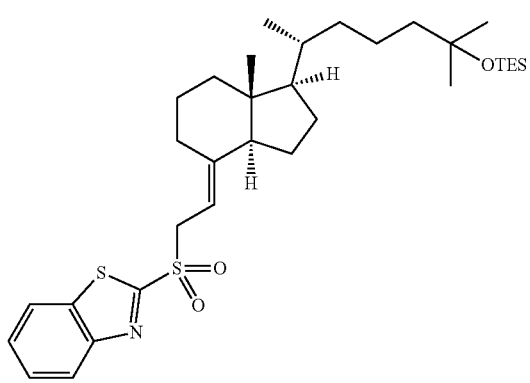

compound A

3-Deoxy-25-hydroxy-19-norvitamin D3 (14 KK-024)

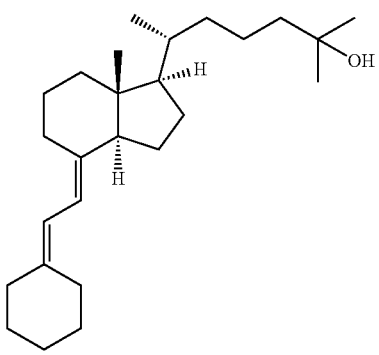

14 KK-024

LHMDS (332 μL, 1.0 M THF solution, 0.332 mmol) was added to the solution of CD-ring sulfone A (99.1 mg, 0.164 mmol) in THF (2 mL) at −78° C. After stirring for 30 min, the solution of cyclohexanone (48.8 mg, 50 μL, 0.497 mmol) was added to the reaction mixture, and the mixture was stirred at −78° C. for 30 min. After the reaction was quenched with H₂O at the same temperature, the mixture was extracted with EtOAc three times, dried over Na₂SO₄, filtered, and concentrated. The residue was purified by flash column chromatography on silica gel (hexane only) to obtain the crude coupling product (41.5 mg), and it was used for the next reaction without further purification. Tetrabutylammonium fluoride (497 µL, 1 M THF solution, 0.497 mmol) was added to the solution of the above crude coupling product (41.5 mg) in THF (5 mL), and the mixture was stirred at room temperature for 24 h. After the reaction was quenched with $H_2O$ and saturated aqueous $NH_4Cl$ at room temperature, the mixture was extracted with EtOAc three times, dried over $Na_2SO_4$, filtered, and concentrated. The residue was purified by flash column chromatography on silica gel (hexane:EtOAc=5:1) to obtain 14 KK-024 (30.9 mg, 50%, 2 steps) as a colorless oil.

14 KK-024: $[\alpha]_D^2$ 7 +64.3 (c 2.06, $CHCl_3$); IR (neat) 3368, 1445, 1376, 1215, 1148, 863, 759 cm-1; $^1H$ NMR (600 MHz, $CDCl_3$) δ 0.55 (s, 3H), 0.94 (d, J=7.2 Hz, 3H), 1.03-1.08 (m, 1H), 1.20-1.67 (m, 23H), 1.86-1.92 (m, 1H), 1.97-2.01 (m, 2H), 2.13-2.24 (m, 3H), 2.33-2.35 (m, 1H), 2.78-2.82 (m, 1H), 5.84 (d, J=12.0 Hz, 1H), 6.06 (d, J=12.0 Hz, 1H); $^{13}C$ NMR (150 MHz, $CDCl_3$) δ 12.1, 198.8, 20.8, 22.3, 23.4, 26.9, 27.6, 27.7, 28.6, 28.7, 28.9, 29.2, 29.3, 36.1, 36.4, 37.6, 40.6, 44.4, 45.6, 56.3, 56.5, 71.1, 115.7, 117.3, 140.4, 140.6; HRMS (ESI⁻) calcd for $C_{26}H_{43}O$ [M−H]⁻ 371.3308, found 371.3310.

Example 6

(R)-2-Methyl-6-[(1R,3aS,7aR,E)-7a-methyl-4-(prop-2-yn-1-ylidene)octahydro-1H-inden-1-yl]heptan-2-ol (13 KK-030)

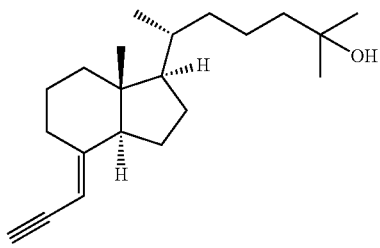

13 KK-030

To the solution of 8 (522.4 mg, 1.24 mmol) in $CH_2Cl_2$ (10 mL) were added 4-methylmorpholine N-oxide (290.5 mg, 2.48 mmol) and 4 Å molecular sieves (100 mg), cooled to 0° C. To the mixture was added TPAP (130.3 mg, 0.37 mmol) and stirred at 0° C. for 1 h. The reaction was diluted with excess amount of $Et_2O$. The mixture was filtered with celite and concentrated. The residue was purified by flash column chromatography on silica gel (hexane:EtOAc=10:1) to obtain the crude aldehyde (439.2 mg), and this was used for the next reaction without further purification. To the solution of the trimethylsilyl diazomethane (71 µL, 2.0 M in diethylether, 0.143 mmol) in THF (2 mL) was added n-BuLi (82 µL, 1.65 M in hexane, 0.135 mmol) at −78° C. and stirred at the same temperature for 15 min. To the mixture was added the crude CD aldehyde above (30 mg) in THF (2 mL) and stirred at the same temperature for 30 min. After the reaction was quenched with $H_2O$ and saturated aqueous $NH_4Cl$ at −78° C., the mixture was extracted with EtOAc twice, dried over $Na_2SO_4$, filtered, and concentrated. The residue was purified by flash column chromatography on silica gel (hexane:EtOAc=50:1) to obtain the crude CD-alkyne (22.2 mg).

p-Toluenesulfonic acid monohydrate (27.0 mg, 0.142 mmol) was added to a solution of the crude CD-alkyne (30.0 mg) in MeOH (3 mL). The mixture was stirred at room temperature under air for 10 min. After the reaction was quenched with $H_2O$ and saturated aqueous $NaHCO_3$ at room temperature, the mixture was extracted with EtOAc three times, washed with brine, dried over $Na_2SO_4$, filtered, and concentrated. The residue was purified on a preparative silica gel TLC plate (hexane:EtOAc=4:1) to obtain 13 KK-030 (19.7 mg, 58% 3 steps) as a colorless oil.

13 KK-030: $[\alpha]_D^{27}$+147.1 (c 1.52, $CHCl_3$); IR (neat) 3381, 3310, 2360, 2341, 1627, 1470, 1378, 1214, 1149, 911, 735 cm-1; $^1H$ NMR (600 MHz, $CDCl_3$) δ 0.55 (s, 3H), 0.93 (d, J=6.0 Hz, 3H), 1.02-1.08 (m, 1H), 1.18-1.63 (m, 17H), 1.67-1.72 (m, 1H), 1.75-1.80 (m, 1H), 1.84-1.93 (m, 1H), 2.00-2.04 (m, 1H), 2.96-2.99 (m, 2H), 5.05-5.06 (m, 1H); $^{13}C$ NMR (150 MHz, $CDCl_3$) δ 11.9, 18.7, 20.8, 21.9, 23.3, 27.6, 29.2, 29.4, 31.4, 36.0, 36.3, 40.0, 44.4, 46.3, 55.7, 56.4, 71.1, 79.3, 81.6, 99.3, 157.9; HRMS (ESI⁺) calcd for $C_{21}H_{32}$ [M-OH]+285.2577, found 285.2571.

Example 7

(R)-6-[(1R,3aS,7aR,E)-4-(ortho-Carboranylmethylidene)-7a-methyloctahydro-1H-inden-1-yl]-2-methylheptan-2-ol (17 KK-031)

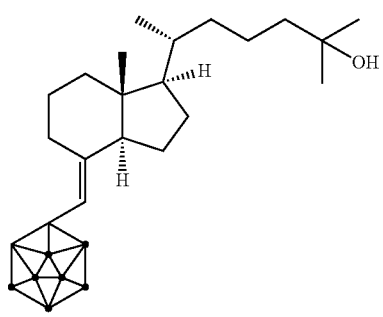

17 KK-031

To the solution of 8 (522.4 mg, 1.24 mmol) in $CH_2Cl_2$ (10 mL) were added 4-methylmorpholine N-oxide (290.5 mg, 2.48 mmol) and 4 Å molecular sieves (100 mg), cooled to 0° C. To the mixture was added TPAP (130.3 mg, 0.37 mmol) and stirred at 0° C. for 1 h. The reaction was diluted with excess amount of $Et_2O$. The mixture was filtered with celite and concentrated. The residue was purified by flash column chromatography on silica gel (hexane:EtOAc=10:1) to obtain the crude aldehyde (439.2 mg), and this was used for the next reaction without further purification. To the solution of the trimethylsilyl diazomethane (71 µL, 2.0 M in diethylether, 0.143 mmol) in THF (2 mL) was added n-BuLi (82 µL, 1.65 M in hexane, 0.135 mmol) at −78° C. and stirred at the same temperature for 15 min. To the mixture was added the crude CD aldehyde above (30 mg) in THF (2 mL) and stirred at the same temperature for 30 min. After the reaction was quenched with $H_2O$ and saturated aqueous $NH_4Cl$ at −78° C., the mixture was extracted with EtOAc twice, dried over $Na_2SO_4$, filtered, and concentrated. The residue was purified by flash column chromatography on silica gel (hexane:EtOAc=50:1) to obtain the crude CD-alkyne (22.2 mg).

To a solution of N,N-dimethylaniline (93.2 mg, 97 μL, 0.769 mmol) and the above crude CD-alkyne (51.1 mg) in toluene (5 mL) was added $B_{10}H_{14}$ (43.3 mg, 0.356 mmol) at room temperature, and the mixture was stirred at 100° C. for 15 min. The mixture was concentrated in vacuo, and the residue was purified by flash column chromatography on silica gel (hexane only-hexane:EtOAc=20:1) and followed by purification by flash column chromatography on silica gel (hexane:EtOAc=100:1) to obtain the crude product (20.0 mg)

p-Toluenesulfonic acid monohydrate (14.1 mg, 0.074 mmol) was added to a solution of the above crude product in MeOH (3 mL). The mixture was stirred at room temperature for 10 min under air. After the reaction was quenched with $H_2O$ and saturated aqueous $NaHCO_3$ at room temperature, the mixture was extracted with EtOAc three times, dried over $Na_2SO_4$, filtered, and concentrated. The residue was purified by flash column chromatography on silica gel (hexane:EtOAc=5:1) to obtain 17 KK-031 (13.1 mg, 16%, 4 steps) as a colorless oil.

17 KK-031: $[\alpha]_D^{27}$+117.4 (c 1.01, $CHCl_3$); IR (neat) 3463, 2602, 2565, 1467, 1440, 1376, 1208, 1128, 1072, 1020, 931, 721 cm-1; $^1H$ NMR (600 MHz, $CDCl_3$) δ 0.50 (s, 3H), 0.55-0.62 (m, 1H), 0.92-2.82 (m, 38H), 3.20 (d, J=13.2 Hz, 3H), 3.64 (brs, 1H), 5.09 (s, 1H); $^{13}C$ NMR (150 MHz, $CDCl_3$) δ 11.7, 18.8, 20.7, 22.1, 23.4, 27.3, 29.0, 29.4, 35.9, 36.3, 40.0, 44.3, 46.8, 56.3, 56.6, 62.8, 71.0, 74.0, 114.9, 150.3; HRMS (ESI-) calcd for $C_{21}H_{43}OB_{10}$[M–H]- 421.4282, found 421.4321.

Example 8

(R)-6-{(1R,3aS,7aR,E)-4-[2-(Decylthio)ethylidene]-7a-methyloctahydro-1H-inden-1-yl}-2-methylheptan-2-ol (33 KK-032)

To the solution of 11 KK-025 (96.5 mg, 0.312 mmol) and pyridine (153.5 mg, 157 μL, 1.94 mmol) in $CCl_4$ (15 mL) and $CH_2Cl_2$ (15 mL) was added tri-n-butylphosphine (263.0 mg, 320 μL, 1.30 mmol) at 0° C., and the mixture was stirred at the same temperature for 15 min. After the reaction was diluted with hexane, the mixture was filtered, and concentrated. The residue was roughly purified by flash column chromatography on silica gel (hexane:EtOAc=5:1) to obtain a crude chloride. The crude allylchloride was used for the next reaction without further purification. To the solution of the above crude allylchloride, $K_2CO_3$ (61.6 mg, 0.446 mmol), and KI (37.0 mg, 0.223 mmol) in DMF (4 mL) and $CH_2Cl_2$ (15 mL) was added decanethiol (388.8 mg, 423 μL, 2.23 mmol) at room temperature under air, and the mixture was stirred at the same temperature for 190 min. After the reaction was quenched with $H_2O$ and saturated aqueous $NH_4Cl$, the mixture was extracted with EtOAc three times, washed with brine, dried over $Na_2SO_4$. The residue was purified by flash column chromatography on silica gel (hexane:EtOAc=5:1) to obtain 33 KK-032 (80.8 mg, 78%, 2 steps) as a colorless oil.

33 KK-032: $[\alpha]_D^{27}$+89.6 (c 2.19, $CHCl_3$); IR (neat) 3370, 1467, 1377, 1217, 1148 cm-1; $^1H$ NMR (600 MHz, $CDCl_3$) δ 0.56 (s, 3H), 0.88 (t, J=7.2 Hz, 3H), 0.94 (d, J=7.2 Hz, 3H), 1.02-1.08 (m, 1H), 1.21-1.68 (m, 37H), 1.83-2.01 (m, 3H), 2.45 (t, J=7.8 Hz, 3H), 2.57-2.61 (m, 1H), 3.15 (dd, J=7.8, 13.2 Hz, 1H), 3.24 (dd, J=8.4, 13.2 Hz, 1H), 5.02 (t, J=8.4 Hz, 1H); $^{13}C$ NMR (150 MHz, $CDCl_3$) δ 11.8, 14.1, 18.8, 20.8, 22.2, 22.7, 23.5, 27.6, 28.5, 28.6, 29.0, 29.2, 29.3, 29.3, 29.5, 29.5, 29.7, 31.0, 31.9, 36.1, 36.4, 40.4, 44.4, 45.1, 55.7, 56.5, 71.1, 116.4, 142.3; HRMS (ESI+) calcd for $C_{30}H_{56}O_3SNa$ [M+Na]+ 487.3944, found 487.3965.

Examples 9 and 10

R)-6-{(1R,3aS,7aR,E)-4-[2-(2H-Tetrazol-2-yl)ethylidene]-7a-methyl octahydro-1H-inden-1-yl}-2-methylheptan-2-ol (22 KK-029)

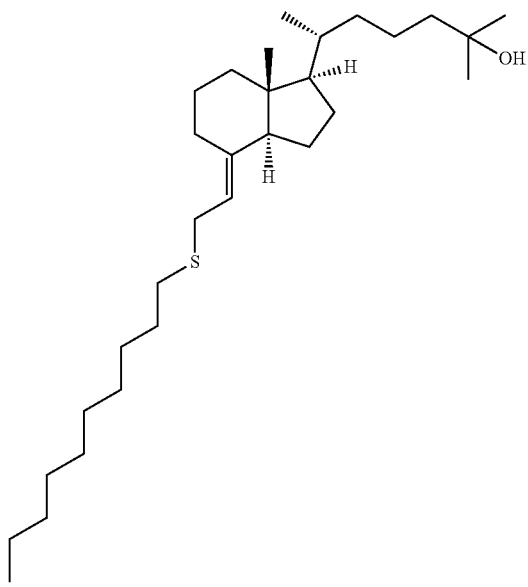

33 KK-032

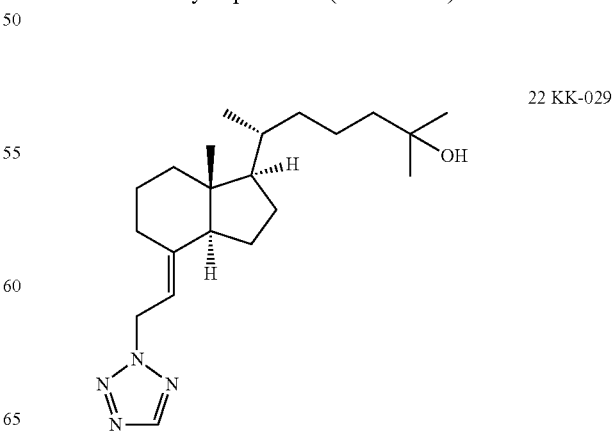

22 KK-029

(R)-6-{(1R,3aS,7aR,E)-4-[2-(1H-Tetrazol-1-yl)ethylidene]-7a-methyloctahydro-1H-inden-1-yl}-2-methylheptan-2-ol (21 KK-028)

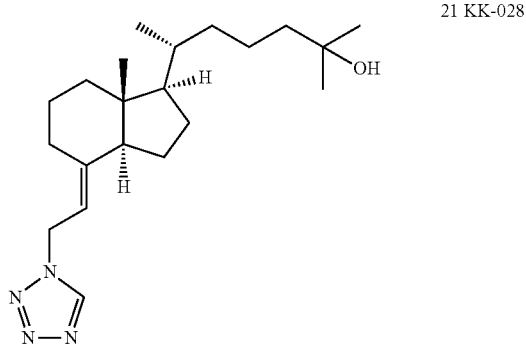 [SMILES: C[C@H](CCCC(C)(C)O)[C@H]1CC[C@H]2/C(=C/Cn3cnnn3)CCC[C@]12C]

21 KK-028

To a solution of 1H-tetrazole (45.4 mg, 0.649 mmol), Ph₃P (206.4 mg, 9.72 mmol), and 11 KK-025 (100 mg, 0.324 mmol) in THF (5 mL) was added diisopropyl azodicarboxylate (512 L, 1.9 M in toluene, 9.72 mmol) at 0° C., and the mixture was stirred at room temperature for 1 h. After the reaction was quenched with H₂O at 0° C., the mixture was extracted with EtOAc three times, washed with brine, dried over Na₂SO₄, filtered, and concentrated. The residue was purified by flash column chromatography on silica gel (hexane:EtOAc=2:1-EtOAc only) to obtain the less polar product 22 KK-029 (43.2 mg, 37%) and the more polar product 21 KK-028 (38.8 mg, 33%) each as a colorless oil.

22 KK-029: $[\alpha]_D^{27}$ +53.6 (c 1.31, CHCl₃); IR (neat) 3427, 1468, 1454, 1376, 1282, 1027, 911, 736 cm-1; ¹H NMR (600 MHz, CDCl3) δ 0.50 (s, 3H), 0.92 (d, J=6.6 Hz, 3H), 1.01-1.06 (m, 1H), 1.20-2.02 (m, 24H), 2.77-2.80 (m, 1H), 5.23-5.32 (m, 3H), 8.47 (s, 1H); 13C NMR (150 MHz, CDCl3) δ 11.8, 18.8, 20.8, 22.0, 23.3, 27.5, 28.0, 29.2, 29.4, 36.0, 36.3, 40.1, 44.3, 45.8, 50.1, 55.6, 56.4, 71.0, 111.4, 148.1, 152.8; HRMS (ESI⁺) calcd for C₂₁H₃₆N₄ONa [M+Na]⁺ 383.2781, found 383.2793.

21 KK-028: $[\alpha]_D^{27}$ +64.5 (c 0.62, CHCl₃); IR (neat) 3400, 1468, 1445, 1376, 1162, 1101, 912, 734, 661 cm-1; ¹H NMR (400 MHz, CDCl₃) δ 0.55 (s, 3H), 0.94 (d, J=6.4 Hz, 3H), 1.01-1.09 (m, 1H), 1.20-1.61 (m, 18H), 1.72-1.82 (m, 2H), 1.86-1.94 (m, 1H), 2.01-2.08 (m, 3H), 2.65-2.70 (m, 1H), 5.03-5.12 (m, 1H), 5.23 (t, J=7.3 Hz, 1H), 8.53 (s, 1H); ¹³C NMR (100 MHz, CDCl₃) δ 11.9, 18.8, 20.8, 22.1, 23.3, 27.5, 28.9, 29.2, 29.4, 36.0, 36.3, 40.0, 44.3, 45.3, 45.8, 55.6, 56.4, 71.1, 110.9, 151.8, 149.4; HRMS (ESI+) calcd for C₂₁H₃₆N₄ONa [M+Na]⁺ 383.2781, found 383.2789.

Examples 11 and 12

(R)-2-Methyl-6-{(1R,3aS,7aR,E)-7a-methyl-4-[2-(5-phenyl-2H-tetrazol-2-yl)ethylidene]octahydro-1H-inden-1-yl}heptan-2-ol (23 KK-039)

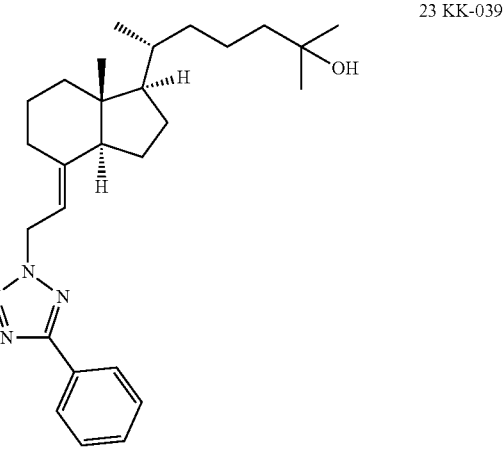

23 KK-039

(R)-2-Methyl-6-{(1R,3aS,7aR,E)-7a-methyl-4-[2-(5-phenyl-1H-tetrazol-1-yl)ethylidene]octahydro-1H-inden 1-yl}heptan-2-ol (24 KK-045)

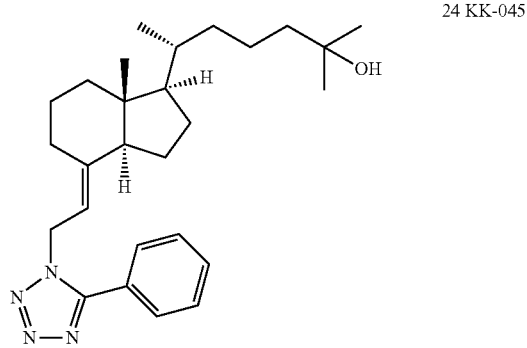 [SMILES: C[C@H](CCCC(C)(C)O)[C@H]1CC[C@H]2/C(=C/Cn3nnnc3-c3ccccc3)CCC[C@]12C]

24 KK-045

To a solution of 5-phenyl-1H-tetrazole (311.3 mg, 2.13 mmol), Ph₃P (372.5 mg, 1.42 mmol), and 8 (305.3 mg, 0.722 mmol) in THF (10 ml) was added diisopropyl azodicarboxylate (1.12 mL, 1.9 M in toluene, 2.13 mmol) at 0° C., and the mixture was stirred at the same temperature for 3 h. After the reaction was quenched with H₂O at 0° C., the mixture was extracted with EtOAc three times, washed with brine, dried over Na 2SO4, filtered, and concentrated. The residue was roughly purified by flash column chromatography on silica gel (hexane:EtOAc=3:1) to obtain the crude products (less polar and more polar products).

p-Toluenesulfonic acid monohydrate (285.3 mg, 1.50 mmol) was added to a solution of the above less polar crude product in MeOH (10 mL). The mixture was stirred at room temperature for 40 min under air. After the reaction was quenched with H₂O and saturated aqueous NaHCO₃ at room temperature, the mixture was extracted with EtOAc three times, dried over Na₂SO₄, filtered, and concentrated. The residue was purified by flash column chromatography on silica gel (hexane:EtOAc=1:1) to obtain 23 KK-039 (187.8 mg, 60%) as a colorless oil.

23 KK-039: $[\alpha]_D^{27}$+41.2 (c 1.33, CHCl$_3$); IR (neat) 3419, 1467, 1450, 1378, 1216, 761, 694 cm-1; $^1$H NMR (400 MHz, CDCl$_3$) δ 0.54 (s, 3H), 0.94 (d, J=6.4 Hz, 3H), 1.00-1.10 (m, 1H), 1.19-2.05 (m, 24H), 2.83-2.86 (m, 1H), 5.29-5.36 (m, 3H), 7.43-7.52 (m, 3H), 8.12-8.15 (m, 2H); $^{13}$C NMR (100 MHz, CDCl$_3$) δ 11.8, 18.8, 20.8, 22.0, 23.4, 27.6, 29.1, 29.2, 29.4, 36.0, 36.3, 40.2, 44.4, 45.9, 50.2, 55.7, 56.5, 71.1, 111.6, 126.8, 127.6, 128.8, 130.1, 148.0, 165.0; HRMS (ESI$^+$) calcd for C$_{27}$H$_{40}$N$_4$ONa [M+Na]$^+$ 459.3094, found 459.3079.

p-Toluenesulfonic acid monohydrate (190.2 mg, 1.0 mmol) was added to a solution of the above more polar crude product in MeOH (10 mL). The mixture was stirred at room temperature for 40 min under air. After the reaction was quenched with H$_2$O and saturated aqueous NaHCO$_3$ at room temperature, the mixture was extracted with EtOAc three times, dried over Na$_2$SO$_4$, filtered, and concentrated. The residue was purified on a preparative silica gel TLC plate (hexane:EtOAc=1:1) to obtain 24 KK-045 (48.4 mg, 15%) as a colorless oil.

24 KK-045: $[\alpha]_D^{27}$+67.2 (c 0.09, CHCl$_3$); IR (neat) 3425, 1471, 1377, 1219, 758, 698 cm$^{-1}$; 1H NMR (400 MHz, CDCl$_3$) δ 0.46 (s, 3H), 0.92 (d, J=6.4 Hz, 3H), 1.00-1.07 (m, 1H), 1.21-1.72 (m, 21H), 1.82-2.01 (m, 3H), 2.51-2.56 (m, 1H), 5.07-5.17 (m, 3H), 7.52-7.60 (m, 3H), 7.68-7.71 (m, 2H); $^{13}$C NMR (100 MHz, CDCl$_3$) δ 11.8, 18.8, 20.8, 22.1, 23.1, 27.5, 28.9, 29.2, 29.4, 36.0, 36.3, 40.0, 44.3, 45.6, 45.7, 55.52, 56.4, 71.1, 112.9, 124.2, 128.8, 129.1, 131.1, 146.5, 154.1; HRMS (ESI$^+$) calcd for C$_{27}$H$_{40}$N$_4$ONa [M+Na]$^+$ 459.3094, found 459.3093.

Example 13

(R)-6-{(1R,3aS,7aR,E)-4-[2-(Decylamino)ethylidene]-7a-methyloctahydro-1H-inden-1-yl}-2-methylheptan-2-ol (32 KK-040)

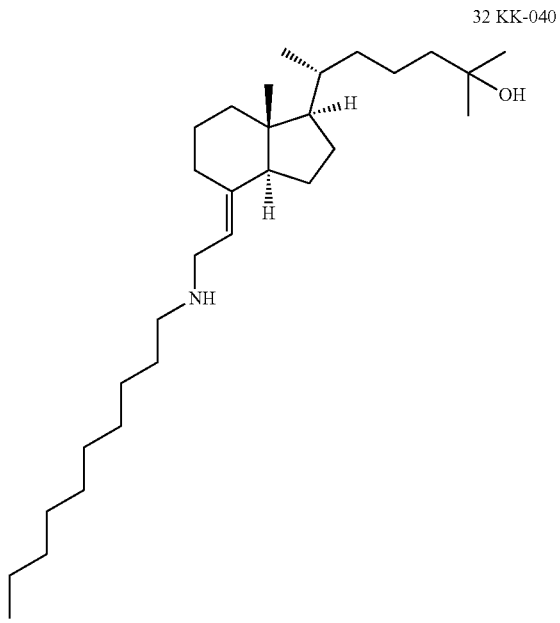 [SMILES: CCCCCCCCCCNC/C=C1\CCC[C@]2(C)[C@@H]([C@H](C)CCCC(C)(C)O)CC[C@@H]12]

32 KK-040

PDC (222.5 mg, 0.591 mmol) was added to the solution of 8 (100.0 mg, 0.237 mmol) in CH$_2$Cl$_2$ (4 mL) at room temperature, and the mixture was stirred at the same temperature under air for 4 h. The solution was diluted with Et$_2$O, filtered through a celite pad, and concentrated. To the solution of the obtained crude aldehyde above and 1-aminodecane (184.6 mg, 233 μL, 1.19 mmol) in CH$_2$Cl$_2$ (5 mL) was added anhydrous MgSO$_4$ (1 g) at room temperature under air. The mixture was stirred for 1 h and refluxed for 1 h. After the reaction was quenched with H$_2$O, the mixture was extracted with EtOAc three times, dried over Na$_2$SO$_4$, filtered, and concentrated. The obtained crude imine was used for the next reaction without further purification. To the solution of the obtained crude imine above in MeOH (10 mL) was added NaBH$_4$ (26.9 mg, 0.711 mmol) at 0° C. The mixture was stirred at the same temperature under air for 45 min. After the reaction was quenched with H$_2$O and saturated aqueous NH$_4$Cl, the mixture was extracted with EtOAc three times, dried over Na$_2$SO$_4$, filtered, and concentrated. The obtained crude amine was used for the next reaction without further purification.

p-Toluenesulfonic acid monohydrate (225.4 mg, 1.19 mmol) was added to a solution of the above crude amine in MeOH (10 mL). The mixture was stirred at room temperature for 20 min. After the reaction was quenched with 3 M aqueous NaOH solution, and stirred for 15 min. The mixture was extracted with CH$_2$Cl$_2$ four times, dried over Na$_2$SO$_4$, filtered, and concentrated. The residue was purified by flash column chromatography on silica gel (EtOAc:MeOH=7:1, 1% Et3N) to obtain 32 KK-040 (64.5 mg, 61% 4 steps) as a colorless oil.

32 KK-040: $[\alpha]_D^{27}$+54.0 (c 1.38, CHCl$_3$); IR (neat) 3358, 1467, 1215 cm-1; $^1$H NMR (600 MHz, CDCl$_3$) δ 0.53 (s, 3H), 0.86 (t, J=6.9 Hz, 3H), 0.92 (d, J=6.6 Hz, 3H), 1.06-1.65 (m, 39H), 1.80-1.98 (m, 3H), 2.53-2.61 (m, 3H), 3.23-3.29 (m, 2H), 5.02 (t, J=6.9 Hz, 1H); $^{13}$C NMR (150 MHz, CDCl$_3$) δ 11.8, 14.1, 18.8, 20.8, 22.2, 22.6, 23.4, 27.4, 27.6, 28.7, 29.1, 29.3, 29.3, 29.5, 29.5, 29.9, 31.9, 36.1, 36.4, 40.4, 44.4, 45.1, 46.2, 49.3, 55.6, 56.5, 70.9, 118.4, 141.6; HRMS (ESI$^+$) calcd for C$_{30}$H$_{58}$ON [M+H]$^+$ 448.4513, found 448.4550.

Example 14

(R)-6-{(1R,3aS,7aR,E)-4-[2-(tert-Butylamino)ethylidene]-7a-methyloctahydro-1H-inden-1-yl}-2-methylheptan-2-ol (12)

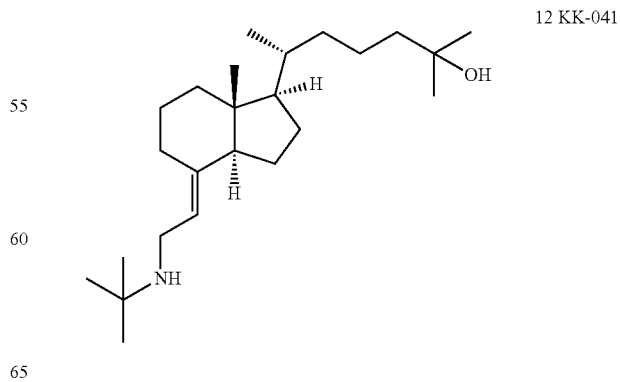

12 KK-041

PDC (127.9 mg, 0.34 mmol) was added to the solution of 8 (99.5 mg, 0.225 mmol) in CH$_2$Cl$_2$ (4 mL) and DMF (0.5 mL) at room temperature, and the mixture was stirred at the same temperature under air for 2 h. The solution was diluted with Et$_2$O, filtered through a celite pad, and concentrated. To the solution of the obtained crude aldehyde above and tert-butylamine (99.4 mg, 143 μL, 1.36 mmol) in CH$_2$Cl$_2$ (5 mL) was added anhydrous MgSO$_4$ (1 g) at room temperature under air. The mixture was stirred for 70 min and refluxed overnight. After the reaction was quenched with H$_2$O, the mixture was extracted with EtOAc three times, dried over Na$_2$SO$_4$, filtered, and concentrated. The obtained crude imine was used for the next reaction without further purification. To the solution of the above crude imine in MeOH (3 mL) was added NaBH$_4$ (5.1 mg, 0.136 mmol) at 0° C. The mixture was stirred at the same temperature under air for 1 h. After the reaction was quenched with H$_2$O and saturated aqueous NH$_4$Cl, the mixture was extracted with EtOAc three times, dried over Na$_2$SO$_4$, filtered, and concentrated. The obtained crude amine was used for the next reaction without further purification.

p-Toluenesulfonic acid monohydrate (129.3 mg, 0.68 mmol) was added to a solution of the above crude amine in MeOH (10 mL). The mixture was stirred at room temperature under air for 20 min. After the reaction was quenched with H$_2$O, the mixture was extracted with CH$_2$Cl2 three times, dried over Na$_2$SO$_4$, filtered, and concentrated. The residue was diluted with MeOH (3 mL) and 1 M aqueous NaOH (3 mL) and stirred for 10 min. To the mixture was added H$_2$O, and extracted with CH$_2$Cl$_2$ four times, dried over Na$_2$SO$_4$, filtered, and concentrated. The residue was purified by flash column chromatography on silica gel (EtOAc only 1% Et$_3$N) to obtain 12 (76.2 mg, 93%, 4 steps) as a colorless oil.

12: $[\alpha]_D^{27}$+63.0 (c 0.44, CHCl$_3$); IR (neat) 3365, 1470, 1377, 1363, 1215 cm-1; $^1$H NMR (400 MHz, CDCl$_3$) δ 0.54 (s, 3H), 0.93 (d, J=6.4 Hz, 3H), 0.98-2.00 (m, 35H), 2.55-2.59 (m, 1H), 3.21-3.30 (m, 2H), 5.08 (t, J=6.7 Hz, 1H), 6.62-6.64 (m, 2H), 6.69-6.72 (m, 1H), 7.15-7.20 (m, 2H); $^{13}$C NMR (100 MHz, CDCl$_3$) δ 11.9, 18.8, 20.8, 22.2, 23.4, 27.7, 28.7, 28.8, 29.2, 29.3, 36.1, 36.4, 39.4, 40.4, 44.4, 45.2, 50.8, 55.7, 56.5, 71.1, 118.6, 141.5; HRMS (ESI$^+$) calcd for C$_{24}$H$_{46}$ON [M+H]$^+$ 364.3574, found 364.3603.

Example 15

(R)-2-Methyl-6-{(1R,3aS,7aR,E)-7a-methyl-4-[2-(phenylamino)ethylidene]octahydro-1H-inden-1-yl}heptan-2-ol (18 KK-042)

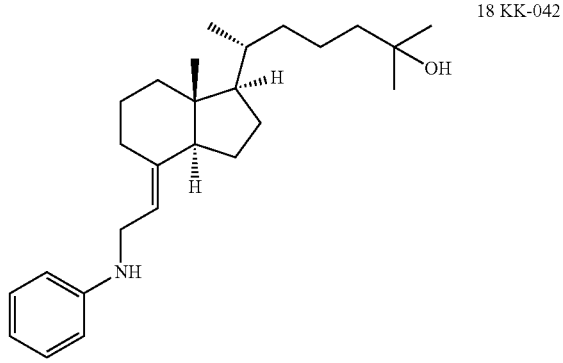 [SMILES: C[C@H](CCCC(C)(C)O)[C@H]1CC[C@H]2/C(=C/CNc3ccccc3)CCC[C@]12C]

18 KK-042

PDC (333.8 mg, 0.887 mmol) was added to the solution of 8 (151.7 mg, 0.359 mmol) in CH$_2$Cl$_2$ (6 mL) at room temperature, and the mixture was stirred at the same temperature under air for 3 h. The solution was diluted with Et$_2$O, filtered through a celite pad, and concentrated to obtain the crude aldehyde. To the solution of the above crude aldehyde and aniline (330.6 mg, 324 μL, 3.55 mmol) in CH$_2$Cl$_2$ (10 mL) was added anhydrous MgSO$_4$ (Ig) at room temperature under air. The mixture was stirred for 90 min and refluxed for 40 min. After the reaction was quenched with H$_2$O, the mixture was extracted with CH$_2$Cl$_2$ three times, dried over Na$_2$SO$_4$, filtered, and concentrated. The obtained crude imine was used for the next reaction without further purification. To the solution of the above crude imine in MeOH (10 mL) was added NaBH$_4$ (40.2 mg, 1.07 mmol) at 0° C. The mixture was stirred at the same temperature under air for 30 min. After the reaction was quenched with H$_2$O and saturated aqueous NH$_4$Cl, the mixture was extracted with EtOAc three times, dried over Na$_2$SO$_4$, filtered, and concentrated. The obtained crude amine was used for the next reaction without further purification. p-Toluenesulfonic acid monohydrate (2.7 g, 14.2 mmol) was added to a solution of the above crude amine in MeOH (10 mL). The mixture was stirred at room temperature under air for 45 min. After the reaction was quenched with 1 M aqueous NaOH solution, and stirred for a further 10 min. The mixture was extracted with CH$_2$Cl$_2$ three times, dried over Na$_2$SO$_4$, filtered, and concentrated. The residue was purified by flash column chromatography on silica gel (hexane:EtOAc=10:1-3:1) to obtain 18 KK-042 (88.6 mg, 65% 4 steps) as a colorless oil.

18 KK-042: $[a]_D^{27}$+67.9 (c 1.89, CHCl$_3$); IR (neat) 3368, 1603, 1505, 1469, 1377, 1318, 1248, 1216, 1151, 755, 692 cm-1; $^1$H NMR (400 MHz, CDCl$_3$) δ 0.56 (s, 3H), 0.95 (d, J=6.4 Hz, 3H), 1.03-1.10 (m, 1H), 1.18-1.72 (m, 22H), 1.84-2.06 (m, 3H), 2.65-2.69 (m, 1H), 3.71-3.81 (m, 2H), 5.01 (t, J=6.6 Hz, 1H), 6.62-6.64 (m, 2H), 6.69-6.72 (m, 1H), 7.157.20 (m, 2H); $^{13}$C NMR (100 MHz, CDCl$_3$) δ 11.8, 18.8, 20.8, 22.2, 23.4, 27.6, 28.8, 29.2, 29.3, 36.1, 36.4, 40.3, 41.3, 45.2, 55.6, 56.5, 71.1, 113.0, 117.1, 117.3, 129.1, 143.0, 148.4; HRMS (ESI$^+$) calcd for C$_{26}$H$_{42}$ON [M+H]$^+$ 384.3261, found 384.3258.

Example 16

2-[(1R,3aS,7aR,E)-7a-Methyl-1-{(R)-6-methyl-6-[(triethylsilyl)oxy]heptan-2-yl}octahydro-4H-inden-4-ylidene]acetic acid (B)

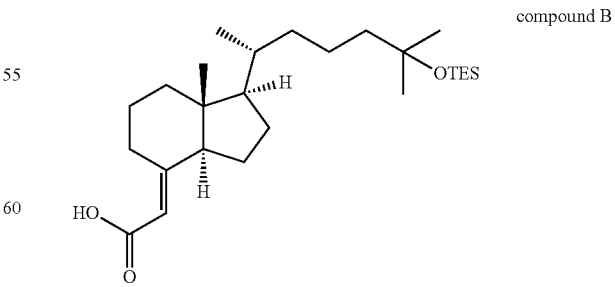

compound B

PDC (127.9 mg, 0.34 mmol) was added to the solution of 8 (103.9 mg, 0.246 mmol) in CH$_2$Cl$_2$ (4 mL) at room temperature, and the mixture was stirred at the same temperature under air for 3 h. The solution was diluted with Et₂O, filtered with celite, and concentrated to obtain the crude aldehyde.

To the mixture of the above crude aldehyde, NaH2PO4 (74.3 mg, 0.476 mmol), 30% H₂O₂ (72 tL) in H₂O (1 mL) and t-BuOH (3 mL) was added NaClO (24.6 mg, 0.272 mmol) at 0° C. under air and stirred at the same temperature for 5 min and at room temperature for 4 h. After the reaction was quenched with H₂O, the mixture was extracted with EtOAc three times, dried over Na₂SO₄, filtered, and concentrated. The residue was purified by flash column chromatography on silica gel (hexane:EtOAc=2:1) to obtain B (82.5 mg, 80%, 2 steps) as a colorless oil.

B: $[a]_D^{27}$+93.9 (c 1.54, CHCl₃); IR (neat) 3048, 1686, 1638, 1459, 1416, 1268, 1212, 1045, 735 cm-1; ¹H NMR (400 MHz, CDCl₃) δ 0.58 (s, 3H), 0.56 (q, J=7.8 Hz, 1H), 0.92-0.99 (m, 13H), 1.19-1.77 (m, 19H), 1.84-1.96 (m, 1H), 2.01-2.04 (m, 1H), 2.10-2.15 (m, 1H), 3.82-3.88 (m, 1H), 5.49 (s, 1H); ¹³C NMR (100 MHz, CDCl₃) δ 6.8, 7.1, 12.0, 18.7, 20.8, 22.1, 24.0, 27.4, 29.8, 29.9, 30.0, 35.9, 36.3, 40.1, 45.5, 47.4, 56.8, 57.1, 73.4, 111.3, 166.6, 172.0; HRMS (ESI⁺) calcd for C₂₈H₄₆O₃SiNa [M+Na]⁺ 481.3108, found 481.3065.

Example 17

2-{(1R,3 aS,7 aR,E)-1-[(R)-6-Hydroxy-6-methyl-heptan-2-yl]-7a-methyloctahydro-4H-inden-4-ylidene}-1-(piperidin-1-yl)ethan-1-one (19)

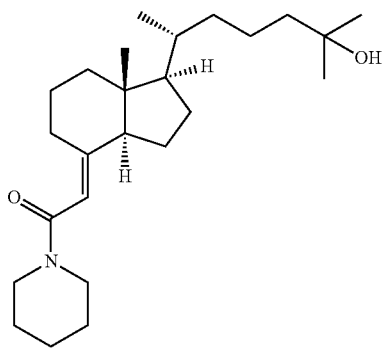

19 KK-043

To a solution of piperidine (24.1 mg, 28 µL, 0.283 mmol) and B (82.5 mg, 0.189 mmol) in DMF (3 mL) were added diisopropylethylamine (61.0 mg, 82 µL, 0.472 mmol) and BOP reagent (166.8 mg, 0.377 mmol) at 0° C., and the mixture was stirred at room temperature for 15 min. After the reaction was quenched with H₂O and saturated aqueous NH₄Cl at room temperature, the mixture was extracted with EtOAc three times, dried over Na₂SO₄, filtered, and concentrated to obtain the crude amide.

p-Toluenesulfonic acid monohydrate (179.4 mg, 0.943 mmol) was added to a solution of the above crude amide in MeOH (5 mL). The mixture was stirred at room temperature for 10 min under air. After the reaction was quenched with H₂O and saturated aqueous NaHCO₃ at room temperature, the mixture was extracted with EtOAc three times, dried over Na 2SO4, filtered, and concentrated. The residue was purified by flash column chromatography on silica gel (hexane:EtOAc=2:1-1:1) to obtain 19 KK-043 (57.3 mg, 73%, 2 steps) as a colorless oil.

19 KK-043: $[a]_D^{27}$+84.8 (c 0.96, CHCl₃); IR (neat) 3374, 1610, 1444, 1255, 753 cm-1; ¹H NMR (400 MHz, CDCl₃) δ 0.59 (s, 3H), 0.93 (d, J=6.4 Hz, 3H), 1.01-1.11 (m, 1H), 1.20-2.03 (m, 30H), 2.72-2.77 (m, 1H), 3.46-3.51 (m, 3H), 3.61 (brs, 1H), 5.51 (s, 1H); ¹³C NMR (100 MHz, CDCl₃) δ 12.1, 18.7, 20.7, 22.1, 23.3, 24.6, 25.8, 26.4, 27.5, 29.2, 29.3, 30.5, 36.0, 36.3, 40.0, 42.2, 44.3, 46.1, 47.5, 55.6, 56.4, 71.0, 114.8, 149.8, 167.7; HRMS (ESI⁺) calcd for C₂₅H₄₄NO₂ [M+H]⁺ 390.3367, found 390.3391.

Example 18

2-{(1R,3aS,7aR,E)-1-[(R)-6-Hydroxy-6-methylheptan-2-yl]-7a-methyloctahydro-4H-inden-4-ylidene}-1-morpholinoethan-1-one (20 KK-044)

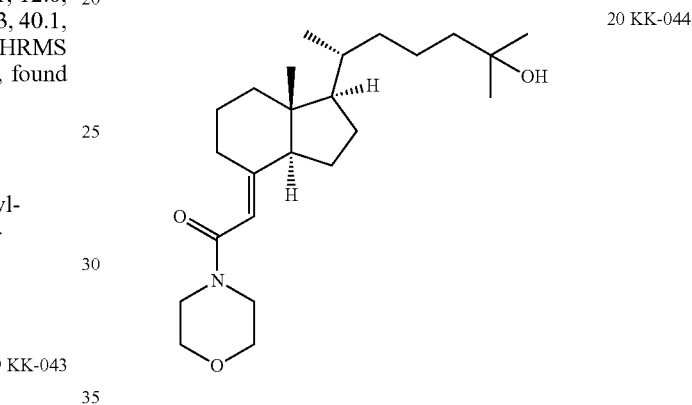

20 KK-044

To a solution of morpholine (32.0 mg, 32 µL, 0.367 mmol) and B (80.2 mg, 0.184 mmol) in DMF (3 mL) were added diisopropylethylamine (80 µL, 0.46 mmol) and BOP reagent (162.4 mg, 0.367 mmol) at 0° C., and the mixture was stirred at room temperature for 21 h. After the reaction was quenched with H₂O and saturated aqueous NH₄Cl at room temperature, the mixture was extracted with EtOAc three times, washed with brine, dried over Na₂SO₄, filtered, and concentrated to obtain the crude amide.

p-Toluenesulfonic acid monohydrate (175.0 mg, 0.92 mmol) was added to a solution of the above crude amide in MeOH (10 mL). The mixture was stirred at room temperature for 20 min under air. After the reaction was quenched with H₂O and saturated aqueous NaHCO₃ at room temperature, the mixture was extracted with EtOAc three times, dried over Na₂SO₄, filtered, and concentrated. The residue was purified by flash column chromatography on silica gel (hexane:EtOAc=1:1) to obtain 20 KK-044 (65.4 mg, 91%, 2 steps) as a colorless oil.

20 KK-044: $[\alpha]_D^{27}$+91.8 (c 1.14, CHCl₃); IR (neat) 3426, 1615, 1463, 1231, 1117, 851, 753 cm-1; ¹H NMR (600 MHz, CDCl₃) δ 0.59 (s, 3H), 0.94 (d, J=6.0 Hz, 3H), 1.03-1.11 (m, 1H), 1.21-1.62 (m, 19H), 1.69-1.71 (m, 1H), 1.76-1.81 (m, 1H), 1.88-1.92 (m, 1H), 2.01-2.06 (m, 2H), 2.83-2.85 (m, 1H), 3.52 (brs, 1H), 3.65-3.69 (m, 6H), 5.51 (s, 1H); ¹³C NMR (150 MHz, CDCl₃) δ 12.1, 18.7, 20.7, 22.1, 23.4, 27.4, 29.2, 29.4, 30.6, 36.0, 36.3, 39.9, 41.7, 44.3, 46.3, 46.9, 55.8, 56.4, 66.9, 71.0, 113.6, 152.3, 167.9; HRMS (ESI⁺) calcd for C24H41NO3Na [M+Na]⁺ 414.2979, found 414.2998.

Example 19

({(R)-6-[(1R,3aS,7aR,E)-4-(2-Azidoethylidene)-7a-methyloctahydro-1H-inden-1-yl]-2-methylheptan-2-yl}oxy)triethylsilane (9)

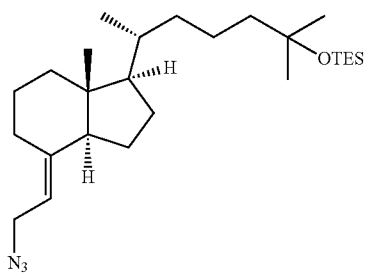

To the solution of 8 (300.0 mg, 0.71 mmol) and pyridine (337.0 mg, 344 µL, 4.26 mmol) in CCl$_4$ (30 mL) was added tri-n-butylphosphine (574.6 mg, 700 µL, 2.84 mmol) at 0° C., over 5 min, and the mixture was stirred at the same temperature for 15 min. After the reaction was diluted with hexane (50 mL), the mixture was filtered, and concentrated. The obtained crude allylchloride was used for the next reaction without further purification.

To the solution of the above crude allylchloride in DMF (15 mL) was added NaN3 (138.5 mg, 2.13 mmol) at room temperature, and the mixture was stirred at the same temperature for 20 min. After the reaction was quenched with H$_2$O, the mixture was extracted with EtOAc three times, washed with brine, dried over Na$_2$SO$_4$, filtered, and concentrated. The residue was purified by flash column chromatography on silica gel (hexane:EtOAc=30:1) to obtain 9 (273.1 mg, 86%, 2 steps) as a colorless oil.

9: $[a]_D^{27}$ 36.6 (c 1.61, CHCl$_3$); IR (neat) 2095, 1380, 1235, 1045, 743 cm-1; $^1$H NMR (600 MHz, CDCl$_3$) δ 0.57 (q, J=8.0 Hz, 1H), 0.59 (s, 1H), 0.93 (d, J=6.6 Hz, 1H), 0.95 (t, J=8.4 Hz, 1H), 0.99-1.06 (m, 1H), 1.19-1.55 (m, 20H), 1.67-1.71 (m, 2H), 1.86-1.94 (m, 1H), 2.00-2.05 (m, 2H), 2.60-2.62 (m, 1H), 3.73 (dd, J=6.6, 13.2 Hz, 1H), 3.89 (dd, J=7.8, 13.8 Hz, 1H), 5.13 (t, J=7.5 Hz, 1H); $^{13}$C NMR (150 MHz, CDCl$_3$) δ 6.9, 7.2, 11.9, 18.9, 20.9, 22.2, 23.9, 27.6, 28.9, 29.9, 30.1, 36.2, 36.5, 40.4, 45.2, 45.6, 47.5, 55.9, 56.7, 73.5, 112.7, 147.2; HRMS (ESI$^+$) calcd for C26H49N3OSi [M+Na]$^+$ 470.3537, found 470.3577.

Example 20

(R)-2-Methyl-6-{(1R,3aS,7aR,E)-7a-methyl-4-[2-(4-phenyl-1H-1,2,3-triazol-1-yl)ethylidene]octahydro-1H-inden-1-yl}heptan-2-ol (25 KK-034)

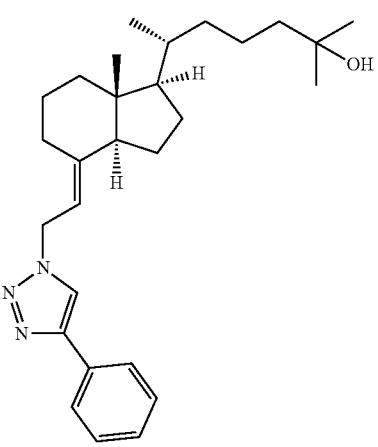

To a solution of phenylacetylene (56.9 mg, 24 µL, 0.557 mmol), diisopropylethylamine (719.9 mg, 0.97 mL, 5.57 mmol), and 9 (50.3 mg, 0.112 mmol) in THF (4 mL) was added CuI (21.2 mg, 0.557 mmol) at room temperature, and the mixture was stirred at the same temperature for 68 h. After the reaction was quenched with H$_2$O, the mixture was extracted with EtOAc three times, washed with brine, dried over Na$_2$SO$_4$, filtered, and concentrated.

The obtained crude triazole product was used for the next reaction without further purification.

p-Toluenesulfonic acid monohydrate (106.0 mg, 0.557 mmol) was added to a solution of the above crude triazole in MeOH (5 mL). The mixture was stirred at room temperature under air for 15 min. After the reaction was quenched with H$_2$O and saturated aqueous NaHCO$_3$ at room temperature, the mixture was extracted with EtOAc three times, washed with brine, dried over Na$_2$SO$_4$, filtered, and concentrated. The residue was purified by flash column chromatography on silica gel (hexane:EtOAc=2:1) to obtain 25 KK-034 (12.1 mg, 25%, 2 steps) as a colorless oil.

25 KK-034: $[\alpha]_D^{27}$+50.5 (c 0.29, CHCl$_3$); IR (neat) 3393, 1468, 1378, 1223, 766, 695 cm$^{-1}$, $^1$H NMR (600 MHz, CDCl$_3$) δ 0.58 (s, 3H), 0.95 (d, J=6.0 Hz, 3H), 1.03-1.11 (m, 1H), 1.21-1.61 (m, 20H), 1.74-1.81 (m, 2H), 1.87-1.94 (m, 1H), 2.01-2.06 (m, 2H), 2.73-2.75 (m, 1H), 5.04-5.10 (m, 2H), 5.27 (t, J=7.5 Hz, 1H), 7.31-7.33 (m, 1H), 7.42 (t, J=7.8 Hz, 2H), 7.70 (s, 1H), 7.82 (d, J=7.8 Hz, 1H); $^{13}$C NMR (150 MHz, CDCl$_3$) δ 11.9, 18.8, 20.8, 22.1, 23.4, 27.5, 28.9, 29.2, 29.4, 36.0, 36.3, 40.1, 44.4, 45.7, 47.2, 55.7, 56.5, 71.1, 112.8, 118.9, 125.7, 128.0, 128.8, 130.8, 147.3, 147.8; HRMS (ESI$^+$) calcd for C$_{28}$H$_{41}$N3O [M+H]$^+$ 436.3322, found 436.3312.

Example 21

(R)-6-[(1R,3aS,7aR,E)-4-(2-{4-[(1,1'-Biphenyl)-4-yl]-1H-1,2,3-triazol-1-yl}ethylidene)-7a-methyloctahydro-1H-inden-1-yl]-2-methylheptan-2-ol (31 KK-035)

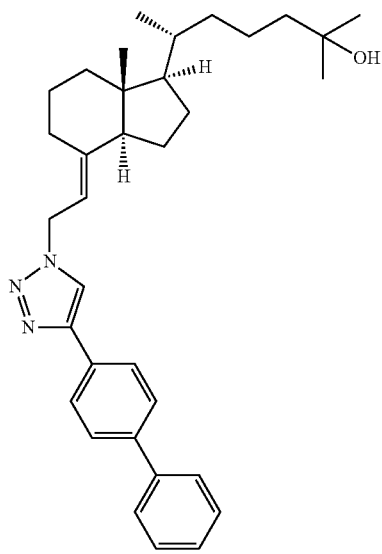

31 KK-035

To a solution of 4-ethynylbiphenyl (99.3 mg, 0.557 mmol), diisopropylethylamine (719.9 mg, 0.97 mL, 5.57 mmol), and 9 (50.3 mg, 0.112 mmol) in THF (8 mL) was added CuI (106.1 mg, 0.557 mmol) at room temperature, and the mixture was stirred at the same temperature for 112 h. After the reaction was quenched with $H_2O$, the mixture was extracted with EtOAc three times, washed with brine, dried over $Na_2SO_4$, filtered, and concentrated.

The obtained crude triazole product was used for the next reaction without further purification.

p-Toluenesulfonic acid monohydrate (106.0 mg, 0.557 mmol) was added to a solution of the above crude triazole in MeOH (10 mL). The mixture was stirred at room temperature under air for 20 min. After the reaction was quenched with $H_2O$ and saturated aqueous $NaHCO_3$ at room temperature, the mixture was extracted with EtOAc three times, washed with brine, dried over $Na_2SO_4$, filtered, and concentrated. The residue was purified by flash column chromatography on silica gel (hexane:EtOAc=2:1) to obtain 31 KK-035 (12.5 mg, 22%, 2 steps) as a colorless oil.

31 KK-035: $[\alpha]_D^{27}$+41.8 (c 0.96, $CHCl_3$); IR (neat) 3350, 1443, 1376, 1215, 1148, 840, 767, 699 cm-1; $^1H$ NMR (600 MHz, $CDCl_3$) δ 0.59 (s, 3H), 0.95 (d, J=6.6 Hz, 3H), 1.041.11 (m, 1H), 1.22-1.61 (m, 20H), 1.75-1.83 (m, 2H), 1.88-1.95 (m, 1H), 2.03-2.07 (m, 2H), 2.74-2.77 (m, 1H), 5.06-5.13 (m, 2H), 5.29 (t, J=7.2 Hz, 1H), 7.34-7.37 (m, 1H), 7.45 (t, J=7.8 Hz, 2H), 7.63 (d, J=7.2 Hz, 2H), 7.67 (d, J=9.0 Hz, 2H), 7.75 (s, 1H), 7.91 (d, J=8.4 Hz, 1H); 1 3C NMR (150 MHz, $CDCl_3$) δ 11.9, 18.8, 20.8, 22.1, 23.4, 27.5, 28.9, 29.2, 29.4, 36.0, 36.3, 40.1, 44.3, 45.7, 47.3, 55.7, 56.5, 71.1, 112.8, 118.9, 126.0, 127.0, 127.4, 127.5, 128.8, 129.8, 140.6, 140.8, 147.4, 147.4; HRMS ($ESI^+$) calcd for $C_{34}H_{45}N_3ONa$ $[M+Na]^+$ 543.3455, found 534.3494.

Example 22

(R)-6-{(1R,3 aS,7 aR,E)-4-[2-(4-Butyl-1H-1,2,3-triazol-1-yl)ethylidene]-7a-methyloctahydro-1H-inden-1-yl}-2-methylheptan-2-ol (28 KK-036)

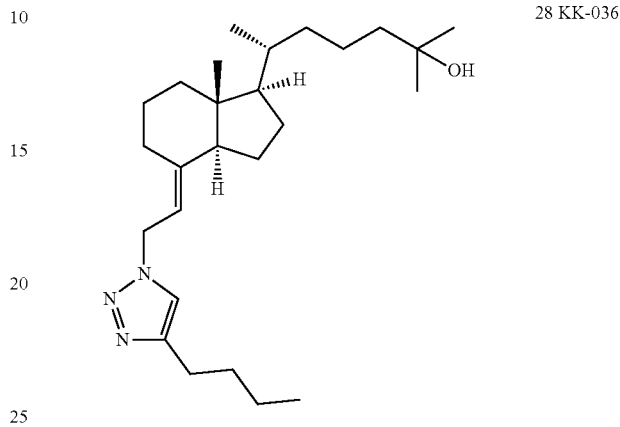

28 KK-036

To a solution of 1-hexyne (9.9 mg, 13.8 μL, 0.12 mmol), diisopropylethylamine (719.9 mg, 0.97 mL, 5.57 mmol), and 9 (53.8 mg, 0.112 mmol) in THF (4 mL) was added CuI (106.1 mg, 0.557 mmol) at room temperature, and the mixture was stirred at the same temperature for 112 h. After the reaction was quenched with $H_2O$, the mixture was extracted with EtOAc three times, washed with brine, dried over $Na_2SO_4$, filtered, and concentrated. The obtained crude triazole product was used for the next reaction without further purification.

p-Toluenesulfonic acid monohydrate (106.0 mg, 0.557 mmol) was added to a solution of the above crude triazole in MeOH (5 mL). The mixture was stirred at room temperature under air for 20 min. After the reaction was quenched with $H_2O$ and saturated aqueous $NaHCO_3$ at room temperature, the mixture was extracted with EtOAc three times, washed with brine, dried over $Na_2SO_4$, filtered, and concentrated. The residue was purified by flash column chromatography on silica gel (hexane:EtOAc=2:1-1:1) to obtain 28 KK-036 (15.6 mg, 31%, 2 steps) as a colorless oil.

28 KK-036: $[\alpha]_D^{27}$+57.5 (c 1.20, $CHCl_3$); IR (neat) 3400, 1467, 1377, 1215, 1047, 732 cm$^{-1}$; $^1H$ NMR (600 MHz, $CDCl_3$) δ 0.54 (s, 3H), 0.91-0.94 (m, 6H), 1.02-1.08 (m, 1H), 1.191.57 (m, 21H), 1.61-1.66 (m, 2H), 1.71-1.77 (m, 2H), 1.85-1.92 (m, 1H), 1.98-2.04 (m, 2H), 2.67-2.71 (m, 3H), 4.94-5.01 (m, 2H), 5.20 (t, J=7.2 Hz, 1H), 7.20 (s, 1H); $^{13}C$ NMR (150 MHz, $CDCl_3$) δ 11.9, 13.8, 18.8, 20.8, 22.1, 22.3, 23.4, 25.4, 27.5, 28.8, 29.2, 29.4, 31.6, 36.0, 36.3, 40.1, 44.3, 45.6, 47.0, 55.6, 56.4, 71.0, 113.1, 119.8, 146.7, 148.4; HRMS ($ESI^+$) calcd for $C_{26}H_{45}N_3ONa$ $[M+Na]^+$ 438.3455, found 438.3473.

Example 23

6-[(1R,3aS,7aR,E)-4-{2-[4-(4-Hydroxybutyl)-1H-1,2,3-triazol-1-yl]ethylidene}-7a-methyloctahydro-1H-inden-1-yl]-2-methylheptan-2-ol (29 KK-037)

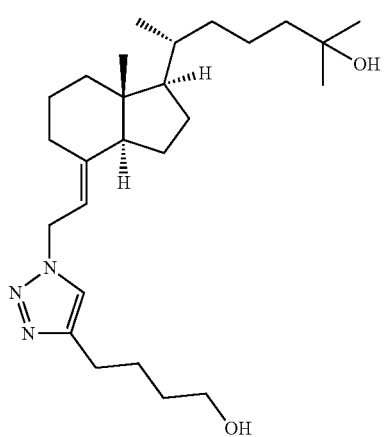

29 KK-037

To a solution of 5-hexyn-1-ol (108.9 mg, 120 μL, 1.11 mmol), diisopropylethyl amine (1.44 g, 1.94 mL, 11.14 mmol), and 9 (60 mg, 0.124 mmol) in THF (8 mL) was added CuI (212.2 mg, 1.11 mmol) at room temperature, and the mixture was stirred at the same temperature for 118 h. After the reaction was quenched with $H_2O$, the mixture was extracted with EtOAc three times, dried over $Na_2SO_4$, filtered, and concentrated. The obtained crude triazole product was used for the next reaction without further purification.

p-Toluenesulfonic acid monohydrate (216.0 mg, 1.11 mmol) was added to a solution of the above crude triazole in MeOH (20 mL). The mixture was stirred at room temperature under air for 25 min. After the reaction was quenched with $H_2O$ and saturated aqueous $NaHCO_3$ at room temperature, the mixture was extracted with EtOAc three times, $Na_2SO_4$, filtered, and concentrated. The residue was purified by flash column chromatography on silica gel (EtOAc only) to obtain 29 KK-037 (19.2 mg, 20%, 2 steps) as a colorless oil.

29 KK-037. $[\alpha]_D^{27}$+40.0 (c 1.48, $CHCl_3$); IR (neat) 3363, 1468, 1378, 1216, 1052, 755 cm$^{-1}$; $^1$H NMR (600 MHz, CDCl3) δ 0.54 (s, 3H), 0.94 (d, J=6.0 Hz, 3H), 1.02-1.08 (m, 1H), 1.21-1.92 (m, 26H), 1.98-2.04 (m, 2H), 2.66-2.70 (m, 1H), 2.74 (t, J=7.5 Hz, 2H), 3.67 (t, J=6.3 Hz, 2H), 4.94-5.01 (m, 2H), 5.20 (t, J=7.2 Hz, 1H), 7.23 (s, 1H); 13C NMR (150 MHz, CDCl$_3$) δ 11.9, 18.8, 20.8, 22.1, 23.4, 25.3, 25.6, 27.5, 28.8, 29.2, 29.4, 32.1, 36.0, 36.3, 40.1, 44.3, 45.6, 47.0, 55.6, 62.4, 71.0, 113.0, 119.9, 146.8, 148.0; HRMS (E SI$^+$) calcd for $C_{26}H_{45}N_3O_2Na$ [M+Na]$^+$ 454.3394, found 438.3404.

Example 24

2-{4-[1-(2-{(1R,3aS,7aR,E)-1-[(R)-6-Hydroxy-6-methylheptan-2-yl]-7a-methyloctahydro-4H-inden-4-ylidene}ethyl)-1H-1,2,3-triazol-4-yl]butyl}isoindoline-1,3-dione (30 KK-038)

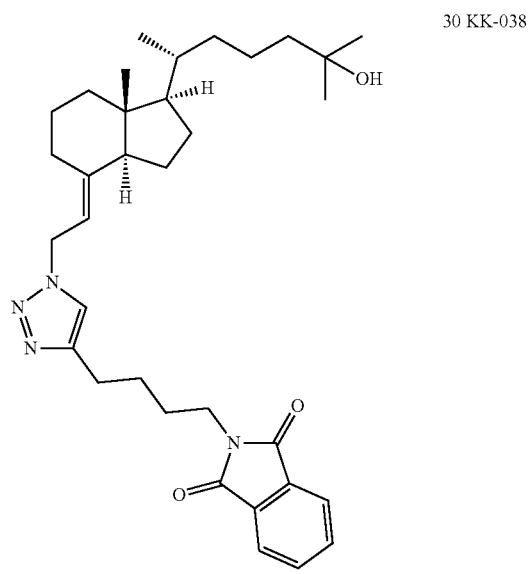 [SMILES: C[C@H](CCCC(C)(C)O)[C@H]1CC[C@H]2/C(=C/Cn3cc(CCCCN4C(=O)c5ccccc5C4=O)nn3)CCC[C@]12C]

30 KK-038

To a solution of phthalimide (11.7 mg, 0.073 mmol), $Ph_3P$ (26.0 mg, 0.10 mmol), and 29 KK-037 (17.1 mg, 0.0396 mmol) in THF (3 mL) was added diisopropyl azodicarboxylate (52 μL, 1.9 M in toluene, 0.10 mmol) at 0° C., and the mixture was stirred at room temperature for 30 min. After the reaction was quenched with $H_2O$ and saturated aqueous $NH_4Cl$, the mixture was extracted with EtOAc three times, washed with brine, dried over $Na_2SO_4$, filtered, and concentrated. The residue was purified by flash column chromatography on silica gel (hexane:EtOAc=1:1) to obtain 30 KK-038 (12.0 mg, 54%) as a colorless oil.

30 KK-038: $[\alpha]_D^{27}$+32.8 (c 0.92, $CHCl_3$); IR (neat) 3404, 1714, 1468, 1398, 1216, 1037, 722 cm-1; $^1$H NMR (600 MHz, CDCl$_3$) δ 0.53 (s, 3H), 0.93 (d, J=6.6 Hz, 3H), 1.03-1.08 (m, 1H), 1.21-1.57 (m, 19H), 1.71-1.76 (m, 6H), 1.85-1.91 (m, 1H), 1.98-2.04 (m, 2H), 2.68-2.70 (m, 1H), 2.76 (t, J=6.9 Hz, 2H), 3.71 (t, J=6.6 Hz, 2H), 4.93-5.01 (m, 2H), 5.20 (t, J=7.2 Hz, 1H), 7.25 (s, 1H), 7.69-7.72 (m, 2H), 7.81-7.84 (m, 2H); $^{13}$C NMR (150 MHz, CDCl$_3$) δ 11.9, 18.8, 20.8, 22.1, 23.4, 25.1, 26.7, 27.5, 28.1, 28.8, 29.2, 29.4, 36.0, 36.3, 37.6, 40.1, 44.4, 45.6, 47.1, 55.6, 56.4, 71.1, 113.0, 120.1, 123.2, 132.1, 133.9, 146.9, 147.5, 168.4; HRMS (ESI$^+$) calcd for $C_{34}H_{48}N_4O_3Na$ [M+Na]$^+$ 583.3619, found 583.3622.

Example 25

(R)-2-Methyl-6-[(1R,3aS,7aR,E)-7a-methyl-4-{2-[4-(pyridin-2-yl)-1H-1,2,3-triazol-1-yl]ethylidene}octahydro-1H-inden-1-yl]heptan-2-ol (26 KK-046)

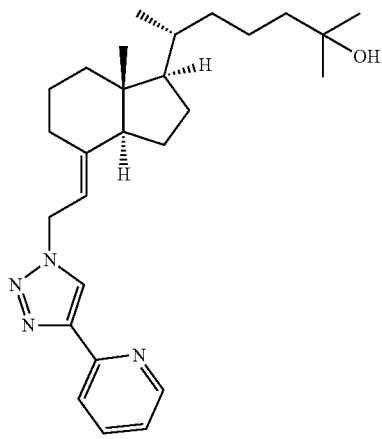

26 KK-046

To a mixture of 2-ethynylpyridine (38.6 mg, 38 µL, 0.374 mmol), sodium L-ascorbate (38.3 mg, 0.193 mmol), 2,6-lutidine (39.0 mg, 43 µL, 0.364 mmol), and 9 (83.8 mg, 0.187 mmol) in t-BuOH (3 mL) and $H_2O$ (3 mL) was added $CuSO_4 \cdot 5H_2O$ (5.2 mg, 0.021 mmol) at room temperature, and the mixture was stirred at the same temperature for 24 h. After the reaction was quenched with $H_2O$, the mixture was extracted with EtOAc three times, washed with brine, dried over $Na_2SO_4$, filtered, and concentrated. The obtained crude triazole product was used for the next reaction without further purification.

p-Toluenesulfonic acid monohydrate (182.8 mg, 0.961 mmol) was added to a solution of the above crude triazole in MeOH (10 mL). The mixture was stirred at room temperature under air for 20 min. After the reaction was quenched with $H_2O$ and saturated aqueous $NaHCO_3$ at room temperature, the mixture was extracted with EtOAc three times, dried over $Na_2SO_4$, filtered, and concentrated. The residue was purified by flash column chromatography on silica gel (hexane:EtOAc=1:1) to obtain 26 KK-046 (60.3 mg, 74%, 2 steps) as a colorless oil.

26 KK-046: $[a]_D^{27}$+55.2 (c 1.08, $CHCl_3$); IR (neat) 3410, 1600, 1471, 1420, 1337, 1200, 1044, 782, 793 cm-1; $^1H$ NMR (600 MHz, $CDCl_3$) δ 0.55 (s, 3H), 0.93 (d, J=6.0 Hz, 3H), 1.02-1.10 (m, 1H), 1.20-1.60 (m, 19H), 1.71-1.80 (m, 2H), 1.85-1.92 (m, 1H), 1.99-2.46 (m, 2H), 2.71-2.74 (m, 1H), 5.04-5.10 (m, 2H), 5.26 (t, J=7.5 Hz, 1H), 7.20-7.22 (m, 1H), 7.77 (td, J=1.8, 7.8 Hz, 1H), 8.11 (s, 1H), 8.17 (d, J=8.4 Hz, 1H), 8.56 (d, J=4.2 Hz, 1H); $^{13}C$ NMR (150 MHz, $CDCl_3$) δ 11.9, 18.8, 20.8, 22.1, 23.3, 27.5, 28.8, 29.2, 29.4, 36.0, 36.3, 40.1, 44.3, 45.6, 47.3, 55.6, 56.4, 71.0, 112.6, 120.2, 121.3, 122.7, 137.0, 147.5, 148.2, 149.2, 150.4; HRMS (ESI+) calcd for $C_{27}H_{40}N_4ONa$ [M+Na]+ 459.3094, found 459.3103.

Example 26

(R)-2-Methyl-6-[(1R,3aS,7aR,E)-7a-methyl-4-{2-[4-(thiophen-2-yl)-1H-1,2,3-triazol-1-yl]ethylidene}octahydro-1H-inden-1-yl]heptan-2-ol (27 KK-047)

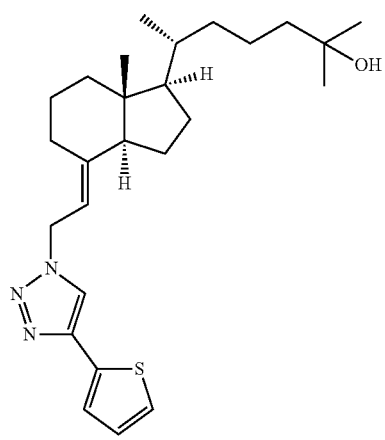

27 KK-047

To a mixture of 2-ethynylthiophene (39.4 mg, 36 µL, 0.364 mmol), sodium L-ascorbate (37.8 mg, 0.191 mmol), 2,6-lutidine (39.0 mg, 42 µL, 0.364 mmol), and 9 (81.6 mg, 0.182 mmol) in t-BuOH (3 mL) and $H_2O$ (3 mL) was added $CuSO_4 \cdot 5H_2O$ (4.2 mg, 0.017 mmol) at room temperature, and the mixture was stirred at the same temperature for 22 h. After the reaction was quenched with $H_2O$, the mixture was extracted with EtOAc three times, washed with brine, dried over $Na_2SO_4$, filtered, and concentrated. The obtained crude triazole product was used for the next reaction without further purification.

p-Toluenesulfonic acid monohydrate (179.2 mg, 0.942 mmol) was added to a solution of the above crude triazole in MeOH (10 mL). The mixture was stirred at room temperature under air for 20 min. After the reaction was quenched with $H_2O$ and saturated aqueous $NaHCO_3$ at room temperature, the mixture was extracted with EtOAc three times, washed with brine, dried over $Na_2SO_4$, filtered, and concentrated. The residue was purified by flash column chromatography on silica gel (hexane:EtOAc=2:1) to obtain 27 KK-047 (53.5 mg, 67%, 2 steps) as a colorless oil.

27 KK-047: $[α]_D^{27}$+47.2 (c 1.35, EtOH); IR (neat) 3418, 1665, 1468, 1420, 1376, 1044, 761 cm-1; $^1H$ NMR (600 MHz, $CDCl_3$) δ 0.57 (s, 3H), 0.95 (d, J=6.4 Hz, 3H), 1.20-1.10 (m, 1H), 1.22-2.06 (m, 24H), 2.70-2.74 (m, 1H), 5.04-5.10 (m, 2H), 5.25 (t, J=7.6 Hz, 1H), 7.07 (dd, J=3.7, 4.9 Hz, 1H), 7.29 (dd, J=1.4, 5.0 Hz, 1H), 7.37 (dd, J=1.4, 3.7 Hz, 1H), 7.61 (s, 1H); 1 3C NMR (150 MHz, $CDCl_3$) δ 11.9, 18.8, 20.8, 22.1, 23.4, 27.5, 28.9, 29.2, 29.4, 36.0, 36.3, 40.1, 44.3, 45.7, 47.3, 55.7, 56.5, 71.1, 112.7, 118.4, 124.0, 124.9, 127.6, 133.2, 142.8, 147.5; HRMS (ESI+) calcd for $C_{26}H_{39}N_3OSNa$ [M+Na]+ 464.2706, found 464.2731.

REFERENCE EXAMPLE 1

Hexafluoro Side Chain (1R,3aR,7aR)-7a-methyl-1-[(R)-7,7,7-trifluoro-6-(methoxymethoxy)-6-(trifluoromethyl)heptan-2-yl]octahydro-4H-inden-4-one (35)

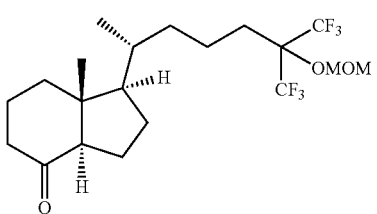

See Ikeda, M.; Matsumura, H.; Sawada, N.; Hashimoto, K.; Tanaka, T.; Noguchi, T.; Hayashi, M. Synthesis and biological evaluations of C-23-modified 26,26,26,27,27,27-F6-vitamin D3 analogues. *Bioorg. Med. Chem.* 2000, 8, 1809-1817.

See Kawagoe, F.; Sugiyama, T.; Uesugi, M.; Kittaka, A. Recent developments for introducing a hexafluoroisopropanol unit into the vitamin D side chain. *J. Steroid Biochem. Mol. Biol.* 2018, 177, 250-254.

Example 27

2-{(1R,3aS,7aR,E)-7a-Methyl-1-[(R)-7,7,7-trifluoro-6-(methoxymethoxy)-6-(trifluoromethyl)heptan-2-yl]octahydro-4H-inden-4-ylidene}ethan-1-ol (36)

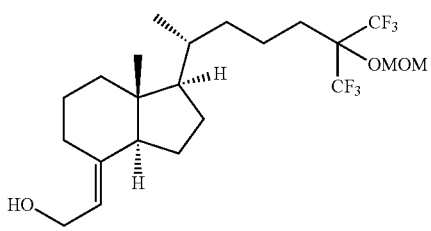

To a suspension of NaH (277.2 mg, 60% in oil, 6.93 mmol) in THF (5 mL) was added $(EtO)_2P(O)CH_2CO_2Et$ (1.75 g, 1.56 mL, 7.79 mmol) at 0° C., and the mixture was stirred at 0° C. for 30 min. Ketone 354,[5] (374.6 mg, 0.866 mmol) was dissolved in THF (5 mL) and the solution was added to the mixture at the same temperature. After being stirred at room temperature for 64 h, the reaction mixture was quenched with $H_2O$ and saturated aqueous $NH_4Cl$ at room temperature. The mixture was extracted with EtOAc three times, washed with brine, dried over $Na_2SO_4$, filtered, and concentrated. The residue was purified by flash column chromatography on silica gel (hexane:EtOAc=10:1) to obtain the crude ethyl ester (418.2 mg) as a colorless oil.

To the solution of the above crude ethyl ester (418.2 mg, 0.832 mmol) in THF (10 mL) was added DIBAL-H (2.5 mL, 1.00 M toluene solution, 2.5 mmol) at -78° C., and the mixture was stirred at room temperature for 20 min. After the reaction was quenched with $H_2O$ and saturated aqueous potassium sodium tartrate at room temperature, the mixture was extracted with EtOAc three times, washed with brine, dried over $Na_2SO_4$, filtered, and concentrated. The residue was purified by flash column chromatography on silica gel (hexane:EtOAc=3:1) to obtain alcohol 36 (364.7 mg, 95%, 2 steps) as a colorless oil.

36: $[a]_D^{27}$+72.2 (c 1.37, $CHCl_3$); IR (neat) 3343, 1471, 1284, 1217, 1145, 1049, 937 cm-1; $^1H$ NMR (600 MHz, $CDCl_3$) δ 0.55 (s, 3H), 0.94 (d, J=6.6 Hz, 3H), 1.03-1.11 (m, 1H), 1.25-1.67 (m, 20H), 1.83-2.04 (m, 5H), 2.11 (dd, J=4.2, 11.4 Hz, 1H), 3.46 (s, 3H), 4.17-4.23 (m, 2H), 4.91 (dd, J=6.9, 9.6 Hz, 2H), 5.22 (t, J=6.9 Hz, 1H); $^{13}C$ NMR (150 MHz, $CDCl_3$) δ 11.8, 18.7, 19.0, 22.2, 23.5, 27.6, 28.7, 28.8, 35.9, 36.4, 40.3, 45.3, 55.6, 56.4, 56.6, 58.7, 80.2 (sept, J=28.7 Hz), 92.8, 119.3, 123.0 (q, J=288.6 Hz), 143.6: HRMS (ESI+) calcd for $C_{22}H_{34}O_3F_6$ [M+Na]+ 483.2304, found 483.2326.

(1R,3aS,7aR,E)-4-(2-Azidoethylidene)-7a-methyl-1-[(R)-7,7,7-trifluoro-6-(methoxymethoxy)-6-(trifluoromethyl)heptan-2-yl]octahydro-1H-indene (37)

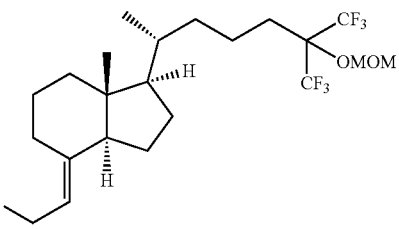

To the solution of the CD-ring 36 (187.8 mg, 0.408 mmol) and pyridine (99 μL, 1.22 mmol) in $CCl_4$ (20 mL) was added tri-n-butylphosphine (509 μL, 2.04 mmol) at 0° C., over 5 min, and the mixture was stirred at the same temperature for 10 min. After the reaction was diluted with hexane, the mixture was filtered, and concentrated. To the residue was added hexane, the mixture was filtered with celite, and concentrated. The crude allylchloride was used for the next reaction without further purification.

To the solution of the above crude allylchloride in DMF (25 mL) was added $NaN_3$ (79.5 mg, 1.22 mmol) at room temperature, and the mixture was stirred at the same temperature for 20 min. After the reaction was quenched with $H_2O$, the mixture was extracted with EtOAc three times, washed with brine, dried over $Na_2SO_4$, filtered, and concentrated. The residue was purified by flash column chromatography on silica gel (hexane:EtOAc=50:1) to obtain azide 37 (162.3 mg, 82%, 2 steps) as a colorless oil.

37: $[a]_D^{27}$+36.3 (c 0.208, $CHCl_3$); IR (neat) 2100, 1468, 1284, 1217, 1161, 1049 cm-1; $^1H$ NMR (600 MHz, $CDCl_3$) δ 0.59 (s, 3H), 0.94 (d, J=6.6 Hz, 3H), 1.05-1.11 (m, 1H), 1.261.71 (m, 10H), 1.85-2.04 (m, 5H), 2.60-2.64 (m, 1H), 3.46 (s, 3H), 3.73 (dd, J=7.2, 13.8 Hz, 2H), 3.89 (dd, J=8.4, 13.8 Hz, 2H), 4.90-4.93 (m, 2H), 5.13 (t, J=7.5 Hz, 1H); 13C NMR (150 MHz, $CDCl_3$) δ 11.8, 18.7, 18.9, 22.1, 23.8, 27.5, 28.8, 35.9, 36.3, 40.2, 45.1, 47.4, 55.7, 56.4, 56.5, 80.2 (sept, J=28.0 Hz), 92.8, 112.8, 123.0 (q, J=288.6 Hz), 147.0; HRMS (ESI+) calcd for $C_{22}H_{34}N_3O_2F_6$ [M+H]+ 486.2550, found 486.2555.

Example 28

(R)-1,1,1-Trifluoro-6-{(1R,3aS,7aR,E)-7a-methyl-4-[2-(4-phenyl-1H-1,2,3-triazol-1-yl)ethylidene]octahydro-1H-inden-1-yl}-2-(trifluoromethyl)heptan-2-ol (38 KK-050)

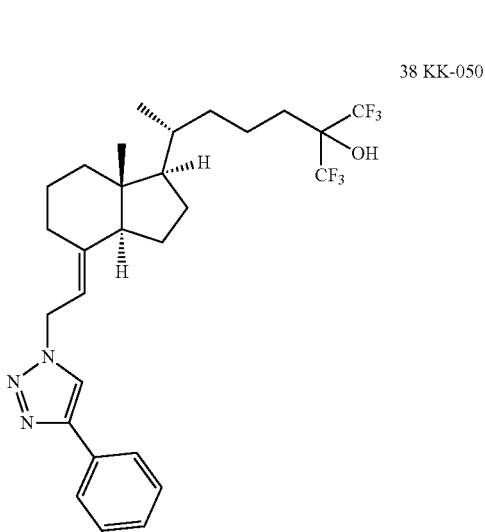 [SMILES: C[C@H](CCCC(O)(C(F)(F)F)C(F)(F)F)[C@H]1CC[C@H]2/C(=C/Cn3cc(-c4ccccc4)nn3)CCC[C@]12C]

38 KK-050

To a solution of ethynylbenzene (20 µL, 0.186 mmol), 2,6-lutidine (29 µL, 0.248 mmol), sodium ascorbate (24.6 mg, 0.124 mmol) and CD-ring 37 (60.0 mg, 0.124 mmol) in tBuOH (3 mL) and H$_2$O (3 mL) was added CuSO$_4$·5H$_2$O (3.1 mg, 0.012 mmol) at room temperature, and the mixture was stirred at the same temperature for 25 h. After the reaction was quenched with H$_2$O, the mixture was extracted with EtOAc three times, washed with brine, dried over Na$_2$SO$_4$, filtered, and concentrated. The crude triazole product was used for the next reaction without further purification.

Methanesulfonic acid (0.4 mL) was added to a solution of the above crude product in MeOH (20 mL). The mixture was stirred at room temperature under air for 9 h. After the reaction was quenched with H$_2$O and saturated aqueous NaHCO$_3$ at room temperature, the mixture was extracted with EtOAc three times, dried over Na$_2$SO$_4$, filtered, and concentrated. The residue was purified on a preparative silica gel TLC plate (hexane:EtOAc=2:1) to obtain 38 KK-050 (37.1 mg, 55%) as a colorless oil.

38 KK-050: $[\alpha]_D^{27}$+22.3 (c 0.24, CHCl$_3$); IR (neat) 3143, 1468, 1225, 763 cm-1; $^1$H NMR (600 MHz, CDCl$_3$) δ 0.56 (s, 3H), 0.93 (d, J=6.6 Hz, 3H), 1.04-1.11 (m, 1H), 1.21-2.04 (m, 17H), 2.72-2.75 (m, 1H), 4.21 (brs, 1H), 5.03-5.09 (m, 2H), 5.25 (t, J=7.2 Hz, 1H), 7.32-7.34 (m, 1H), 7.42 (t, J=7.8 Hz, 2H), 7.70 (s, 1H), 7.80 (d, J=7.2 Hz, 1H); $^{13}$C NMR (150 MHz, CDCl$_3$) δ 11.9, 18.5, 18.7, 22.1, 23.4, 27.5, 28.8, 30.9, 35.8, 36.1, 40.0, 45.7, 47.3, 55.6, 56.3, 76.3 (sept, J=28.8 Hz), 112.8, 119.0, 123.3 (q, J=285.8 Hz), 125.7, 128.2, 128.8, 130.5, 147.3, 147.8; HRMS (ESI$^+$) calcd for C$_{28}$H$_{36}$N$_3$OF$_6$ [M+H]$^+$ 544.2757, found 544.2787.

Example 29

(R)-1,1,1-Trifluoro-6-[(1R,3aS,7aR,E)-4-{2-[4-(4-fluorophenyl)-1H-1,2,3-triazol-1-yl]ethylidene}-7a-methyloctahydro-1H-inden-1-yl]-2-(trifluoromethyl)heptan-2-ol (39 KK-056)

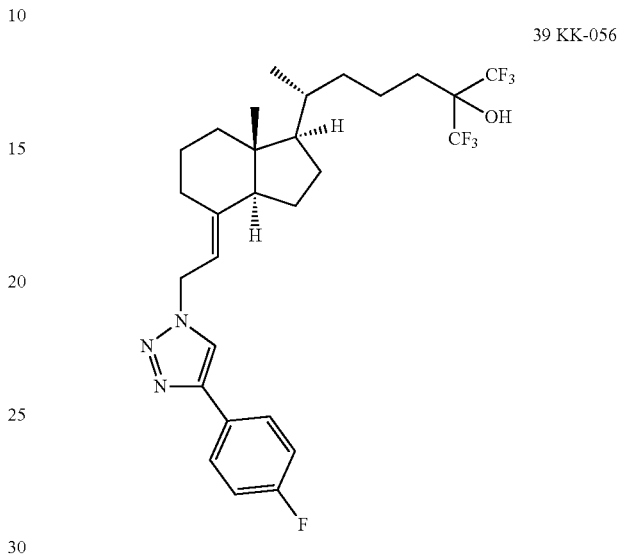

39 KK-056

To a solution of 1-ethynyl-4-fluorobenzene (17.1 mg, 0.142 mmol), 2,6-lutidine (16 µL, 0.142 mmol), sodium ascorbate (17.8 mg, 0.090 mmol) and CD-ring 37 (34.5 mg, 0.071 mmol) in tBuOH (3 mL) and H$_2$O (3 mL) was added CuSO$_4$·5H$_2$O (3.3 mg, 0.013 mmol) at room temperature, and the mixture was stirred at the same temperature for 63 h. After the reaction was quenched with H$_2$O, the mixture was extracted with EtOAc three times, washed with brine, dried over Na$_2$SO$_4$, filtered, and concentrated. The crude triazole product was used for the next reaction without further purification.

Methanesulfonic acid (0.2 mL) was added to a solution of the above crude product in MeOH (10 mL). The mixture was stirred at room temperature under air for 20 h. After the reaction was quenched with H$_2$O and saturated aqueous NaHCO$_3$ at room temperature, the mixture was extracted with EtOAc three times, dried over Na$_2$SO$_4$, filtered, and concentrated. The residue was purified on a preparative silica gel TLC plate (hexane:EtOAc=1:1) to obtain 39 KK-056 (27.8 mg, 70%) as a colorless oil.

39 KK-056: $[\alpha]_D^{27}$+41.3 (c 2.14, CHCl$_3$); IR (neat) 3147, 1498, 1470, 1228, 843, 760 cm$^{-1}$; $^1$H NMR (600 MHz, CDCl$_3$) δ 0.56 (s, 3H), 0.93 (d, J=6.6 Hz, 3H), 1.04-1.11 (m, 1H), 1.22-2.04 (m, 17H), 2.71-2.74 (m, 1H), 5.01-5.09 (m, 2H), 5.24 (t, J=7.5 Hz, 1H), 7.09-7.12 (m, 2H), 7.66 (s, 1H), 7.76-7.78 (m, 2H); $^{13}$C NMR (150 MHz, CDCl$_3$) δ 11.9, 18.5, 18.7, 22.1, 23.4, 27.5, 28.8, 31.0, 35.8, 36.1, 40.0, 45.7, 47.4, 55.6, 56.3, 76.3 (sept, J=28.8 Hz), 112.8, 115.8 (d, J=21.6 Hz), 118.8, 123.3 (q, J=284.4 Hz), 126.7, 127.5 (d, J=8.6 Hz), 146.9, 147.4, 162.7 (d, J=245.6 Hz); HRMS (ESI$^+$) calcd for C$_{28}$H$_{34}$N$_3$OF$_7$Na [M+Na]$^+$ 584.2482, found 584.2477.

Examples 30 and 31

(R)-1,1,1-Trifluoro-6-{(1R,3aS,7aR,E)-7a-methyl-4-[2-(5-phenyl-2H-tetrazol-2-yl)ethylidene]octahydro-1H-inden-1-yl}-2-(trifluoromethyl)heptan-2-ol (40 KK-048)

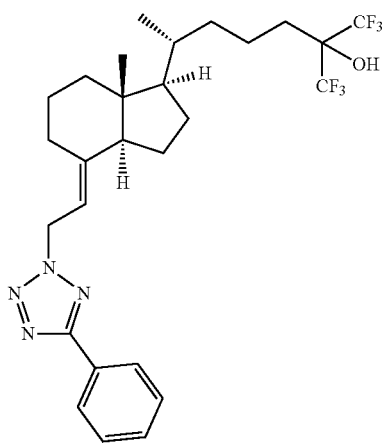

40 KK-048

(R)-1,1,1-Trifluoro-6-{(1R,3aS,7aR,E)-7a-methyl-4-[2-(5-phenyl-1H-tetrazol-1-yl)ethylidene]octahydro-1H-inden-1-yl}-2-(trifluoromethyl)heptan-2-ol (41 KK-049)

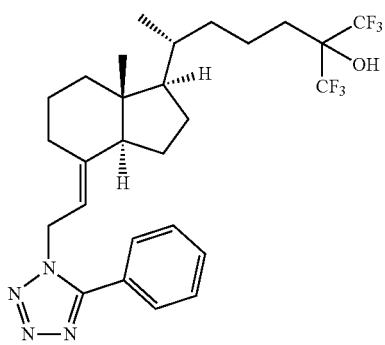

41 KK-049

To a solution of 5-phenyl-1H-tetrazole (166.6 mg, 1.14 mmol), Ph$_3$P (199.3 mg, 0.76 mmol), and CD-ring 36 (175.0 mg, 0.38 mmol) in THF (5 mL) was added diisopropyl diazocarboxylate (600 μL, 1.9 M in toluene, 1.14 mmol) at 0° C., and the mixture was stirred for 1 h. After the reaction was quenched with H$_2$O at 0° C., the mixture was extracted with EtOAc three times, washed with brine, dried over Na$_2$SO$_4$, filtered, and concentrated. The residue was roughly purified by flash column chromatography on silica gel (hexane:EtOAc=4:1) to obtain the crude products (less polar and more polar products).

Methanesulfonic acid (0.4 mL) was added to a solution of the above less polar crude product in MeOH (20 mL). The mixture was stirred at room temperature under air for 6 h. After the reaction was quenched with H$_2$O and saturated aqueous NaHCO$_3$ at room temperature, the mixture was extracted with EtOAc three times, dried over Na$_2$SO$_4$, filtered, and concentrated. The residue was purified by flash column chromatography on silica gel (hexane:EtOAc=10:1) to obtain 40 KK-048 (87.2 mg, 42%) as a colorless oil.

40 KK-048: $[\alpha]_D^{27}$+33.8 (c 0.68, CHCl$_3$); IR (neat) 3205, 1471, 1452, 1228, 1176, 734 cm$^{-1}$; $^1$H NMR (600 MHz, CDCl$_3$) δ 0.54 (s, 3H), 0.94 (d, J=6.6 Hz, 3H), 1.04-1.11 (m, 1H), 1.23-2.03 (m, 17H), 2.83-2.86 (m, 1H), 3.13 (brs, 1H), 5.28-5.45 (m, 3H), 7.44-7.50 (m, 3H), 8.13-8.15 (m, 2H); $^{13}$C NMR (150 MHz, CDCl$_3$) δ 11.8, 18.5, 18.7, 22.0, 23.3, 27.5, 29.1, 30.8, 35.8, 36.1, 40.1, 45.9, 50.2, 55.6, 56.3, 76.2 (sept, J=28.7 Hz), 111.7, 123.2 (q, J=284.4 Hz), 126.8, 127.6, 128.8, 130.2, 147.9, 165.0; HRMS (ESI$^-$) calcd for C$_{28}$H$_{35}$N$_4$O$_3$F$_6$[M+HCOO]$^-$ 589.2619, found 589.2594.

Methanesulfonic acid (0.4 mL) was added to a solution of the above more polar crude product in MeOH (20 mL). The mixture was stirred at room temperature under air for 8 h. After the reaction was quenched with H$_2$O and saturated aqueous NaHCO$_3$ at room temperature, the mixture was extracted with EtOAc three times, dried over Na$_2$SO4, filtered, and concentrated. The residue was purified on a preparative silica gel TLC plate (hexane:EtOAc=2:1) to obtain 41 KK-049 (35.7 mg, 17%) as a colorless oil.

41 KK-049: $[\alpha]_D^{27}$+40.5 (c 0.19, CHCl$_3$); IR (neat) 3227, 1475, 1225, 759 cm-1; $^1$H NMR (600 MHz, CDCl$_3$) δ 0.44 (s, 3H), 0.92 (d, J=6.0 Hz, 3H), 1.03-1.10 (m, 1H), 1.20-1.99 (m, 17H), 2.51-2.55 (m, 1H), 3.85 (brs, 1H), 5.06-5.17 (m, 3H), 7.53-7.59 (m, 3H), 7.677.68 (m, 2H); 1 3C NMR (150 MHz, CDCl$_3$) δ 11.8, 18.4, 18.6, 22.0, 23.1, 27.4, 28.9, 30.9, 35.8, 36.1, 40.0, 45.6, 45.7, 55.4, 56.2, 76.3 (sept, J=28.8 Hz), 112.8, 123.3 (q, J=284.4 Hz), 124.0, 128.8, 129.2, 131.2, 146.5, 154.1; HRMS (ESI$^-$) calcd for C$_{28}$H$_{35}$N$_4$O$_3$F$_6$ [M+HCOO]$^-$ 589.2619, found 589.2582.

REFERENCE EXAMPLE 2

24,24-Difluorinated Side Chain (1R,3aR,7aR)-1-{(R)-5,5-Difluoro-6-methyl-6-[(triethylsilyl)oxy]heptan-2-yl}-7a-methyloctahydro-4H-inden-4-one (43)

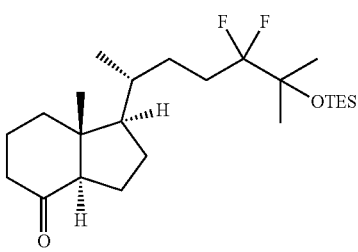

43

See Flores, A.; Massarelli, I.; Thoden, J. B.; Plum, L. A.; DeLuca, H. F.; A methylene group on C-2 of 24,24-difluoro-19-nor-1 α,25-dihydroxyvitamin D3 markedly increases bone calcium mobilization in vivo. *J. Med. Chem.* 2015, 58, 9731-9741.

See Kawagoe, F.; Mototani, S.; Yasuda, K.; Nagasawa, K.; Uesugi, M.; Sakaki, T.; Kittaka, A. Introduction of fluorine atoms to vitamin D3 side-chain and synthesis of 24,24-difluoro-25-hydroxyvitamin D3. *J. Steroid Biochem. Mol. Biol.* 2019, 195, #105477.

67

(E)-2-(1-{5,5-Difluoro-6-methyl-6-[(triethylsilyl)oxy]heptan-2-yl}-7a-methyloctahydro-4H-inden-4-ylidene)ethan-1-ol (44)

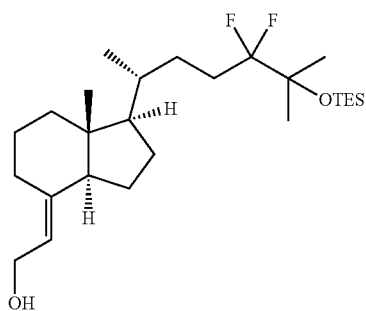

To a suspension of NaH (315.1 mg, 60% in oil, 7.90 mmol) in THF (5 mL) was added (EtO)$_2$P(O)CH$_2$CO$_2$Et (1.90 g, 1.7 mL, 8.46 mmol) at 0° C., and the mixture was stirred at 0° C. for 30 min. Ketone 43 (331.1 mg, 0.769 mmol) was dissolved in THF, and the solution was added to the mixture at the same temperature. After being stirred at room temperature for 72 h, the reaction mixture was quenched with H$_2$O and saturated aqueous NH$_4$Cl at room temperature. The mixture was extracted with EtOAc three times, washed with brine, dried over Na$_2$SO$_4$, filtered, and concentrated. The residue was purified by flash column chromatography on silica gel (hexane:EtOAc=10:1) to obtain crude ethyl ester (343.7 mg) as a colorless oil.

To the solution of the above ethyl ester (343.7 mg) in THF (10 mL) was added DIBAL-H (4.1 mL, 1.0 M toluene solution, 4.1 mmol) at −78° C., and the mixture was stirred at room temperature for 40 min. After the reaction was quenched with H$_2$O and saturated aqueous potassium sodium tartrate at room temperature, the mixture was extracted with EtOAc three times, washed with brine, dried over Na$_2$SO$_4$, filtered, and concentrated. The residue was purified by flash column chromatography on silica gel (hexane:EtOAc=7:1) to obtain alcohol 44 (278.8 mg, 79%, 2 steps) as a colorless oil.

44: $[\alpha]_D^{27}$+42.6 (c 0.68, CHCl$_3$); IR (neat) 3330, 1458, 1384, 1198, 1162, 1054, 738 cm$^{-1}$; $^1$H NMR (600 MHz, CDCl$_3$) δ 0.56 (s, 3H), 0.60 (q, J=7.8 Hz, 6H), 0.93-0.96 (m, 12H), 1.24-2.05 (m, 23H), 2.61-2.64 (m, 1H), 4.17-4.23 (m, 2H), 5.22 (t, J=6.9 Hz, 1H); 13C NMR (150 MHz, CDCl$_3$) δ 6.6, 6.9, 11.8, 18.6, 22.1, 23.5, 24.3, 24.6, 26.8, 27.0 (t, J=24.5 Hz), 27.4, 28.7, 35.7, 40.3, 45.3, 55.6, 56.3, 58.7, 75.6 (t, J=28.7 Hz), 119.3, 125.3 (t, J=247.1 Hz), 143.7; HRMS (ESI$^+$) calcd for C$_{26}$H$_{48}$O$_2$F$_2$SiNa [M+Na]$^+$ 481.3284, found 481.3254.

68

({(R)-6-[(1R,3aS,7aR,E)-4-(2-Azidoethylidene)-7a-methyloctahydro-1H-inden-1-yl]-3,3-difluoro-2-methylheptan-2-yl}oxy)triethylsilane (45)

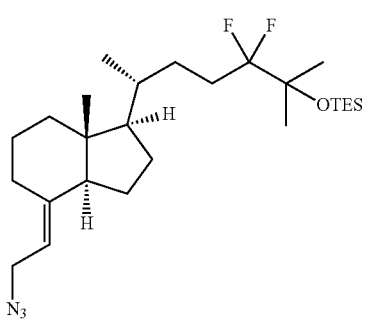

To the solution of the 44 (133.0 mg, 0.29 mmol) and pyridine (70 μL, 0.87 mmol) in CCl$_4$ (10 mL) was added tri-n-butylphosphine (362 μL, 1.45 mmol) at 0° C., over 10 min, and the mixture was stirred at the same temperature for 10 min. After the reaction was diluted with hexane, the mixture was filtered, and concentrated. To the residue was added hexane, the mixture was filtered, and concentrated. The crude allylchloride was used for the next reaction without further purification To the solution of the crude allylchloride in DMF (15 mL) was added NaN3 (57.2 mg, 0.88 mmol) at room temperature, and the mixture was stirred at the same temperature for 20 min. After the reaction was quenched with H$_2$O, the mixture was extracted with EtOAc three times, washed with brine, dried over Na$_2$SO$_4$, filtered, and concentrated. The residue was purified by flash column chromatography on silica gel (hexane:EtOAc=50:1) to obtain azide 45 (114.1 mg, 81%, 2 steps) as a colorless oil.

45: $[\alpha]_D^{27}$+35.3 (c 2.43, CHCl$_3$); IR (neat) 2104, 1464, 1380, 1240, 1197, 1161, 1057, 734 cm-1; $^1$H NMR (400 MHz, CDCl$_3$) δ 0.57-0.63 (m, 9H), 0.93 (m, 12H), 1.24-2.02 (m, 23H), 3.73 (dd, J=7.3, 13.3 Hz, 1H), 3.90 (dd, J=8.3, 13.3 Hz, 1H), 5.13 (t, J=7.6 Hz, 1H); $^{13}$C NMR (100 MHz, CDCl$_3$) δ 6.6, 6.9, 11.8, 22.1, 23.8, 24.3, 26.8, 27.0 (t, J=24.8 Hz), 27.4, 28.8, 35.7, 40.2, 45.1, 47.4, 55.8, 56.3, 75.6 (t, J=28.1 Hz), 112.7, 125.3 (t, J=247.9 Hz), 147.1; HRMS (ESI$^+$) calcd for C$_{26}$H$_{48}$N$_3$OF$_2$Si [M+H]$^+$ 484.3529, found 484.3518.

Example 32

(R)-3,3-Difluoro-2-methyl-6-{(1R,3aS,7aR,E)-7a-methyl-4-[2-(4-phenyl-1H-1,2,3-triazol-1-yl)ethyl-idene]octahydro-1H-inden-1-yl}heptan-2-ol (46 KK-053)

Example 32

(R)-3,3-Difluoro-6-[(1R,3aS,7aR,E)-4-{2-[4-(4-fluorophenyl)-1H-1,2,3-triazol-1-yl]ethylidene}-7a-methyloctahydro-1H-inden-1-yl]-2-methylheptan-2-ol (47 KK-057) 47 KK 57

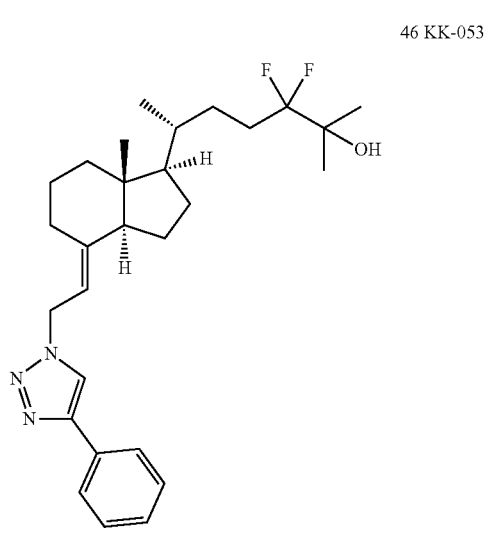 [SMILES: C[C@H](CCC(F)(F)C(C)(C)O)[C@H]1CC[C@H]2/C(=C/Cn3cc(-c4ccccc4)nn3)CCC[C@]12C]
46 KK-053

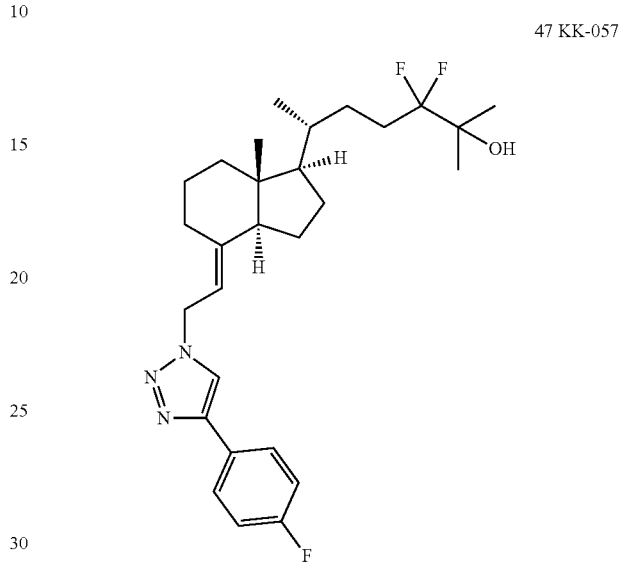
47 KK-057

To a mixture of phenylacetylene (20 μL, 0.186 mmol), 2,6-lutidine (29 μL, 0.248 mmol), sodium ascorbate (33.1 mg, 0.167 mmol) and 24,24-difluoro-CD-ring 45 (60 mg, 0.124 mmol) in tBuOH (3 mL) and $H_2O$ (3 mL) was added $CuSO_4$-$5H_2O$ (3.2 mg, 0.013 mmol) at room temperature, and the mixture was stirred at the same temperature for 22 h. After the reaction was quenched with $H_2O$, the mixture was extracted with EtOAc three times, washed with brine, dried over $Na_2SO_4$, filtered, and concentrated. The crude triazole product was used for the next reaction without further purification.

p-Toluenesulfonic acid monohydrate (190.2 mg, 1.0 mmol) was added to a solution of the crude triazole product in MeOH (10 mL). The mixture was stirred at room temperature for 1 h under air. After the reaction was quenched with $H_2O$ and saturated aqueous $NaHCO_3$ at room temperature, the mixture was extracted with EtOAc three times, dried over $Na_2SO_4$, filtered, and concentrated. The residue was purified on a preparative silica gel TLC plate (hexane: EtOAc=1:1) to obtain 46 KK-053 (24.7 mg, 47% 2 steps) as a colorless oil.

46 KK-053: $[\alpha]_D^{27}$+48.3 (c 0.45, $CHCl_3$); IR (neat) 3378, 1470, 1380, 1177, 1017, 767, 696 cm-1; $^1H$ NMR (400 MHz, $CDCl_3$) δ 0.59 (s, 3H), 0.96 (d, J=6.4 Hz, 3H), 1.25-2.07 (m, 23H), 2.72-2.77 (m, 1H), 5.03-5.12 (m, 2H), 5.28 (t, J=7.3 Hz, 1H), 7.32 (tt, J=0.9, 7.3 Hz, 1H), 7.40-7.44 (m, 2H), 7.70 (s, 1H), 7.81-7.83 (m, 2H); $^{13}C$ NMR (100 MHz, $CDCl_3$) δ 11.9, 18.6, 22.0, 23.3, 23.5, 26.7, 27.3, 27.3 (t, J=26.7 Hz), 28.8, 35.6, 40.0, 45.6, 47.2, 55.6, 56.1, 73.3 (t, J=27.7 Hz), 112.9, 118.9, 125.5 (t, J=246.0 Hz), 125.6, 128.0, 128.7, 130.7, 147.1, 147.7; HRMS (ESI+) calcd for $C_{28}H_{39}N_3OF_2Na$ $[M+Na]^+$ 494.2953, found 494.2941.

To a solution of 4-fluorophenylacetylene (23.3 mg, 0.194 mmol), 2,6-lutidine (21 μL, 0.182 mmol), sodium ascorbate (30.5 mg, 0.154 mmol) and 24,24-difluoro-CD-ring 45 (44.0 mg, 0.091 mmol) in tBuOH (3 mL) and $H_2O$ (2 mL) was added $CuSO_4$-$5H_2O$ (4.5 mg, 0.018 mmol) at room temperature, and the mixture was stirred at the same temperature for 74 h 30 min. After the reaction was quenched with $H_2O$, the mixture was extracted with EtOAc three times, washed with brine, dried over $Na_2SO_4$, filtered, and concentrated. The crude triazole product was used for the next reaction without further purification.

p-Toluenesulfonic acid monohydrate (190.2 mg, 1.0 mmol) was added to a solution of the crude triazole product in MeOH (10 mL). The mixture was stirred at room temperature for 1 h under air. After the reaction was quenched with $H_2O$ and saturated aqueous $NaHCO_3$ at room temperature, the mixture was extracted with EtOAc three times, dried over Na 2SO4, filtered, and concentrated. The residue was purified on a preparative silica gel TLC plate (hexane: EtOAc=1:1) to obtain 47 KK-057 (30.8 mg, 69% 2 steps) as a colorless oil.

47 KK-057: $[\alpha]_D^{27}$+44.2 (c 2.37, $CHCl_3$); IR (neat) 3393, 1498, 1380, 1230, 1177, 1016, 843, 759 cm-1; $^1H$ NMR (600 MHz, $CDCl_3$) δ 0.58 (s, 3H), 0.95 (d, J=6.6 Hz, 3H), 1.25-2.05 (m, 23H), 2.73-2.75 (m, 1H), 5.03-5.10 (m, 2H), 5.27 (t, J=7.2 Hz, 1H), 7.08-7.12 (m, 2H), 7.66 (s, 1H), 7.77-7.80 (m, 2H); $^{13}C$ NMR (150 MHz, $CDCl_3$) δ 11.9, 18.6, 22.1, 23.4, 23.6, 26.8, 27.4, 27.4 (t, J=27.3 Hz), 28.8, 35.6, 40.0, 45.7, 47.3, 55.6, 56.2, 73.3 (t, J=27.2 Hz), 111.6, 115.8 (d, J=21.6 Hz), 118.6, 125.5 (t, J=246.9 Hz), 127.0, 127.4 (d, J=7.2 Hz), 146.9, 147.3, 163.1 (d, J=245.7 Hz); HRMS (ESI+) calcd for $C_{28}H_{38}N_3OF_3Na$ $[M+Na]^+$ 512.2859, found 512.2880.

Examples 32 and 33

(R)-3,3-Difluoro-2-methyl-6-{(1R,3aS,7aR,E)-7a-methyl-4-[2-(5-phenyl-2H-tetrazol-2-yl)ethylidene]octahydro-1H-inden-1-yl}heptan-2-ol (48 KK-051)

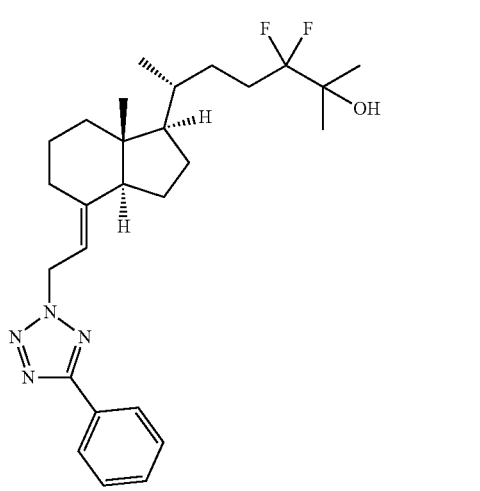

48 KK-051

(R)-3,3-Difluoro-2-methyl-6-{(1R,3aS,7aR,E)-7a-methyl-4-[2-(5-phenyl-1H-tetrazol-1-yl)ethylidene]octahydro-1H-inden-1-yl}heptan-2-ol (50 KK-052)

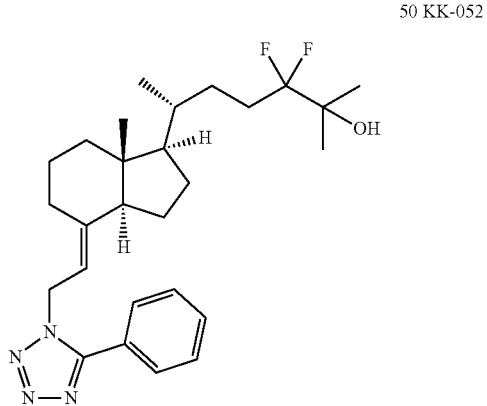 [SMILES: C[C@H](CCC(F)(F)C(C)(C)O)[C@H]1CC[C@H]2/C(=C/Cn3nnnc3-c3ccccc3)CCC[C@]12C]

50 KK-052

To a solution of 5-phenyl-1H-tetrazole (126.7 mg, 0.867 mmol), Ph$_3$P (152.3 mg, 0.581 mmol), and 24,24-difluoro-CD-ring 44 (132.0 mg, 0.288 mmol) in THF (5 mL) was added diisopropyl azodicarboxylate (454 μL, 1.9 M in toluene, 0.863 mmol) at 0° C., and the mixture was stirred at the same temperature for 45 min. After the reaction was quenched with H$_2$O at 0° C., the mixture was extracted with CH$_2$Cl$_2$ three times, dried over Na$_2$SO$_4$, filtered, and concentrated. The residue was roughly purified by flash column chromatography on silica gel (hexane:EtOAc=4:1) to obtain crude products (less polar and more polar products).

p-Toluenesulfonic acid monohydrate (190.2 mg, 1.0 mmol) was added to a solution of the above less polar crude product in MeOH (10 mL). The mixture was stirred at room temperature for 1 h under air. After the reaction was quenched with H$_2$O and saturated aqueous NaHCO$_3$ at room temperature, the mixture was extracted with CH$_2$Cl$_2$ three times, dried over Na$_2$SO$_4$, filtered, and concentrated. The residue was purified by flash column chromatography on silica gel (hexane:EtOAc=3:1) to obtain 48 KK-051 (65.4 mg, 48%) as a colorless oil.

48 KK-051: [α]$_D^{27}$+38.1 (c 0.54, CHCl$_3$); IR (neat) 3445, 1468, 1450, 1381, 1177, 1017, 736, 695 cm-1; $^1$H NMR (600 MHz, CDCl$_3$) δ 0.55 (s, 3H), 0.94 (d, J=6.6 Hz, 3H), 1.272.04 (m, 23H), 2.84 (dd, J=3.9, 15.9 Hz, 1H), 5.25-5.35 (m, 3H), 7.43-7.49 (m, 3H), 8.13-8.15 (m, 2H); $^{13}$C NMR (150 MHz, CDCl$_3$) δ 11.8, 18.6, 22.0, 23.3, 23.5, 26.7, 27.4 (t, J=25.1 Hz), 27.4, 29.0, 35.6, 40.1, 45.8, 50.1, 55.6, 56.1, 73.3 (t, J=27.8 Hz), 111.7, 125.5 (t, J=247.1 Hz), 126.8, 127.6, 128.8, 130.1, 147.8, 165.0; HRMS (ESI$^+$) calcd for C$_{27}$H$_{38}$N$_4$OF$_2$Na [M+Na]$^+$ 495.2906, found 495.2891.

p-Toluenesulfonic acid monohydrate (190.8 mg, 1.0 mmol) was added to a solution of the above more polar crude product in MeOH (10 mL). The mixture was stirred at room temperature for 1 h under air. After the reaction was quenched with H$_2$O and saturated aqueous NaHCO$_3$ at room temperature, the mixture was extracted with CH$_2$Cl$_2$ three times, dried over Na$_2$SO$_4$, filtered, and concentrated. The residue was purified on a preparative silica gel TLC plate (hexane:EtOAc=1:1) to obtain 50 KK-052 (16.3 mg, 12%) as a colorless oil.

50 KK-052: [α]$_D^{27}$+46.6 (c 1.28, CHCl$_3$); IR (neat) 3408, 1471, 1381, 1177, 1017, 698 cm$^{-1}$; $^1$H NMR (400 MHz, CDCl$_3$) δ 0.46 (s, 3H), 0.93 (d, J=6.4 Hz, 3H), 1.26-2.08 (m, 23H), 2.53-2.57 (m, 1H), 5.04-5.17 (m, 3H), 7.52-7.60 (m, 3H), 7.68-7.70 (m, 2H); 1 3C NMR (100 MHz, CDCl$_3$) δ 11.8, 18.6, 22.0, 23.1, 23.6, 26.7, 27.3, 27.3 (t, J=24.8 Hz), 28.9, 35.6, 40.0, 45.6, 45.7, 55.5, 56.1, 73.3 (t, J=26.7 Hz), 112.9, 124.2, 125.5 (t, J=247.0 Hz), 128.8, 129.1, 131.1, 146.4, 154.1; HRMS (ESI$^+$) calcd for C$_{27}$H$_{38}$N$_4$OF$_2$Na [M+Na]$^+$ 495.2906, found 495.2908.

Examples 34 and 35

3,3-Difluoro-6-[(1R,3aS,7aR,E)-4-{2-[5-(4-fluorophenyl)-2H-tetrazol-2-yl]ethylidene}-7a-methyloctahydro-1H-inden-1-yl]-2-methylheptan-2-ol (49 KK-061)

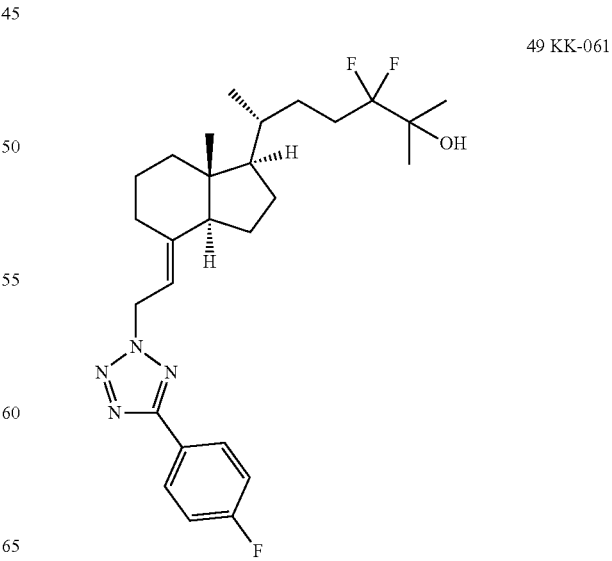

49 KK-061

(R)-3,3-Difluoro-6-[(1R,3aS,7aR,E)-4-{2-[5-(4-fluorophenyl)-1H-tetrazol-1-yl]ethylidene}-7a-methyl-octahydro-H-inden-1-yl]-2-methylheptan-2-ol (51 KK-062)

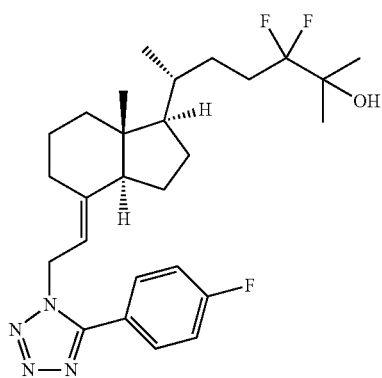

51 KK-062

To a solution of 5-(4-fluorophenyl)-1H-tetrazole (75.8 mg, 0.462 mmol), $Ph_3P$ (79.4 mg, 0.303 mmol), and 24,24-difluoro-CD-ring 44 (69.4 mg, 0.151 mmol) in $CH_2Cl_2$ (3 mL) was added diisopropyl azodicarboxylate (239 μL, 1.9 M in toluene, 0.454 mmol) at 0° C., and the mixture was stirred at the same temperature for 2 h. After the reaction was quenched with $H_2O$ at 0° C., the mixture was extracted with $CH_2Cl_2$ three times, dried over $Na_2SO_4$, filtered, and concentrated. The residue was roughly purified by flash column chromatography on silica gel (hexane:EtOAc=4:1) to obtain crude products (less polar and more polar products).

p-Toluenesulfonic acid monohydrate (96.9 mg, 0.509 mmol) was added to a solution of the above less polar crude product in MeOH (5 mL) and $CH_2Cl_2$ (5 mL). The mixture was stirred at room temperature for 150 min under air. After the reaction was quenched with $H_2O$ and saturated aqueous $NaHCO_3$ at room temperature, the mixture was extracted with EtOAc three times, washed with brine, dried over $Na_2SO_4$, filtered, and concentrated. The residue was purified on a preparative silica gel TLC plate (hexane:EtOAc=3:1) to obtain 49 KK-061 (37.9 mg, 51%) as a colorless oil.

49 KK-061: $[\alpha]_D^{27}$+39.0 (c 2.92, $CHCl_3$); IR (neat) 3430, 1464, 1380, 1177, 1043, 848, 763 cm-1; $^1$H NMR (600 MHz, $CDCl_3$) δ 0.55 (s, 3H), 0.95 (d, J=7.2 Hz, 3H), 1.26-2.04 (m, 23H), 2.84 (dd, J=4.2, 13.2 Hz, 1H), 5.21-5.34 (m, 3H), 7.14-7.18 (m, 2H), 8.11-8.14 (m, 2H); $^{13}$C NMR (150 MHz, $CDCl_3$) δ 11.8, 18.6, 22.0, 23.3, 23.6, 26.8, 27.4 (t, J=24.5 Hz), 27.4, 29.0, 35.6, 40.1, 45.8, 50.2, 55.6, 56.1, 73.3 (t, J=27.3 Hz), 111.6, 115.9 (d, J=23.0 Hz), 123.9, 125.5 (t, J=236.9 Hz), 128.8 (d, J=8.6 Hz), 147.5, 163.9 (d, J=248.4 Hz), 164.2; HRMS (ESI$^+$) calcd for $C_{27}H_{37}N_4OF_3Na$ [M+Na]$^+$ 513.2812, found 513.2812.

p-Toluenesulfonic acid monohydrate (94.6 mg, 0.497 mmol) was added to a solution of the above more polar crude product in MeOH (5 mL). The mixture was stirred at room temperature for 120 min under air. After the reaction was quenched with $H_2O$ and saturated aqueous $NaHCO_3$ at room temperature, the mixture was extracted with EtOAc three times, washed with brine, dried over $Na_2SO_4$, filtered, and concentrated. The residue was purified on a preparative silica gel TLC plate (hexane:EtOAc=1:1) to obtain 51 KK-062 (16.9 mg, 23%) as a colorless oil.

51 KK-062: $[\alpha]_D^{27}$+45.2 (c 1.30, $CHCl_3$); IR (neat) 3399, 1479, 1384, 1240, 1176, 1017, 851, 698 cm-1; $^1$H NMR (600 MHz, $CDCl_3$) δ 0.47 (s, 3H), 0.93 (d, J=6.6 Hz, 3H), 1.242.01 (m, 23H), 2.54-2.57 (m, 1H), 5.05-5.15 (m, 3H), 7.23-7.25 (m, 2H), 7.69-7.72 (m, 2H); $^{13}$C NMR (150 MHz, $CDCl_3$) δ 11.8, 18.6, 22.0, 23.1, 23.6, 26.7, 27.3, 27.4 (t, J=24.5 Hz), 28.9, 35.6, 39.9, 45.6, 45.7, 55.5, 56.1, 73.3 (t, J=26.6 Hz), 112.8, 116.5 (d, J=21.6 Hz), 120.4 (d, J=2.9 Hz), 125.5 (t, J=245.7 Hz), 131.0 (d, J=8.6 Hz), 146.6, 153.3, 164.4 (d, J=251.4 Hz); HRMS (ESI$^+$) calcd for $C_{27}H_{37}N_4OF_3Na$ [M+Na]$^+$ 513.2812, found 513.2816.

Examples 36 and 37

(6R)-3,3-difluoro-6-[(1R,3aS,7aR,E)-4-{2-[5-(4-methylphenyl)-2H-tetrazol-2-yl]ethylidene}-7a-methyloctahydro-1H-inden-1-yl]-2-methylheptan-2-ol (52)

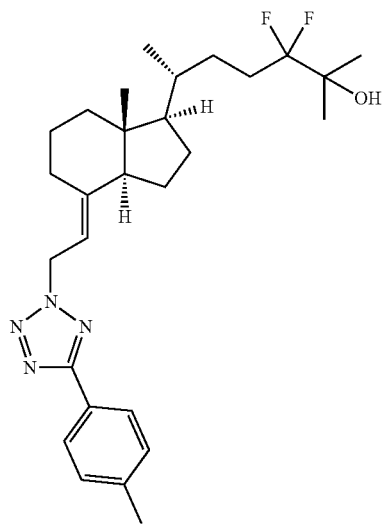

(6R)-3,3-difluoro-6-[(1R,3aS,7aR,E)-4-{2-[5-(4-methylphenyl)-1H-tetrazol-1-yl]ethylidene}-7a-methyloctahydro-1H-inden-1-yl]-2-methylheptan-2-ol (53)

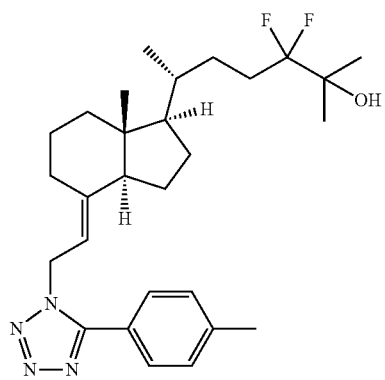

To a solution of 5-(4-methylphenyl)-1H-tetrazole (29.5 mg, 0.184 mmol), Ph₃P (52.7 mg, 0.201 mmol), and 24,24-difluoro-CD-ring (44) (42.4 mg, 0.092 mmol) in CH₂Cl₂ (3 mL) was added diisopropyl azodicarboxylate (88 µL, 1.9 M in toluene, 0.166 mmol) at 0° C., and the mixture was stirred at 0° C. for 5 min and then at room temperature for 40 min. The mixture was evaporated in vacuo. The residue was roughly purified by flash column chromatography on silica gel (hexane:EtOAc=5:1-3:1) to obtain crude products (less polar and more polar products).

p-Toluenesulfonic acid monohydrate (109.6 mg, 0.576 mmol) was added to a solution of the above less polar crude product in MeOH (5 mL) and CH₂Cl₂ (2 mL). The mixture was stirred at room temperature for 1 h under air. p-Toluenesulfonic acid monohydrate (109.6 mg, 0.576 mmol) was added to a mixture and stirred at the same temperature for a further 30 min. After the reaction was quenched with H₂O and saturated aqueous NaHCO₃ at room temperature, the mixture was extracted with CH₂Cl₂ three times, dried over Na₂SO₄, filtered, and concentrated.

The residue was purified on a preparative silica gel TLC plate (hexane:EtOAc=3:1) to obtain 52 (13.5 mg, 30%) as a colorless oil.

52: $[\alpha]_D^{27}$+35.9 (c 1.04, CHCl₃); IR (neat) 3442, 1464, 1380, 1176, 1041, 1017, 830, 754 cm⁻¹; ¹H NMR (600 MHz, CDCl₃) δ 0.54 (s, 3H), 0.94 (d, J=6.6 Hz, 3H), 1.25-2.04 (m, 23H), 2.41 (s, 3H), 2.83-2.85 (m, 1H), 5.21-5.35 (m, 3H), 7.28 (d, J=7.8 Hz, 2H), 8.02 (d, J=7.8 Hz, 2H); ¹³C NMR (150 MHz, CDCl₃) δ 11.8, 18.6, 21.5, 22.0, 23.3, 23.6, 26.8, 27.4 (t, J=24.4 Hz), 27.4, 29.1, 35.6, 40.1, 45.8, 50.1, 55.6, 56.1, 73.3 (t, J=26.6 Hz), 111.8, 124.8, 125.5 (t, J=246.3 Hz), 126.7, 129.5, 140.3, 147.7, 165.1; HRMS (ESI⁺) calcd for C₂₈H₄₀N₄OF₂Na [M+Na]⁺ 509.3062, found 509.3075.

p-Toluenesulfonic acid monohydrate (203.6 mg, 1.07 mmol) was added to a solution of the above more polar crude product in MeOH (5 mL) and CH₂Cl₂ (2 mL). The mixture was stirred at room temperature for 70 min under air. After the reaction was quenched with H₂O and saturated aqueous NaHCO₃ at room temperature, the mixture was extracted with CH₂Cl₂ three times, dried over Na₂SO₄, filtered, and concentrated. The residue was purified on a preparative silica gel TLC plate (hexane:EtOAc=1:1) to obtain 53 (12.7 mg, 28%) as a colorless oil.

53: $[\alpha]_D^{27}$+41.3 (c 0.98, CHCl₃); IR (neat) 3418, 1479, 1380, 1176, 1013, 826, 759 cm⁻¹; ¹H NMR (600 MHz, CDCl₃) δ 0.48 (s, 3H), 0.94 (d, J=7.2 Hz, 3H), 1.24-2.01 (m, 23H), 2.45 (s, 3H), 2.56-2.58 (m, 1H), 5.04-5.15 (m, 3H), 7.34 (d, J=7.2 Hz, 2H), 7.59 (d, J=7.2 Hz, 2H); ¹³C NMR (150 MHz, CDCl₃) δ 11.8, 18.6, 21.5, 22.1, 23.1, 23.6, 26.7, 27.3, 27.4 (t, J=24.5 Hz), 28.9, 35.6, 40.0, 45.6, 45.6, 55.5, 56.1, 73.3 (t, J=27.3 Hz), 113.1, 121.2, 125.4 (t, J=245.6 Hz), 128.7, 129.8, 141.6, 146.2, 154.1; HRMS (ESI⁺) calcd for C₂₈H₄₀N₄OF₂Na [M+Na]⁺ 509.3062, found 509.3079.

Examples 38 and 39

(6R)-3,3-Difluoro-6-[(1R,3aS,7aR,E)-4-{2-[5-(4-trifluoromethylphenyl)-2H-tetrazol-2-yl]ethylidene}-7a-methyloctahydro-1H-inden-1-yl]-2-methylheptan-2-ol (54)

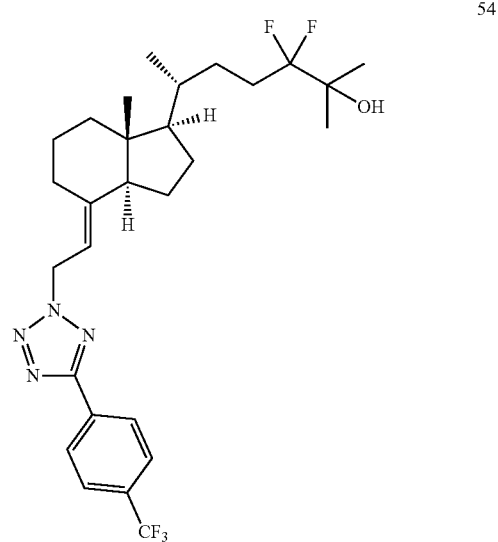 [SMILES: C[C@H](CCC(F)(F)C(C)(C)O)[C@H]1CC[C@H]2/C(=C/Cn3nnc(-c4ccc(C(F)(F)F)cc4)n3)CCC[C@]12C]

(6R)-3,3-Difluoro-6-[(1R,3aS,7aR,E)-4-{2-[5-(4-trifluoromethylphenyl)-1H-tetrazol-1-yl]ethylidene}-7a-methyloctahydro-1H-inden-1-yl]-2-methylheptan-2-ol (55)

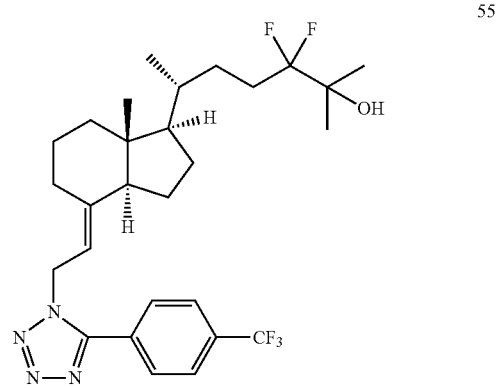 [SMILES: C[C@H](CCC(F)(F)C(C)(C)O)[C@H]1CC[C@H]2/C(=C/Cn3nnnc3-c3ccc(Cl)cc3)CCC[C@]12C]

To a solution of 5-(4-trifluoromethylphenyl)-1H-tetrazole (61.5 mg, 0.287 mmol), Ph₃P (72.2 mg, 0.275 mmol), and 24,24-difluoro-CD-ring (44) (60.1 mg, 0.131 mmol) in CH₂Cl₂ (8 mL) was added diisopropyl azodicarboxylate (124 µL, 1.9 M in toluene, 0.235 mmol) at 0° C., and the mixture was stirred at 0° C. for 70 min. The mixture was evaporated in vacuo, and the residue was roughly purified by flash column chromatography on silica gel (hexane:EtOAc=4:1) to obtain crude products (less polar and more polar products).

p-Toluenesulfonic acid monohydrate (386.8 mg, 2.03 mmol) was added to a solution of the above less polar crude product in MeOH (5 mL) and CH$_2$Cl$_2$ (2 mL). The mixture was stirred at room temperature for 35 min under air. After the reaction was quenched with H$_2$O and saturated aqueous NaHCO$_3$ at room temperature, the mixture was extracted with CH$_2$Cl$_2$ three times, dried over Na$_2$SO$_4$, filtered, and concentrated. The residue was purified on a preparative silica gel TLC plate (hexane:EtOAc=3:1) to obtain 54 (41.4 mg, 58%) as a white powder.

54: [α]$_D^{27}$+35.2 (c 3.17, CHCl$_3$); IR (neat) 3431, 1471, 1324, 1173, 1133, 1066, 858 cm$^{-1}$; $^1$H NMR (600 MHz, CDCl$_3$) δ 0.55 (s, 3H), 0.95 (d, J=6.0 Hz, 3H), 1.26-2.05 (m, 23H), 2.83-2.86 (m, 1H), 5.27-5.35 (m, 3H), 7.74 (d, J=8.1 Hz, 2H), 8.26 (d, J=8.1 Hz, 2H); $^{13}$C NMR (150 MHz, CDCl$_3$) δ 11.8, 18.6, 22.0, 23.4, 23.56, 26.8, 27.4, 27.4 (t, J=24.4 Hz), 29.1, 35.6, 40.1, 45.9, 50.3, 55.6, 56.1, 73.3 (t, J=27.2 Hz), 111.5, 123.9 (q, J=270.0 Hz), 125.5 (t, J=246.9 Hz), 125.8, 127.0, 131.0, 131.9 (q, J=31.7 Hz), 148.3, 163.8; HRMS (ESI$^+$) calcd for C$_{28}$H$_{37}$N$_4$OF$_5$Cl [M+Cl]$^-$ 575.2582, found 575.2577.

p-Toluenesulfonic acid monohydrate (411.7 mg, 2.05 mmol) was added to a solution of the above more polar crude product in MeOH (5 mL) and CH$_2$Cl$_2$ (6 mL). The mixture was stirred at room temperature for 60 min under air. After the reaction was quenched with H$_2$O and saturated aqueous NaHCO$_3$ at room temperature, the mixture was extracted with CH$_2$Cl$_2$ three times, dried over Na$_2$SO$_4$, filtered, and concentrated. The residue was purified on a preparative silica gel TLC plate (hexane:EtOAc=1:1) to obtain 55 (15.1 mg, 21%) as a white powder.

55: [α]$_D^{27}$+40.8 (c 1.16, CHCl$_3$); IR (neat) 3522, 1459, 1328, 1173, 1129, 1073, 858 cm$^{-1}$; $^1$H NMR (400 MHz, CDCl$_3$) δ 0.45 (s, 3H), 0.93 (d, J=6.4 Hz, 3H), 1.22-2.10 (m, 23H), 2.53-2.57 (m, 1H), 5.04-5.20 (m, 3H), 7.82 (d, J=8.7 Hz, 2H), 7.85 (d, J=8.2 Hz, 2H); $^{13}$C NMR (100 MHz, CDCl$_3$) δ 11.8, 18.6, 22.0, 23.4, 23.55, 26.7, 27.3, 27.3 (t, J=24.8 Hz), 28.9, 35.6, 39.9, 45.6, 45.9, 55.5, 56.1, 73.3 (t, J=27.2 Hz), 112.5, 123.5 (q, J=271.7 Hz), 125.4 (t, J=246.0 Hz), 126.1, 127.8, 129.3, 133.1 (q, J=32.7 Hz), 146.9, 153.0; HRMS (ESI$^+$) calcd for C$_{28}$H$_{37}$N$_4$OF$_5$Cl [M+Cl]$^-$ 575.2582, found 575.2590.

Examples 40 and 41

(6R)-3,3-Difluoro-6-[(1R,3aS,7aR,E)-4-{2-[5-(4-chlorophenyl)-2H-tetrazol-2-yl]ethylidene}-7a-methyloctahydro-1H-inden-1-yl]-2-methylheptan-2-ol (56)

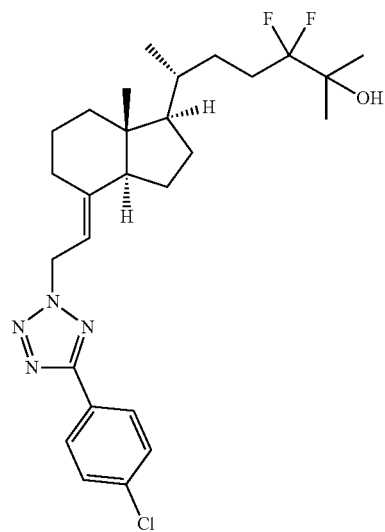

56

(6R)-3,3-Difluoro-6-[(1R,3aS,7aR,E)-4-{2-[5-(4-chlorophenyl)-1H-tetrazol-1-yl]ethylidene}-7a-methyloctahydro-1H-inden-1-yl]-2-methylheptan-2-ol (57)

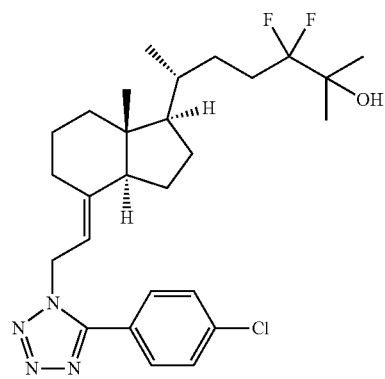

57

To a solution of 5-(4-chlorophenyl)-1H-tetrazole (44.7 mg, 0.248 mmol), Ph$_3$P (67.6 mg, 0.258 mmol), and 24,24-difluoro-CD-ring (44) (49.8 mg, 0.109 mmol) in CH$_2$Cl$_2$ (8 mL) was added diisopropyl azodicarboxylate (103 μL, 1.9 M in toluene, 0.196 mmol) at 0° C., and the mixture was stirred at the same temperature for 110 min. The mixture was evaporated in vacuo, and the residue was roughly purified by flash column chromatography on silica gel (hexane EtOAc=5:1) to obtain crude products (less polar and more polar products).

p-Toluenesulfonic acid monohydrate (435.3 mg, 2.29 mmol) was added to a solution of the above less polar crude product in MeOH (5 mL) and CH$_2$Cl$_2$ (5 mL). The mixture was stirred at room temperature for 1 h under air. After the reaction was quenched with H$_2$O and saturated aqueous NaHCO$_3$ at room temperature, the mixture was extracted with CH$_2$Cl$_2$ three times, dried over Na$_2$SO$_4$, filtered, and concentrated. The residue was purified on a preparative silica gel TLC plate (hexane:EtOAc=3:1) to obtain 56 (31.4 mg, 57%) as a colorless oil.

56: $[\alpha]_D^{27}$+41.4 (c 2.42, CHCl$_3$); IR (neat) 3414, 1456, 1326, 1175, 1093, 1017, 841, 759 cm$^{-1}$; $^1$H NMR (400 MHz, CDCl$_3$) δ 0.54 (s, 3H), 0.94 (d, J=6.4 Hz, 3H), 1.23-2.05 (m, 23H), 2.81-2.85 (m, 1H), 5.20-5.35 (m, 3H), 7.45 (dt, 2.3, 8.2 Hz, 2H), 8.07 (dt, 2.3, 8.7 Hz, 2H); $^{13}$C NMR (100 MHz, CDCl$_3$) δ 11.8, 18.6, 22.0, 23.3, 23.5, 26.7, 27.4 (t, J=24.8 Hz), 29.0, 35.6, 40.1, 45.8, 50.2, 55.6, 56.1, 73.3 (t, J=27.2 Hz), 111.6, 125.5 (t, J=246.0 Hz), 126.1, 128.0, 129.1, 136.1, 148.0, 164.1; HRMS (ESI$^+$) calcd for C$_{27}$H$_{37}$N$_4$OF$_2$ClNa[M+Na]$^+$ 529.2516, found 529.2531.

p-Toluenesulfonic acid monohydrate (389.5 mg, 2.05 mmol) was added to a solution of the above more polar crude product in MeOH (5 mL) and CH$_2$Cl$_2$ (5 mL). The mixture was stirred at room temperature for 85 min under air. After the reaction was quenched with H$_2$O and saturated aqueous NaHCO$_3$ at room temperature, the mixture was extracted with CH$_2$Cl$_2$ three times, dried over Na$_2$SO$_4$, filtered, and concentrated. The residue was purified on a preparative silica gel TLC plate (hexane:EtOAc=1:1) to obtain 57 (15.3 mg, 28%) as a colorless oil.

57: $[\alpha]_D^{27}$+43.0 (c 1.18, CHCl$_3$); IR (neat) 3423, 1471, 1380, 1174, 1093, 1013, 838, 739 cm$^{-1}$; $^1$H NMR (400 MHz, CDCl$_3$) δ 0.47 (s, 3H), 0.93 (d, J=6.4 Hz, 3H), 1.24-2.05 (m, 23H), 2.54-2.58 (m, 1H), 5.03-5.18 (m, 3H), 7.53 (dt, J=2.1, 8.2 Hz, 2H), 7.65 (dt, J=2.1, 8.7 Hz, 2H); $^{13}$C NMR (100 MHz, CDCl$_3$) δ 11.8, 18.6, 22.0, 23.1, 23.5, 26.7, 27.3, 27.3 (t, J=24.3 Hz), 28.9, 35.6, 39.9, 45.6, 45.8, 55.5, 56.1, 73.3 (t, J=27.2 Hz), 112.8, 122.6, 125.4 (t, J=246.0 Hz), 129.5, 130.1, 137.6, 146.7, 153.2; HRMS (ESI$^+$) calcd for C$_{27}$H$_{37}$N$_4$OF$_2$ClNa [M+Na]$^+$ 529.2516, found 529.2510.

Examples 42 and 43

(6R)-3,3-difluoro-6-[(1R,3aS,7aR,E)-4-{2-[5-(3-methylphenyl)-2H-tetrazol-2-yl]ethylidene}-7a-methyloctahydro-1H-inden-1-yl]-2-methylheptan-2-ol (58)

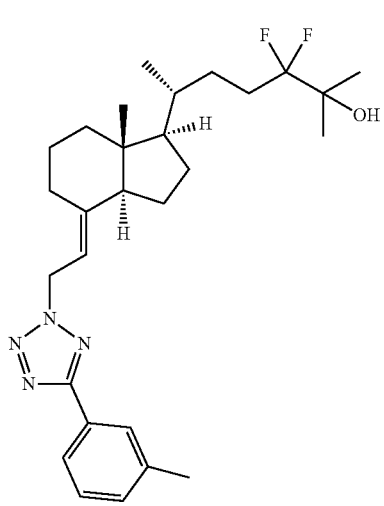

58

(6R)-3,3-difluoro-6-[(1R,3aS,7aR,E)-4-{2-[5-(3-methylphenyl)-1H-tetrazol-1-yl]ethylidene}-7a-methyloctahydro-1H-inden-1-yl]-2-methylheptan-2-ol (59)

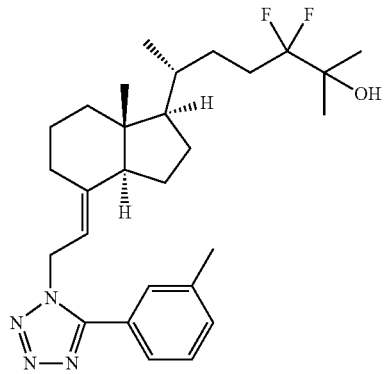

59

To a solution of 5-(3-methylphenyl)-1H-tetrazole (28.6 mg, 0.179 mmol), Ph$_3$P (47.8 mg, 0.182 mmol), and 24,24-difluoro-CD-ring (44) (51.4 mg, 0.112 mmol) in CH$_2$Cl$_2$ (8 mL) was added diisopropyl azodicarboxylate (83 μL, 1.9 M in toluene, 0.157 mmol) at 0° C., and the mixture was stirred at 0° C. for 5 min and then at room temperature for 20 min. To the mixture were added diisopropyl azodicarboxylate (83 μL, 1.9 M in toluene, 0.157 mmol) and Ph$_3$P (83.7 mg, 0.319 mmol) and stirred at room temperature for 40 min. The mixture was evaporated in vacuo, and the residue was roughly purified on a preparative silica gel TLC plate (hexane EtOAc=3:1) to obtain crude products (less polar and more polar products).

p-Toluenesulfonic acid monohydrate (584.6 mg, 3.07 mmol) was added to a solution of the above less polar crude product in MeOH (10 mL) and CH$_2$Cl$_2$ (5 mL). The mixture was stirred at room temperature for 90 min under air. After the reaction was quenched with H$_2$O and saturated aqueous NaHCO$_3$ at room temperature, the mixture was extracted with CH$_2$Cl$_2$ three times, dried over Na$_2$SO$_4$, filtered, and concentrated. The residue was purified on a preparative silica gel TLC plate (hexane:EtOAc=2:1) to obtain 58 (38.1 mg, 70%) as a colorless oil.

58: $[\alpha]_D^{27}$+23.1 (c 2.93, CHCl$_3$); IR (neat) 3423, 1471, 1380, 1180, 1017, 858, 754 cm$^{-1}$; $^1$H NMR (600 MHz, CDCl$_3$) δ 0.55 (s, 3H), 0.95 (d, J=6.0 Hz, 3H), 1.26-2.06 (m, 23H), 2.43 (s, 3H), 2.83-2.86 (m, 1H), 5.22-5.35 (m, 3H), 7.27 (d, J=7.8 Hz, 1H), 7.37 (t, J=7.8 Hz, 2H), 7.93 (d, J=7.8 Hz, 1H), 7.97 (s, 1H); $^{13}$C NMR (150 MHz, CDCl$_3$) δ 11.8, 18.6, 21.4, 22.0, 23.3, 23.6, 26.8, 27.4 (t, J=24.4 Hz), 27.4, 29.0, 35.6, 40.1, 45.8, 50.2, 55.6, 56.1, 73.4 (t, J=27.3 Hz), 111.8, 123.9, 125.5 (t, J=246.3 Hz), 127.4, 127.5, 128.8, 130.9, 138.6, 147.8, 165.1; HRMS (ESI$^+$) calcd for C$_{28}$H$_{40}$N$_4$OF$_2$Na [M+Na]$^+$ 509.3062, found 509.3068.

p-Toluenesulfonic acid monohydrate (376.1 mg, 1.98 mmol) was added to a solution of the above more polar crude product in MeOH (10 mL) and CH$_2$Cl$_2$ (5 mL). The mixture was stirred at room temperature for 60 min under air. After the reaction was quenched with H$_2$O and saturated aqueous NaHCO$_3$ at room temperature, the mixture was extracted with CH$_2$Cl$_2$ three times, dried over Na$_2$SO$_4$, filtered, and concentrated. The residue was purified on a preparative silica gel TLC plate (hexane:EtOAc=1:2) to obtain 59 (11.0 mg, 20%) as a colorless oil.

59: $[\alpha]_D^{27}$+44.6 (c 0.85, CHCl$_3$); IR (neat) 3411, 1475, 1380, 1180, 1125, 1021, 918, 854, 739 cm$^{-1}$; $^1$H NMR (600 MHz, CDCl$_3$) δ 0.46 (s, 3H), 0.93 (d, J=6.0 Hz, 3H), 1.24-1.99 (m, 23H), 2.43 (s, 3H), 2.53-2.56 (m, 1H), 5.04-5.16 (m, 3H), 7.38 (d, J=7.8 Hz, 1H), 7.42 (t, J=7.8 Hz, 1H), 7.45 (d, J=7.8 Hz, 1H), 7.51 (s, 1H); $^{13}$C NMR (150 MHz, CDCl$_3$) δ 11.8, 18.6, 21.4, 22.0, 23.1, 23.6, 26.7, 27.3, 27.3 (t, J=24.5 Hz), 28.9, 35.6, 40.0, 45.5, 45.6, 55.5, 56.1, 73.3 (t, J=27.2 Hz), 113.0, 124.1, 125.4 (t, J=246.3 Hz), 128.9, 129.5, 139.2, 146.2, 154.2; HRMS (ESI$^+$) calcd for $C_{28}H_{40}N_4OF_2Na$ [M+Na]$^+$ 509.3062, found 509.3039.

Examples 44 and 45

(6R)-3,3-difluoro-6-[(1R,3aS,7aR,E)-4-{2-[5-(3,5-dichlorophenyl)-2H-tetrazol-2-yl]ethylidene}-7a-methyloctahydro-1H-inden-1-yl]-2-methylheptan-2-ol (60)

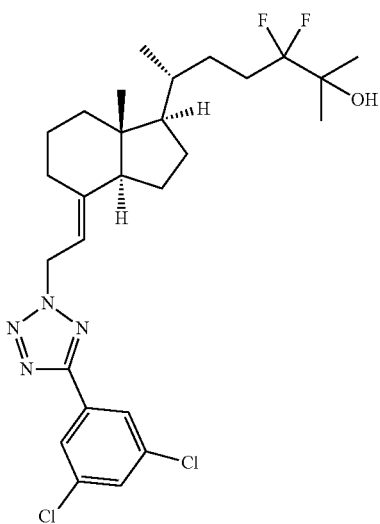

60

(6R)-3,3-difluoro-6-[(1R,3aS,7aR,E)-4-{2-[5-(3,5-dichlorophenyl)-1H-tetrazol-1-yl]ethylidene}-7a-methyloctahydro-1H-inden-1-yl]-2-methylheptan-2-ol (61)

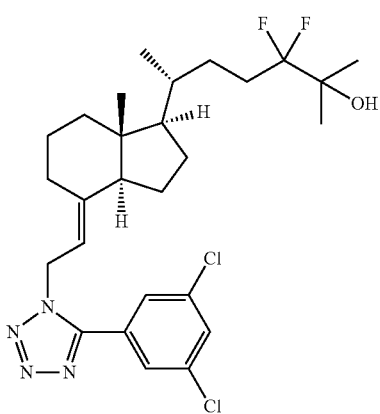

61

To a solution of 5-(3,5-dichlorophenyl)-1H-tetrazole (40.8 mg, 0.190 mmol), Ph$_3$P (47.6 mg, 0.181 mmol), and 24,24-difluoro-CD-ring (44) (40.8 mg, 0.089 mmol) in CH$_2$Cl$_2$ (4 mL) was added diisopropyl azodicarboxylate (138 μL, 1.9 M in toluene, 0.262 mmol) at 0° C., and the mixture was stirred at 0° C. for 35 min and then at room temperature for 25 min. The mixture was evaporated in vacuo, and the residue was roughly purified on a preparative silica gel TLC plate (hexane:EtOAc=3:1) to obtain crude products (less polar and more polar products).

p-Toluenesulfonic acid monohydrate (200.3 mg, 1.05 mmol) was added to a solution of the above less polar crude product in MeOH (10 mL) and CH$_2$Cl$_2$ (5 mL). The mixture was stirred at room temperature for 2 h under air. After the reaction was quenched with H$_2$O and saturated aqueous NaHCO$_3$ at room temperature, the mixture was extracted with EtOAc three times, washed with brine, dried over Na$_2$SO$_4$, filtered, and concentrated. The residue was purified on a preparative silica gel TLC plate (hexane:EtOAc=1:1) and followed by re-purification on a preparative silica gel TLC plate (hexane:EtOAc=2:1) to obtain 60 (27.6 mg, 57%) as a colorless oil.

60: $[\alpha]_D^{27}$+33.8 (c 2.12, CHCl$_3$); IR (neat) 3439, 1571, 1515, 1444, 1399, 1173, 1017, 862, 735 cm$^{-1}$; $^1$H NMR (600 MHz, CDCl$_3$) δ 0.55 (s, 3H), 0.95 (d, J=6.0 Hz, 3H), 1.24-2.05 (m, 23H), 2.81-2.84 (m, 1H), 5.25-5.34 (m, 3H), 7.45 (t, J=2.4 Hz, 1H), 8.07 (d, J=2.4 Hz, 2H); $^{13}$C NMR (150 MHz, CDCl$_3$) δ 11.8, 18.6, 22.0, 23.3, 23.6, 26.8, 27.4 (t, J=24.4 Hz), 27.4, 29.0, 35.6, 40.1, 45.9, 50.4, 55.6, 56.1, 73.4 (t, J=27.3 Hz), 111.4, 125.1, 125.5 (t, J=246.3 Hz), 130.0, 130.4, 135.6, 148.3, 162.9; HRMS (ESI$^-$) calcd for $C_{28}H_{37}N_4O_3F_2Cl_2$ [M+HCOO]$^+$ 585.2216, found 585.2215.

p-Toluenesulfonic acid monohydrate (580.1 mg, 3.05 mmol) was added to a solution of the above more polar crude product in MeOH (20 mL). The mixture was stirred at room temperature for 1 h under air. After the reaction was quenched with H$_2$O and saturated aqueous NaHCO$_3$ at room temperature, the mixture was extracted with EtOAc three times, washed with brine, dried over Na$_2$SO$_4$, filtered, and concentrated. The residue was purified on a preparative silica gel TLC plate (hexane:EtOAc=1:1) and followed by re-purification on a preparative silica gel TLC plate (hexane:EtOAc=1:1) to obtain 61 (15.0 mg, 31%) as a colorless oil.

61: $[\alpha]_D^{27}$+30.1 (c 1.15, CHCl$_3$); IR (neat) 3435, 1567, 1527, 1451, 1380, 1176, 1013, 905, 866, 727 cm$^{-1}$; $^1$H NMR (600 MHz, CDCl$_3$) δ 0.55 (s, 3H), 0.95 (d, J=6.0 Hz, 3H), 1.24-2.05 (m, 23H), 2.81-2.84 (m, 1H), 5.25-5.34 (m, 3H), 7.45 (t, J=2.4 Hz, 1H), 8.07 (d, J=2.4 Hz, 2H); $^{13}$C NMR (150 MHz, CDCl$_3$) δ 11.8, 18.6, 22.0, 23.1, 23.7, 26.7, 27.3, 27.3 (t, J=24.4 Hz), 28.9, 35.6, 39.9, 45.6, 46.1, 55.5, 56.1, 73.4 (t, J=27.3 Hz), 112.4, 125.4 (t, J=245.7 Hz), 127.0, 127.2, 131.2, 136.1, 147.1, 152.0; HRMS (ESI$^-$) calcd for $C_{28}H_{37}N_4O_3F_2Cl_2$ [M+HCOO]$^-$ 585.2216, found 585.2221.

Examples 46 and 47

(6R)-3,3-difluoro-6-[(1R,3aS,7aR,E)-4-{2-[5-(3-fluorophenyl)-2H-tetrazol-2-yl]ethylidene}-7a-methyloctahydro-1H-inden-1-yl]-2-methylheptan-2-ol (62)

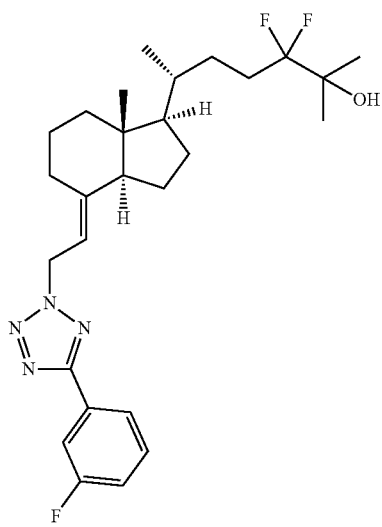

(6R)-3,3-difluoro-6-[(1R,3aS,7aR,E)-4-{2-[5-(3-fluorophenyl)-1H-tetrazol-1-yl]ethylidene}-7a-methyloctahydro-1H-inden-1-yl]-2-methylheptan-2-ol (63)

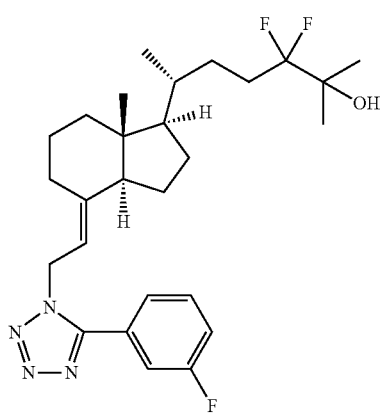

To a solution of 5-(3-fluorophenyl)-1H-tetrazole (36.4 mg, 0.222 mmol), Ph$_3$P (58.9 mg, 0.225 mmol), and 24,24-difluoro-CD-ring (44) (52.9 mg, 0.115 mmol) in CH$_2$Cl$_2$ (8 mL) was added diisopropyl azodicarboxylate (103 µL, 1.9 M in toluene, 0.196 mmol) at 0° C., and the mixture was stirred at 0° C. for 20 min. The mixture was evaporated in vacuo, and the residue was roughly purified by flash column chromatography on silica gel (hexane:EtOAc=5:1-2:1) to obtain crude products (less polar and more polar products).

p-Toluenesulfonic acid monohydrate (123.3 mg, 0.65 mmol) was added to a solution of the above less polar crude product in MeOH (10 mL). The mixture was stirred at room temperature for 1 h under air. After the reaction was quenched with H$_2$O and saturated aqueous NaHCO$_3$ at room temperature, the mixture was extracted with EtOAc three times, washed with brine and dried over Na$_2$SO$_4$, filtered, and concentrated. The residue was purified on a preparative silica gel TLC plate (hexane:EtOAc=2:1) to obtain 62 (34.8 mg, 62%) as a colorless oil.

62: $[\alpha]_D^{27}$+38.9 (c 2.68, CHCl$_3$); IR (neat) 3439, 1471, 1380, 1225, 1176, 1021, 763 cm$^{-1}$; $^1$H NMR (600 MHz, CDCl$_3$) δ 0.54 (s, 3H), 0.94 (d, J=6.0 Hz, 3H), 1.24-2.04 (m, 23H), 2.83-2.85 (m, 1H), 5.28-5.37 (m, 3H), 7.22 (dd, J=8.4, 10.2 Hz, 1H), 7.27 (t, J=7.5 Hz, 3H), 7.24-7.46 (m, 1H), 8.12 (td, J=1.8, 7.8 Hz, 3H); $^{13}$C NMR (150 MHz, CDCl$_3$) δ 11.8, 18.6, 22.0, 23.3, 23.5, 26.8, 27.3 (t, J=24.5 Hz), 27.3, 29.0, 35.6, 40.1, 45.8, 50.2, 55.6, 56.1, 73.3 (t, J=27.3 Hz), 111.5, 113.8 (d, J=24.5 Hz), 117.0 (d, J=21.5 Hz), 122.4 (d, J=2.9 Hz), 125.5 (t, J=246.3 Hz), 129.6 (d, J=8.7 Hz), 130.5 (d, J=8.6 Hz), 148.1, 163.0 (d, J=244.2 Hz), 164.0 (d, J=3.0 Hz); HRMS (ESI$^+$) calcd for C$_{27}$H$_{37}$N$_4$OF$_3$Na [M+Na]$^+$ 513.2812, found 513.2817.

p-Toluenesulfonic acid monohydrate (211.9 mg, 1.11 mmol) was added to a solution of the above more polar crude product in MeOH (10 mL). The mixture was stirred at room temperature for 40 min under air. After the reaction was quenched with H$_2$O and saturated aqueous NaHCO$_3$ at room temperature, the mixture was extracted with EtOAc three times, washed with brine and dried over Na$_2$SO$_4$, filtered, and concentrated. The residue was purified on a preparative silica gel TLC plate (hexane:EtOAc=1:1) to obtain 63 (10.2 mg, 18%) as a colorless oil.

63: $[\alpha]_D^{27}$+66.9 (c 0.79, CHCl$_3$); IR (neat) 3411, 1475, 1384, 1204, 1176, 1017, 739 cm$^{-1}$; $^1$H NMR (600 MHz, CDCl$_3$) δ 0.54 (s, 3H), 0.94 (d, J=6.0 Hz, 3H), 1.24-2.04 (m, 23H), 2.83-2.85 (m, 1H), 5.28-5.37 (m, 3H), 7.22 (dd, J=8.4, 10.2 Hz, 1H), 7.27 (t, J=7.5 Hz, 3H), 7.24-7.46 (m, 1H), 8.12 (td, J=1.8, 7.8 Hz, 3H); $^{13}$C NMR (150 MHz, CDCl$_3$) δ 11.8, 18.6, 22.0, 23.0, 23.6, 26.7, 27.3, 27.3 (t, J=24.5 Hz), 27.3, 28.9, 35.6, 39.9, 45.6, 45.9, 55.5, 56.1, 73.3 (t, J=26.6 Hz), 112.7, 116.1 (d, J=23.0 Hz), 118.3 (d, J=21.6 Hz), 124.6 (d, J=4.4 Hz), 125.4 (t, J=245.6 Hz), 126.1 (d, J=8.6 Hz), 131.0 (d, J=8.6 Hz), 146.7, 153.0, 162.7 (d, J=247.1 Hz); HRMS (ESI$^+$) calcd for C$_{27}$H$_{37}$N$_4$OF$_3$Na [M+Na]$^+$ 513.2812, found 513.2821.

Examples 48 and 49

(6R)-3,3-difluoro-6-[(1R,3aS,7aR,E)-4-{2-[5-(2-chlorophenyl)-2H-tetrazol-2-yl]ethylidene}-7a-methyloctahydro-1H-inden-1-yl]-2-methylheptan-2-ol (64)

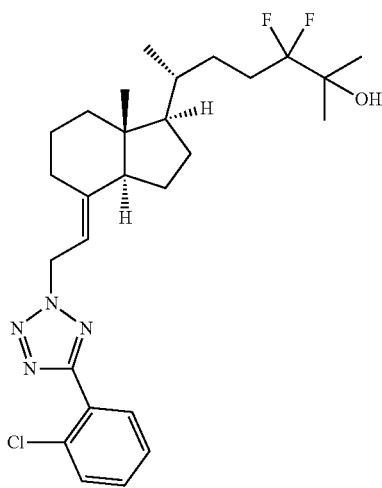

(6R)-3,3-difluoro-6-[(1R,3aS,7aR,E)-4-{2-[5-(2-chlorophenyl)-1H-tetrazol-1-yl]ethylidene}-7a-methyloctahydro-1H-inden-1-yl]-2-methylheptan-2-ol (65)

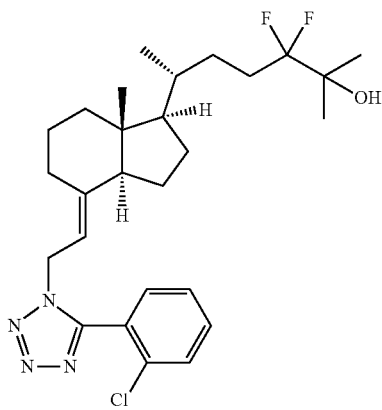

To a solution of 5-(2-chlorophenyl)-1H-tetrazole (39.9 mg, 0.221 mmol), Ph$_3$P (58.2 mg, 0.222 mmol), and 24,24-difluoro-CD-ring (44) (51.7 mg, 0.113 mmol) in CH$_2$Cl$_2$ (8 mL) was added diisopropyl azodicarboxylate (103 μL, 1.9 M in toluene, 0.196 mmol) at 0° C., and the mixture was stirred at 0° C. for 35 min. The mixture was evaporated in vacuo, and the residue was roughly purified by flash column chromatography on silica gel (hexane:EtOAc=5:1) to obtain crude products (less polar and more polar products).

p-Toluenesulfonic acid monohydrate (573.2 mg, 3.01 mmol) was added to a solution of the above less polar crude product in MeOH (20 mL). The mixture was stirred at room temperature for 5 h under air. After the reaction was quenched with H$_2$O and saturated aqueous NaHCO$_3$ at room temperature, the mixture was extracted with EtOAc three times, washed with brine and dried over Na$_2$SO$_4$, filtered, and concentrated. The residue was purified on a preparative silica gel TLC plate (hexane:EtOAc=3:1) to obtain 64 (22.7 mg, 40%) as a colorless oil.

64: [α]$_D^{27}$+37.7 (c 1.75, CHCl$_3$); IR (neat) 3435, 1446, 1380, 1176, 1125, 1073, 1038, 754 cm$^{-1}$; $^1$H NMR (400 MHz, CDCl$_3$) δ 0.54 (s, 3H), 0.94 (d, J=6.4 Hz, 3H), 1.24-2.05 (m, 23H), 2.83-2.87 (m, 1H), 5.29-5.39 (m, 3H), 7.35-7.42 (m, 2H), 7.52-7.54 (m, 1H), 7.91-7.96 (m, 1H); $^{13}$C NMR (100 MHz, CDCl$_3$) δ 11.8, 18.6, 22.0, 23.4, 23.6, 26.8, 27.4 (t, J=24.8 Hz), 27.4, 29.0, 35.6, 40.1, 45.8, 50.3, 55.6, 56.1, 73.3 (t, J=26.7 Hz), 111.6, 125.5 (t, J=246.0 Hz), 126.8, 126.8, 130.8, 130.9, 131.3, 133.1, 148.1, 163.2; HRMS (ESI$^+$) calcd for C$_{27}$H$_{37}$N$_4$OF$_2$ClNa [M+Na]$^+$ 529.2516, found 529.2519.

p-Toluenesulfonic acid monohydrate (580.7 mg, 3.05 mmol) was added to a solution of the above more polar crude product in MeOH (20 mL). The mixture was stirred at room temperature for 90 min under air. After the reaction was quenched with H$_2$O and saturated aqueous NaHCO$_3$ at room temperature, the mixture was extracted with EtOAc three times, washed with brine and dried over Na$_2$SO$_4$, filtered, and concentrated. The residue was purified on a preparative silica gel TLC plate (hexane:EtOAc=1:1) to obtain 65 (20.7 mg, 36%) as a colorless oil.

65: [α]$_D^{27}$+29.4 (c 1.59, CHCl$_3$); IR (neat) 3407, 1459, 1380, 1176, 1125, 1073, 1020, 767 cm$^{-1}$; $^1$H NMR (400 MHz, CDCl$_3$) δ 0.40 (s, 3H), 0.91 (d, J=6.9 Hz, 3H), 1.18-2.02 (m, 23H), 2.36-2.40 (m, 1H), 4.91-5.06 (m, 3H), 7.40-7.45 (m, 2H), 7.51-7.58 (m, 2H); $^{13}$C NMR (100 MHz, CDCl$_3$) δ 11.8, 18.6, 21.9, 23.1, 23.5, 26.7, 27.2, 27.3 (t, J=24.8 Hz), 28.5, 35.6, 40.0, 45.4, 55.4, 56.0, 73.3 (t, J=26.7 Hz), 112.0, 124.4, 125.4 (t, J=246.0 Hz), 127.2, 130.1, 131.9, 132.5, 133.9, 147.1, 152.2; HRMS (ESI$^+$) calcd for C$_{27}$H$_{37}$N$_4$OF$_2$ClNa [M+Na]$^+$ 529.2516, found 529.2531.

Examples 50 and 51

(6R)-3,3-difluoro-6-[(1R,3aS,7aR,E)-4-{2-[5-(2-fluorophenyl)-2H-tetrazol-2-yl]ethylidene}-7a-methyloctahydro-1H-inden-1-yl]-2-methylheptan-2-ol (66)

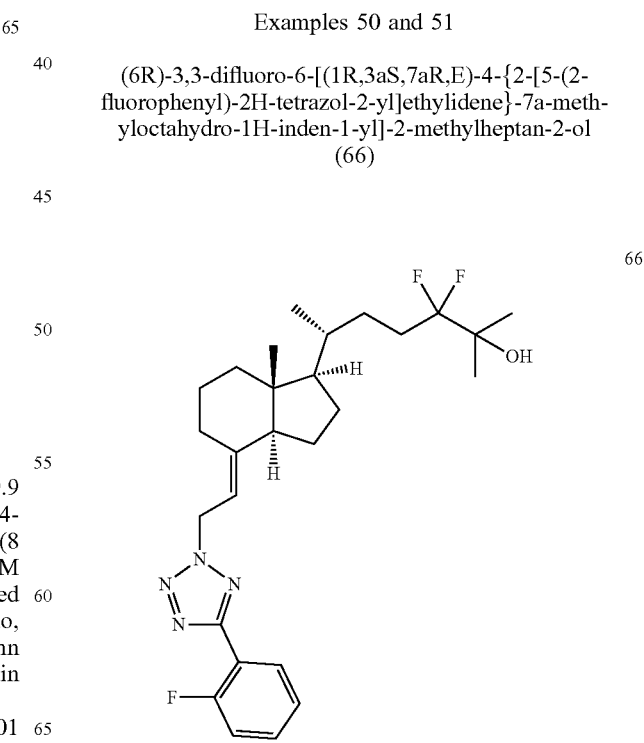

(6R)-3,3-difluoro-6-[(1R,3aS,7aR,E)-4-{2-[5-(2-fluorophenyl)-1H-tetrazol-1-yl]ethylidene}-7a-methyloctahydro-1H-inden-1-yl]-2-methylheptan-2-ol (67)

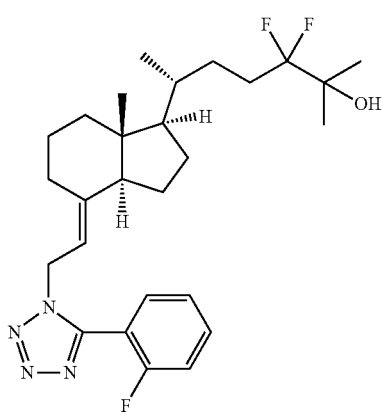

To a solution of 5-(2-fluorophenyl)-1H-tetrazole (36.5 mg, 0.222 mmol), Ph$_3$P (59.2 mg, 0.226 mmol), and 24,24-difluoro-CD-ring (44) (51.4 mg, 0.112 mmol) in CH$_2$Cl$_2$ (8 mL) was added diisopropyl azodicarboxylate (103 µL, 1.9 M in toluene, 0.196 mmol) at 0° C., and the mixture was stirred at 0° C. for 30 min. The mixture was evaporated in vacuo, and the residue was roughly purified by flash column chromatography on silica gel (hexane:EtOAc=5:1-2:1) to obtain crude products (less polar and more polar products). p-Toluenesulfonic acid monohydrate (585.7 mg, 3.08 mmol) was added to a solution of the above less polar crude product in MeOH (20 mL). The mixture was stirred at room temperature for 105 min under air. After the reaction was quenched with H$_2$O and saturated aqueous NaHCO$_3$ at room temperature, the mixture was extracted with EtOAc three times, washed with brine, dried over Na$_2$SO$_4$, filtered, and concentrated. The residue was purified on a preparative silica gel TLC plate (hexane:EtOAc=2:1) to obtain 66 (30.8 mg, 56%) as a colorless oil. 66: [α]$_D^{27}$+36.7 (c 2.37, CHCl$_3$); IR (neat) 3435, 1479, 1376, 1228, 1180, 1037, 754 cm$^{-1}$; $^1$H NMR (600 MHz, CDCl$_3$) δ 0.54 (s, 3H), 0.94 (d, J=6.0 Hz, 3H), 1.24-2.04 (m, 23H), 2.83-2.85 (m, 1H), 5.28-5.37 (m, 3H), 7.22 (dd, J=8.4, 10.2 Hz, 1H), 7.27 (t, J=7.5 Hz, 3H), 7.24-7.46 (m, 1H), 8.12 (td, J=1.8, 7.8 Hz, 3H); $^{13}$C NMR (150 MHz, CDCl$_3$) δ 11.8, 18.6, 22.0, 23.3, 23.6, 26.8, 27.3 (t, J=24.5 Hz), 27.4, 29.1, 35.6, 40.1, 45.8, 50.3, 55.6, 56.1, 73.3 (t, J=27.3 Hz), 111.6, 115.8 (d, J=11.4 Hz), 116.6 (d, J=20.1 Hz), 124.4 (d, J=4.2 Hz), 125.5 (t, J=246.3 Hz), 129.9, 131.1 (d, J=8.7 Hz), 148.0, 160.1 (d, J=254.3 Hz), 161.2 (d, J=4.4 Hz); HRMS (ESI$^+$) calcd for C$_{27}$H$_{37}$N$_4$OF$_3$ [M+Na]$^+$ 513.2812, found 513.2797.

p-Toluenesulfonic acid monohydrate (619.1 mg, 3.25 mmol) was added to a solution of the above more polar crude product in MeOH (20 mL). The mixture was stirred at room temperature for 1 h under air. After the reaction was quenched with H$_2$O and saturated aqueous NaHCO$_3$ at room temperature, the mixture was extracted with EtOAc three times, washed with brine, dried over Na$_2$SO$_4$, filtered, and concentrated. The residue was purified on a preparative silica gel TLC plate (hexane:EtOAc=1:1) to obtain 67 (21.6 mg, 39%) as a colorless oil. 67: [α]$_D^{27}$+38.0 (c 1.66, CHCl$_3$); IR (neat) 3423, 1479, 1384, 1217, 1173, 1021, 774, 739 cm$^{-1}$; $^1$H NMR (400 MHz, CDCl$_3$) δ 0.36 (s, 3H), 0.90 (d, J=6.4 Hz, 3H), 1.20-2.06 (m, 23H), 2.47-2.52 (m, 1H), 4.98-5.12 (m, 3H), 7.24-7.29 (m, 1H), 7.33 (td, J=1.8, 7.4 Hz, 1H), 7.56-7.62 (m, 1H); $^{13}$C NMR (100 MHz, CDCl$_3$) δ 11.7, 18.6, 21.9, 23.1, 23.5, 26.7, 27.3, 27.3 (t, J=24.3 Hz), 28.6, 35.6, 40.0, 45.5, 45.6, 45.7, 55.4, 56.0, 73.3 (t, J=27.2 Hz), 112.1, 112.9 (d, J=14.3 Hz), 116.3 (d, J=21.0 Hz), 125.0 (d, J=2.9 Hz), 125.4 (t, J=246.0 Hz), 131.8, 133.5 (d, J=7.6 Hz), 147.0, 150.1, 159.6 (d, J=248.8 Hz); HRMS (ESI$^+$) calcd for C$_{27}$H$_{37}$N$_4$OF$_3$Na [M+Na]$^+$ 513.2812, found 513.2825.

BIOLOGICAL EXAMPLES

Biological Example 1a and 1b

Luciferase Reporter Assay and VDR Reporter Assay

Cell Culture: CHO-K1 cells were maintained in medium A (1:1 mixture of Ham's F-12 medium and DMEM, supplemented with 100 units/mL penicillin, 100 µg/mL streptomycin sulfate, and 5% [v/v] fetal bovine serum) at 37° C. in a humidified 5% CO$_2$ incubator.

CHO-K1 cells were seeded into 96-well plates at 8×10$^3$ cells per well in medium A and incubated for 24 h. For SREBP reporter assay, cells were co-transfected with an SRE-1-driven luciferase reporter plasmid (pSRE-Luc) and an actin promoter-driven β-galactosidase expression plasmid (pAc-l3-gal) at a 20:1 ratio, using FuGENE HD Transfection Reagent (Promega) according to the manufacturer's protocol.

For VDR reporter assay, Cignal Vitamin D Receptor Reporter (QIAGEN) was transfected instead of pSRE-Luc.

After 20 h, the medium was changed to medium B (1:1 mixture of Ham's F-12 medium and DMEM, supplemented with 100 units/mL penicillin, 100 µg/mL streptomycin sulfate, 5% [v/v] lipid-depleted serum, 50 µM compactin (Tokyo Chemical Industry), and 50 µM lithium mevalonate (Sigma-Aldrich) containing the specific test compounds. After 24 h incubation, the cells in each well were lysed with 100 µL of 1× Reporter Lysis Buffer (Promega), and 50 µL of aliquots were used to measure luciferase and l3-gal activities. Luciferase activity was measured using the Steady-Glo Luciferase Assay System (Promega), and l3-gal activity was measured using the l3-Galactosidase Enzyme Assay System (Promega). Luciferase activity was normalized to l3-gal activity.

For the SREBP reporter assay, the assay was conducted at a single concentration of compound (5 µM) in a lipid-free medium where 25(OH)D$_3$ was found to display substantial inhibitory activity. CHO-K1 cells were treated with 5 µM of the compounds in a lipid-free medium. The same experiment using of 25(OH)D$_3$ (1) was performed as control. Values are mean±SD. Results are provided in FIGS. 1 and 3.

For the VDR assay, CHO-K1 cells were treated with 5 µM of the compounds in a lipid-free medium. The same experiment using 25(OH)D$_3$ (1) was performed as control. Values are mean±SD. Results are provided in FIGS. 2 and 4.

Biological Example 2

Short-Term In Vivo Model

Figure 5:
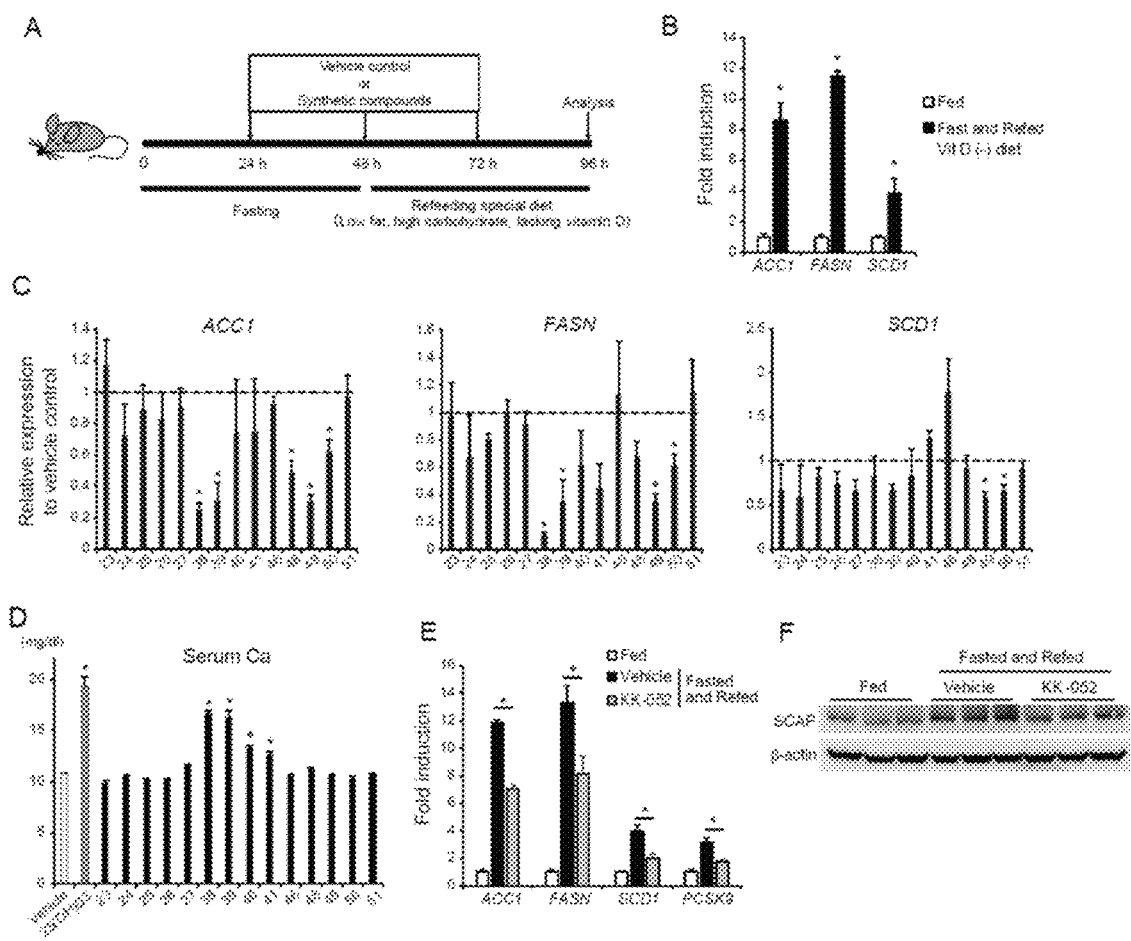
FIG. 5 shows the short-term in vivo evaluation of compounds disclosed herein: (A) Experimental protocol of the short-term screening system to assess the inhibitory effects of synthetic compounds on SREBP activation; (B) Relative mRNA levels of SREBP-responsive genes determined by real-time PCR in the livers obtained from the mice with free access to a normal diet or fasted and refed a special diet (means±SEM, n=3 per group), *p<0.05; (C) Expression levels of SREBP-responsive genes were determined by real-time PCR in the livers obtained from the mice treated with indicated compounds (10 mg/kg) according to the protocol illustrated in (A). (D) Serum calcium levels in the mice treated with vehicle, compounds, or 25(OH)D$_3$ (means±SEM, n=3 per group), *p<0.05; (E) Relative mRNA levels of SREBP-responsive genes determined by real-time PCR in the livers obtained from the indicated mice; (F) Western blot analysis of SCAP protein in the livers obtained from the indicated mice.

To quickly and simultaneously examine their SREBP inhibitory activity and VDR-derived calcemic activity in vivo, a short-term in vivo screening system of mice was established. With reference to the previous report (Horton, J. D. et al. *Proc. Natl. Acad. Sci. U.S.A.* 1998, 95, 5987-5992.), mice were fasted for 48 hours then refed a special diet (low fat, high carbohydrate diet, lacking in vitamin D) for 48 hours before sacrifice. Additional details are provided in FIG. 5A.

This system permitted the 4-day-long in vivo evaluation of 14 compounds (23-27, 38-41, 46, and 48-51), which exhibited excellent SREBP selectivity equally well in cultured cells.

C57BL/6 and oh/oh mice were purchased from CLEA Japan and Charles River Japan, Inc., respectively. Animal experiments were carried out at the University of Tokyo and Charles River Laboratories. Low fat, high carbohydrate diet, lacking vitamin D was custom made by Research Diets, Inc. Compounds disclosed herein and 25(OH)$D_3$ were dissolved in ethanol/Tween 20 (9:1) to obtain stock solution and then diluted 10-fold with PBS immediately before administration to mice.

10 mg/kg compounds or vehicle control were administered intraperitoneally once every 24 hours during the fasting and refeeding.

Following sacrifice, mouse livers were fixed in 10% neutral-buffered formalin, embedded in paraffin, sectioned, and stained with H&E. Hepatic lipids were extracted with chloroform/methanol (2:1 v/v), and TG and cholesterol contents were measured with Triglyceride Reagent Set (Pointe Scientific) and Cholesterol E (Wako), respectively. Serum levels of ALT, TG, glucose, cholesterol, and calcium were measured in SRL Inc. (Tokyo). All experiments were approved by the Ethics Committee for Animal Experimentation of the University of Tokyo and Charles River Laboratories Japan, and were conducted in accordance with the Guidelines for the Care and Use of Laboratory Animals.

Relative mRNA levels of SREBP-responsive genes were determined by real-time PCR in the livers obtained from the mice with free access to a normal diet or fasted and refed a special diet (means SEM, n=3 per group), *p<0.05. The expression levels of SREBP-responsive genes were significantly elevated in the livers after fasting and refeeding a special diet compared to the control mice with free access to a normal diet (FIG. 5B).

Expression levels of SREBP-responsive genes were determined by real-time PCR in the livers obtained from the mice treated with indicated compounds (10 mg/kg) according to the protocol illustrated in FIG. 5A. Data are expressed as relative expression to the mean value of vehicle-treated mouse liver (means±SEM, n=3 per group), *p<0.05 (FIG. 5C).

Serum calcium levels in the mice treated with vehicle, compounds, or 25(OH)$D_3$ were determined (means±SEM, n=3 per group), *p<0.05 (FIG. 5D).

Relative mRNA levels of SREBP-responsive genes were determined by real-time PCR in the livers obtained from the indicated mice Data are means±SEM (fed mice, n=3; others, n=6), *p<0.05 (FIG. 5E).

Western blot analysis of SCAP protein in the livers obtained from the indicated mice were obtained, (FIG. 5F).

Biological Example 3

Long-term In Vivo Model

Figure 7:
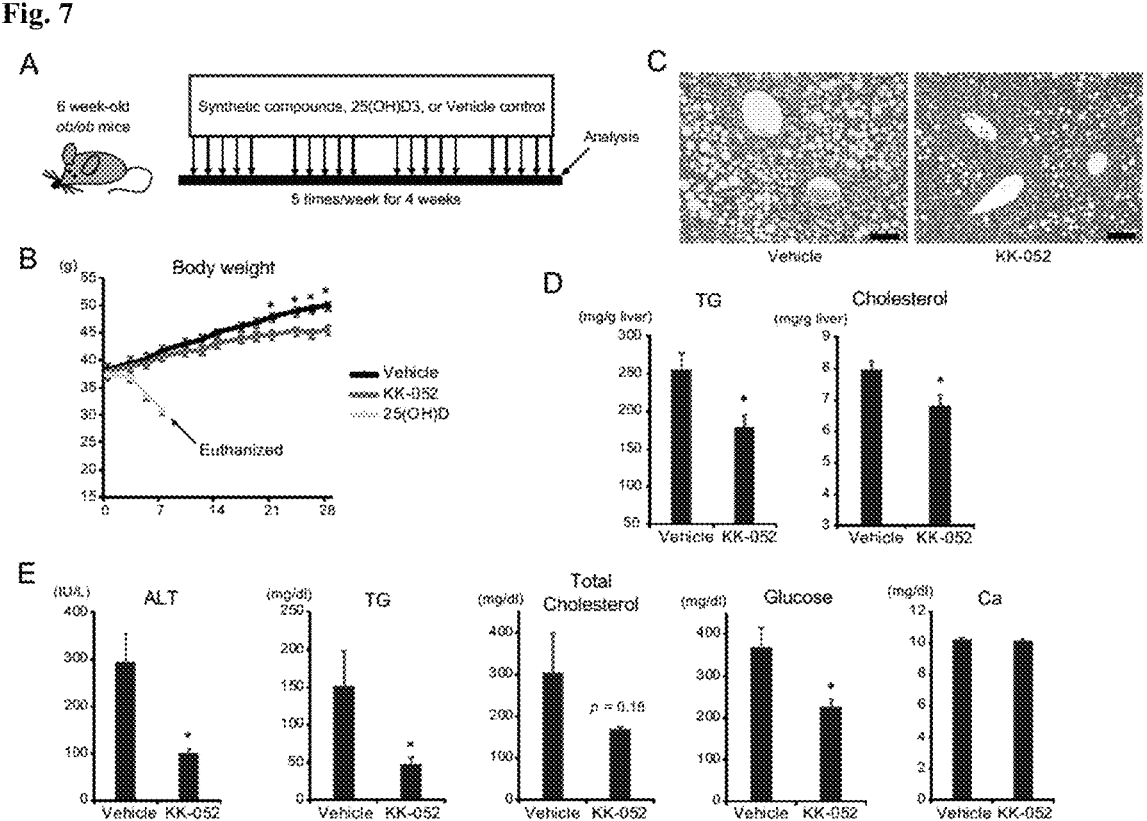
FIG. 7 shows long-term efficacy and safety data for KK-052 for the treatment of fatty liver using ob/ob mice.

To analyze the long-term efficacy and safety of KK-052 (50) for the treatment of fatty liver, leptin-deficient ob/ob mice that spontaneously exhibit fatty liver whose development depends on SREBP-mediated de novo lipogenesis were used (Moon et al. *Cell Metab.* 2012, 15, 240-246). Six-week-old ob/ob mice were treated with 10 mg/kg KK-052, 10 mg/kg 25(OH)$D_3$, or vehicle control 5 times per week for 4 weeks (FIG. 7A). All ob/ob mice treated with 25(OH)$D_3$ became sick due to hypercalcemia and euthanized at 1 week, while ob/ob mice treated with KK-052 appeared healthy until the end of the experiments.

Body weights of ob/ob mice were measured and data are given as means±SEM (25(OH)$D_3$, n=5; others, n=8), *p<0.05 (FIG. 7B).

H&E-stained images of the liver of KK-052- or vehicle-treated ob/ob mice (scale bar, 100 µm) are provided in FIG. 7C.

Hepatic TG and cholesterol contents were measured in KK-052- or vehicle-treated ob/ob mice (means±SEM), *p<0.05 (FIG. 7D).

Serum levels of ALT, TG, total cholesterol, glucose, and calcium were measured in KK-052- or vehicle-treated ob/ob mice (means±SEM), *p<0.05 (FIG. 7E).

Discussion of Results

Applicant has surprisingly found that during the course of screening an in-house collection of vitamin D analogs, it was observed that 14-epi-25(OH) $D_3$ (4):

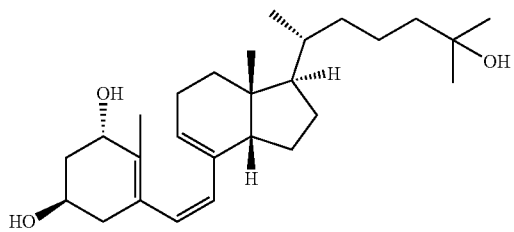 [SMILES: CC1=C(/C=C\C2=CCC[C@@]3(C)[C@@H]2CC[C@@H]3[C@H](C)CCCC(C)(C)O)C[C@@H](O)C[C@@H]1O]

(Maynard, D. F. et al. *J. Med. Chem.* 1994, 37, 2387-2393; and Sawada, D. et al. *Tetrahedron* 2010, 66, 5407-5423) compromised the expression of an SREBP-responsive luciferase reporter (Im, S-S. et al. *Cell Metab.* 2011, 13, 540-549) at a comparable level to 25(OH)$D_3$ (data not shown). The 14-epi isomer of 25(OH)$D_3$ has the tendency to isomerize via [1,7]-sigmatropic hydrogen shifts toward its previtamin form and has been demonstrated to display lower affinity to VDR and markedly decreased calcemic action (Maynard, D. F. et al. *J Med. Chem.* 1994, 37, 2387-2393). Applicant's observations indicated that the 25-hydroxy CD-ring, surprisingly, may be more critical than the A-ring for the SREBP inhibitory activity and that the entire hydroxylated A-ring, which is essential for the VDR activity, unexpectedly, could be replaced by a functional group that occupies similar volume to that of the A-ring, as represented in Compounds of Formula (I).

The ability of Compounds 10-33 to inhibit the expression of an SREBP-responsive reporter gene in which the expression of luciferase was controlled by SREBP in CHO-K1 cells was determined. Compounds 10-13, which harbor relatively small substituents at the C7 position, were generally inactive (FIG. 1). In contrast, analogues with relatively bulky cyclic substituents (compounds 14-18 and 21-29) displayed SREBP inhibitory activities comparable to that of 25(OH)$D_3$, although amides 19 and 20 had little effect. Surprisingly, the inhibitory activity was decreased when more extended substituents were introduced (compounds 30-33) (FIG. 1).

Figure 2:
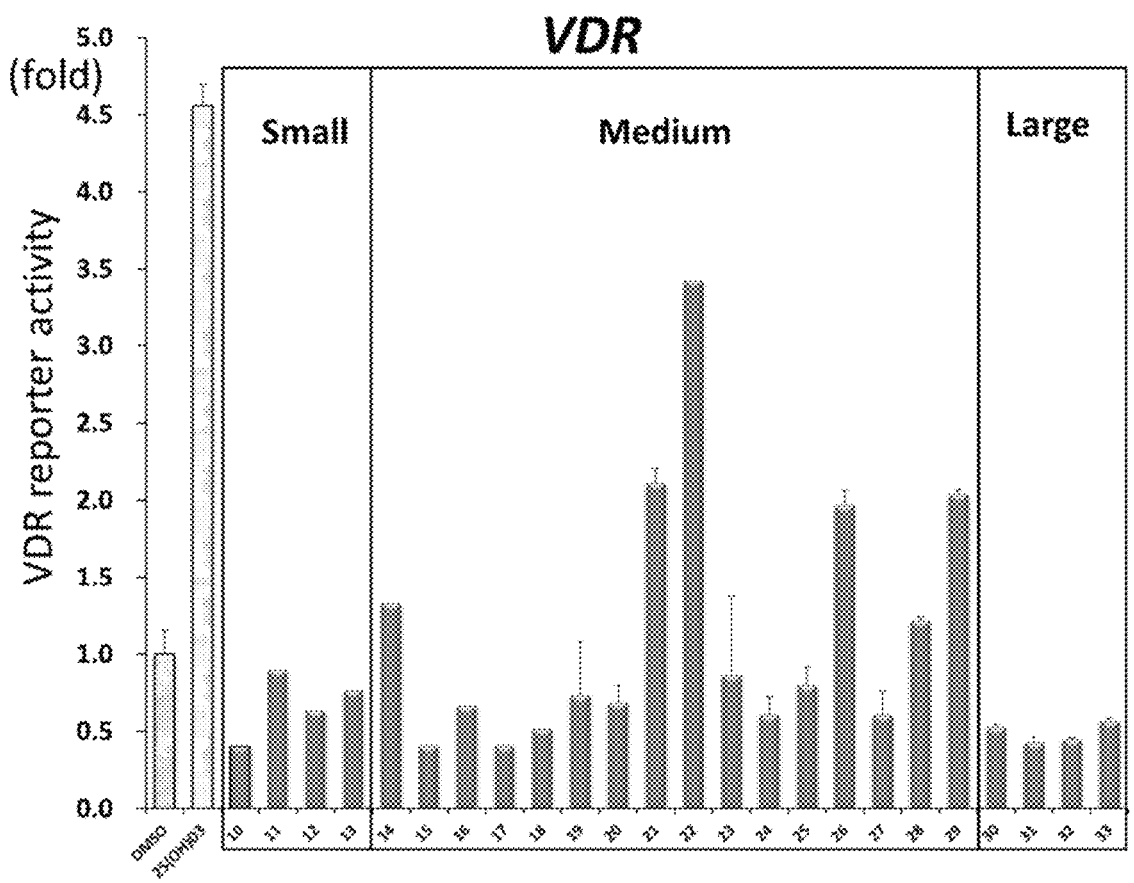
FIG. 2 shows effects of Compounds 10-33 on VDR activation.

The replacement of the 25(OH)$D_3$ A-ring with the unnatural structures overall diminished the ability to stimulate VDR, most likely due to the lack of the two hydroxy groups critical for the VDR interaction (FIG. 2). Although weakly, compounds 21, 22, 26 and 29 exhibited detectable VDR activity. The azole nitrogen of compounds 21, 22, and 26 and the hydroxy group of compound 29 may possibly mimic the hydroxy groups of $1\alpha,25(OH)D_3$ that form hydrogen bonds with the ligand binding pocket of VDR.

Compounds 23-25 displayed excellent selectivity to SREBP over VDR. However, as shown later in FIG. 5, compounds 23-25 failed to exhibit clear SREBP inhibitory activity in vivo, probably due to their low bioavailability. A number of attempts have been made in the literature to increase metabolic stability of vitamin D analogs against CYP24A1, a primary deactivating enzyme of $25(OH)D_3$ and $1\alpha,25(OH)_2D_3$ (Sakaki, T. et al. *Eur. J. Biochem.* 2000, 267, 6158-6165; Yasuda, K. *J. Steroid Biochem. Mol. Biol.* 2013, 133, 84-92; and St-Arnaud, R. CYP24A1: Structure, Function, and Physiological Role. In Vitamin D $3^{rd}$ ed.; Feldman, D., Pike, J. W., Adams, J. S., Eds.; Academic Press: London, 2011, pp 43-56). One notable approach used in the generation of clinically used vitamin D analogs is the introduction of fluorine atoms into the CD-ring side chain (Stem, P. H. et al. *Mol. Pharmacol.* 1981, 20, 460-462; Tanaka, Y. et al. *Arch. Biochem. Biophys.* 1984, 229, 348-354; Stem, P. H. et al. *J Pharmacol. Exp. Ther.* 1984, 229, 9-13).

Figure 3:
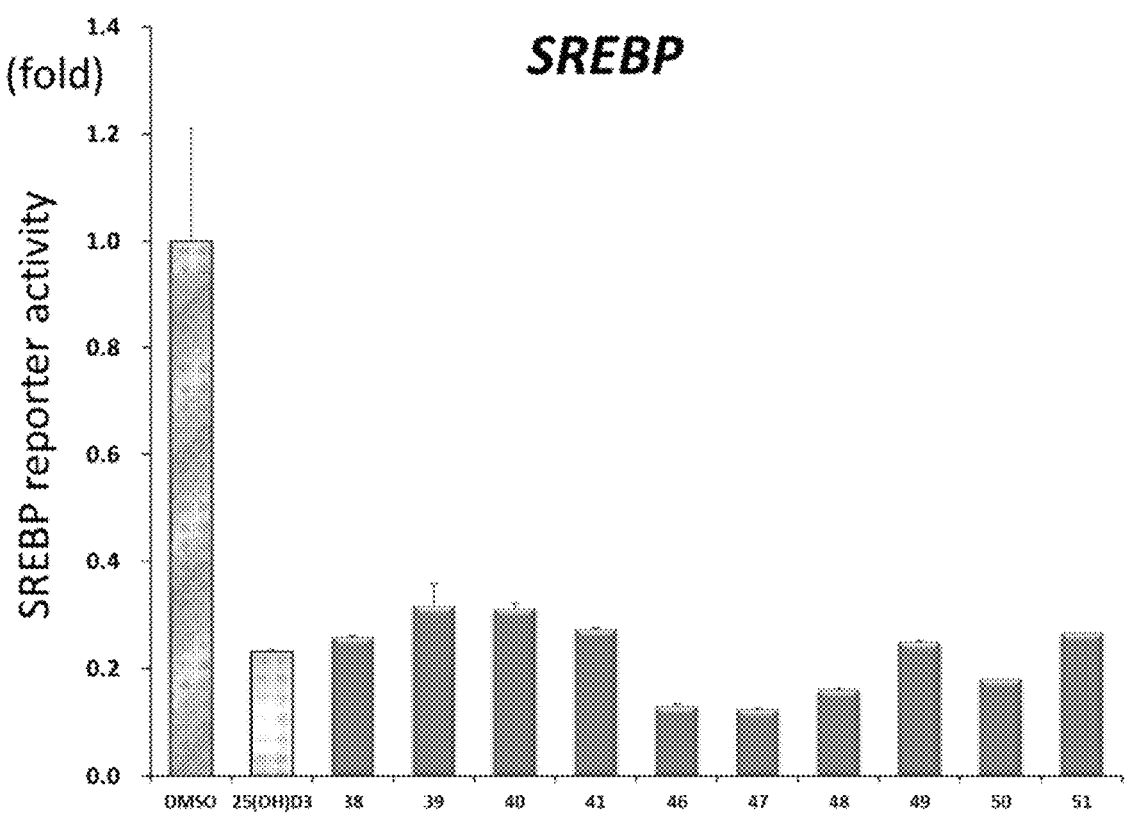
FIG. 3 shows the effects of Compounds 38-41 and 46-51 on the SREBP activation.
Figure 4:
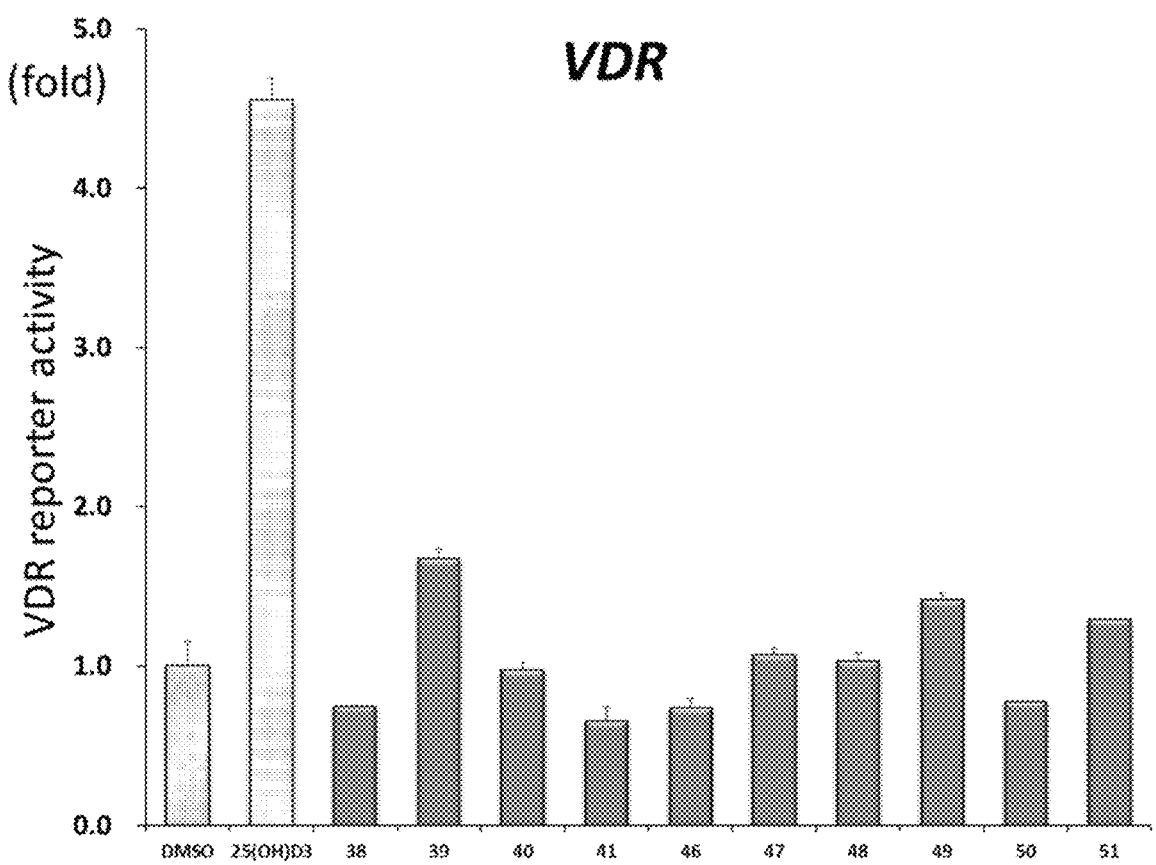
FIG. 4 shows the effects of 25(OH)D$_3$ (1) and Compounds 38-41 and 46-51 on VDR activation.

Relative to the parent compounds 23-25, the introduction of fluorine atoms, as in Compounds 38-41 and 46-51, did not negatively affect SREBP inhibitory activity. Generally, the introduction of fluorine atoms showed no effect on activation of VDR. Compounds 39, 47, 49, and 51, in which the para position of the benzene group is fluorinated, surprisingly, all maintained SREBP inhibitory activities and lacked in VDR activity (FIGS. 3 and 4).

As expected, administration of the same amount of $25(OH)D_3$ markedly increased serum calcium levels after 4 days, highlighting that the in vivo model, described in Biological Example 2, is valid for estimating the in vivo calcemic effects of the test compounds (FIG. 5D). Four fluorinated compounds (38, 39, 49, and 50) significantly suppressed the expression of two representative SREBP-response genes, ACC1 and FASN, compared to vehicle control; however, 38 and 39 also displayed the elevated levels of serum calcium, signifying that these compounds or their metabolites act on VDR in vivo under the test conditions (FIG. 5C, D).

These results encouraged the reevaluation of the effects of compounds 49 and 50, both of which mitigated the elevated expression of the three SREBP-responsive genes, ACC1, FASN, and SCD1, with no detectable increase of serum calcium levels. Repeated examination with increased number of mice underscored that 50 (KK-052) significantly mitigated the elevated expression of the four SREBP-responsive genes in a reproducible fashion (FIG. 5E). The expression levels of SCAP protein in the liver were increased after fasting and refeeding special diets. In accord with the reported SCAP-degrading activity of $25(OH)D_3$, the increased hepatic expression of SCAP was canceled by treatment with 50 (KK-052) (FIG. 5F). Thus, 50 (KK-052) was further investigated.

Figure 6:
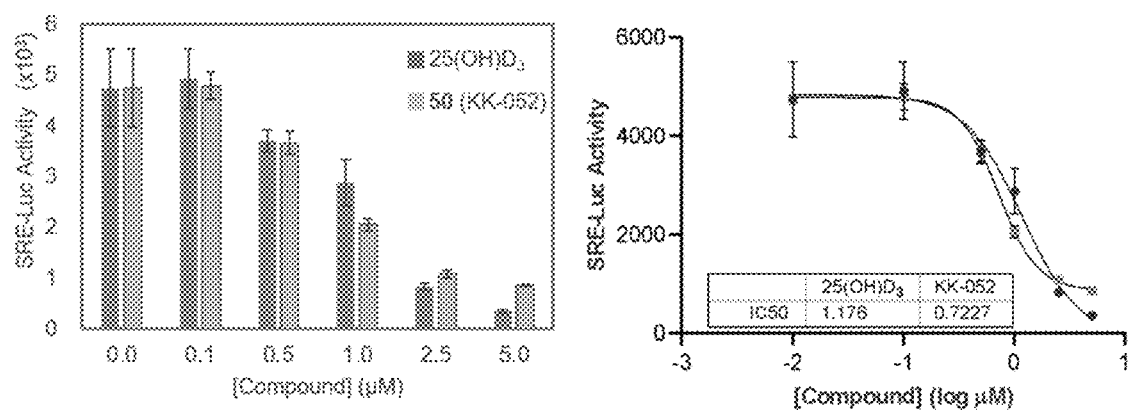
FIG. 6 shows inhibition of SREBP and SCAP by KK-052 (50): (A) Effects of 25(OH)D$_3$ and KK-052 on the ability of endogenous SREBPs to activate transcription of a luciferase reporter gene (where in the right panel, the line labeled with circles is for 25(OH)D$_3$ and the line labeled with squares is for KK-052); (B) Western blot analysis of endogenous SREBP-2 and SCAP. 25(OH)D$_3$ and KK-052 decreased the protein levels of both precursor and mature forms of SREBP-2, as well as SCAP. (CHO-K1 cells were treated with the compound in a lipid-free medium for 24 h); (C) Western blot analysis of SCAP: CHO-K1 cells expressing FLAG-tagged SCAP were treated with the compound in a lipid-free medium for 24 h and immunoblots were performed with an anti-FLAG antibody.
Figure 6:
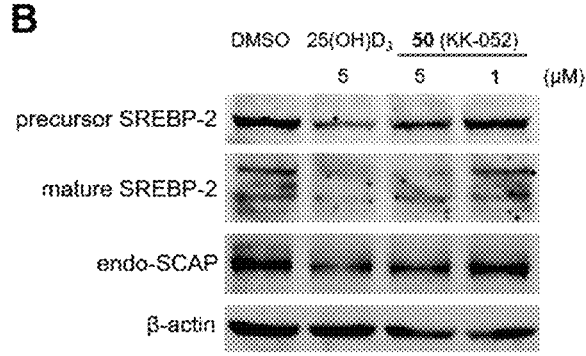
Figure 6:
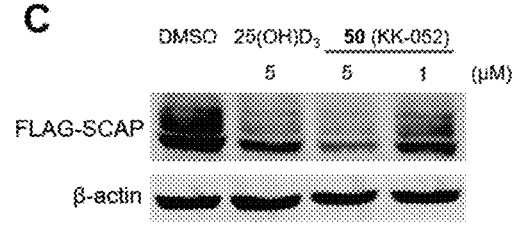

The effects of KK-052 (50) on SREBP and SCAP by gene reporter assay and Western blot analysis were verified. Similar to the results of the screening provided in FIG. 3, KK-052 inhibited the activation of the reporter gene in a concentration-dependent manner comparable to $25(OH)D_3$ (FIG. 6A, where values are mean±SD.). Non-linear regression analysis showed the sigmoidal dose-response with similar $IC_{50}$ values for both metabolites (FIG. 6A, right panel). The inhibitory activity of KK-052 was attributable to its ability in decreasing the level of endogenous both precursor and mature forms of SREBP and SCAP similar to the actions of $25(OH)D_3$ (Asano, L. et al. *Cell Chem. Biol.* 2017, 24, 207-217), although the effect was less evident at 1 μM concentration (FIG. 6B, where immunoblots were performed with an anti-SREBP-2 or anti-SCAP antibody and cells were treated with the compound in a lipid-free medium for 24 h). Western blot analysis using CHO-K1 cells expressing FLAG-tagged SCAP more clearly showed the degradation of SCAP by the vitamin D metabolites (FIG. 6C, where cells were treated with the compound in a lipid-free medium for 24 h). Overall, the results were consistent with the effects of KK-052 in vivo.

Treatment with KK-052, following the protocol in Biological Example 3, slightly but significantly decreased weight gain in ob/ob mice (FIG. 7B). Histology of the liver of vehicle-treated ob/ob mice revealed marked liver steatosis, and such conditions were attenuated by treatment with KK-052 (FIG. 7C). Moreover, hepatic triglyceride (TG) and cholesterol contents were significantly decreased in the KK-052-treated ob/ob mice compared to the vehicle-treated ob/ob mice (FIG. 7D). Importantly, the treatment with KK-052 significantly decreased serum levels of alanine aminotransferase (ALT), a marker of liver damage, as well as TG and glucose (FIG. 7E). There was no detectable difference in the serum calcium levels between KK-052- and vehicle-treated group. Taken together, KK-052 mitigates fatty liver development without inducing hypercalcemia in ob/ob mice.

Surprisingly, substitution of the A-ring of 25-hydroxyvitamin $D_3$ with a completely unnatural entity led to the discovery of VDR-silent SREBP inhibitors and to the development of KK-052 (50). KK-052 represents the first vitamin D-based SREBP inhibitor that has been demonstrated to mitigate hepatic lipid accumulation without calcemic action in mice.

INDUSTRIAL APPLICABILITY

The compound of Formula (I) or a pharmaceutically acceptable salt thereof may be useful for treating a disease such as metabolic disease including non-alcoholic steatohepatitis (NASH), a liver disease including fatty liver, diabetes, cancer, obesity, and cardiovascular disease.

What is claimed:
1. A compound of formula (I):

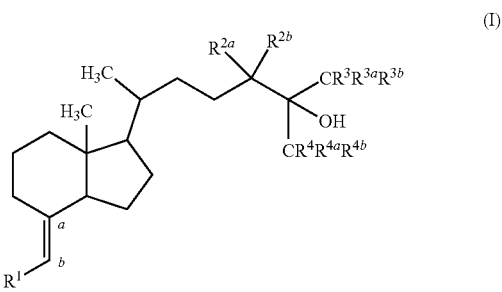

or a stereoisomer, mixture of stereoisomers, and/or a pharmaceutically acceptable salt thereof,
wherein
the double bond from a to b is in the E-configuration or Z-configuration;

$R^1$ is hydrogen;

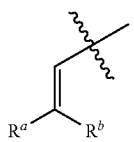

where $R^a$ and $R^b$ together with the carbon to which they are attached form an unsubstituted $C_5$-$C_7$-cycloalkyl group; —$CH_2$—S-(heteroaryl); —$CH_2$-(1,3-dioxo-isoindolin-2-yl);

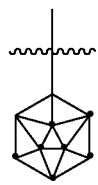

(ortho-carboranyl); —$CH_2$—NH-(phenyl); or

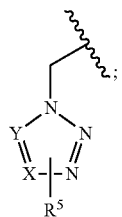

$R^{2a}$, $R^{2b}$, $R^3$, $R^{3a}$, $R^{3b}$, $R^4$, $R^{4a}$, and $R^{4b}$ are independently selected from hydrogen and halo;

one of X and Y is $CR^5$ and the other is CH; or one of X and Y is $CR^5$ and the other is N;

$R^5$ is hydrogen; $C_1$-$C_6$-alkyl; hydroxy-$C_1$-$C_6$-alkyl; aryl optionally substituted with 1, 2, or 3 $R^{5a}$ groups; or 5- or 6-membered heteroaryl optionally substituted with 1, 2, or 3 $R^{5a}$ groups;

each $R^{5a}$ is independently hydrogen, alkyl, haloalkyl, or halo; and wherein each phenyl and heteroaryl group are independently optionally substituted with 1, 2, 3, 4, or 5 groups independently selected from the group consisting of halogen, halo-$C_{1-4}$ alkyl, —S-(halo-$C_{1-4}$ alkyl), $C_{1-4}$ alkoxy, halo-$C_{1-4}$ alkoxy, nitro, cyano, and $C_{1-4}$ alkoxycarbonyl; and provided that the compound is not

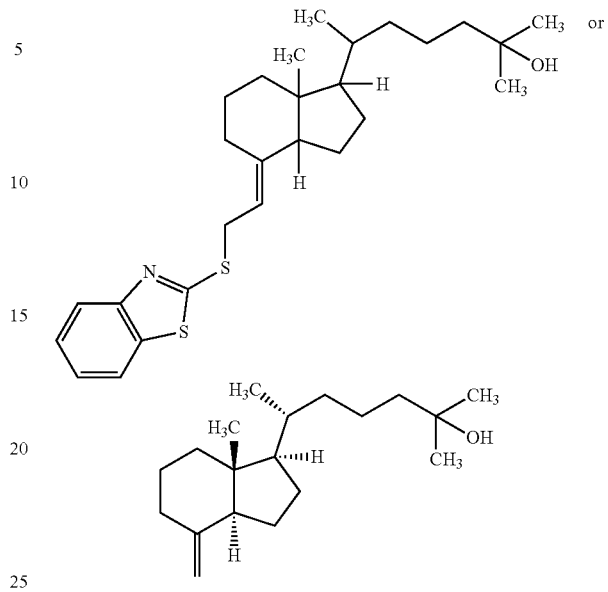

or a stereoisomer, mixture of stereoisomers, and/or a pharmaceutically acceptable salt thereof.

2. The compound of claim 1, or a stereoisomer, mixture of stereoisomers, and/or a pharmaceutically acceptable salt thereof, wherein the double bond from a to b is in the E-configuration or Z-configuration;

$R^1$ is hydrogen; $R^1$ is

where $R^a$ and $R^b$ together with the carbon to which they are attached form an unsubstituted $C_5$-$C_7$-cycloalkyl group; $R^1$ is —$CH_2$—S-(heteroaryl) where the heteroaryl is optionally substituted with 1, 2, 3, 4, or 5 groups independently selected from the group consisting of halogen, halo-$C_{1-4}$ alkyl, —S-(halo-$C_{1-4}$ alkyl), $C_{1-4}$ alkoxy, halo-$C_{1-4}$ alkoxy, nitro, cyano, and $C_{1-4}$ alkoxycarbonyl; $R^1$ is —$CH_2$-(1,3-dioxo-isoindolin-2-yl); $R^1$ is

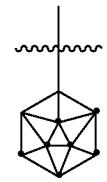

(ortho-carboranyl); $R^1$ is —$CH_2$—NH-(phenyl) where the phenyl is optionally substituted with 1, 2, 3, 4, or 5 groups independently selected from the group consisting of halogen, halo-$C_{1-4}$ alkyl, —S-(halo-$C_{1-4}$ alkyl), $C_{1-4}$ alkoxy, halo-$C_{1-4}$ alkoxy, nitro, cyano, and $C_{1-4}$ alkoxycarbonyl; $R^1$ is or

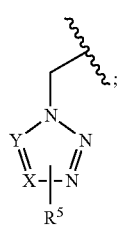

$R^{2a}$, $R^{2b}$, $R^3$, $R^{3a}$, $R^{3b}$, $R^4$, $R^{4a}$, and $R^{4b}$ are independently selected from hydrogen and halo;

one of X and Y is $CR^5$ and the other is CH; or one of X and Y is $CR^5$ and the other is N;

$R^5$ is hydrogen; $C_1$-$C_6$-alkyl; hydroxy-$C_1$-$C_6$-alkyl; aryl optionally substituted with 1, 2, or 3 $R^{5a}$ groups; or 5- or 6-membered heteroaryl optionally substituted with 1, 2, or 3 $R^{5a}$ groups; and each $R^{5a}$ is independently hydrogen, alkyl, haloalkyl, or halo; and provided that the compound is not

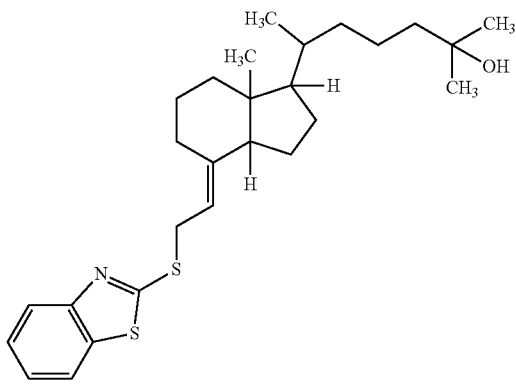 [SMILES: CC(CCCC(C)(C)O)C1CCC2/C(=C/CSc3nc4ccccc4s3)CCCC21C]

or a stereoisomer, mixture of stereoisomers, and/or a pharmaceutically acceptable salt thereof.

3. The compound of claim 1, wherein one $R^{5a}$ is hydrogen and the other $R^{5a}$ are independently hydrogen, alkyl, haloalkyl, or halo; or a stereoisomer, mixture of stereoisomers, and/or a pharmaceutically acceptable salt thereof.

4. The compound of claim 1, wherein two $R^{5a}$ are each hydrogen and the third $R^{5a}$ is alkyl, haloalkyl, or halo; or a stereoisomer, mixture of stereoisomers, and/or a pharmaceutically acceptable salt thereof.

5. The compound of claim 1, wherein two $R^{5a}$ are each hydrogen and the third $R^{5a}$ is halo; or a stereoisomer, mixture of stereoisomers, and/or a pharmaceutically acceptable salt thereof.

6. The compound of claim 1, wherein one $R^{5a}$ is hydrogen and the other two $R^{5a}$ are independently halo; or a stereoisomer, mixture of stereoisomers, and/or a pharmaceutically acceptable salt thereof.

7. The compound of claim 1, wherein the compound according to Formula (I) is according to Formula (Ia):

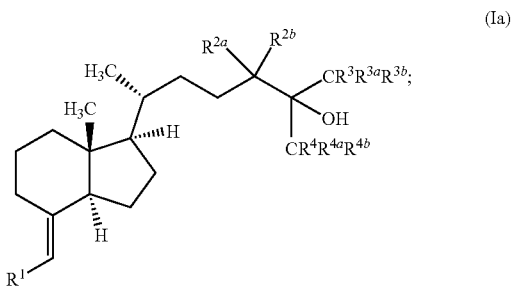

(Ia)

or a stereoisomer, mixture of stereoisomers, and/or a pharmaceutically acceptable salt thereof.

8. The compound of claim 1, wherein $R^1$ is

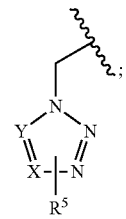

or a stereoisomer, mixture of stereoisomers, and/or a pharmaceutically acceptable salt thereof.

9. The compound of claim 8, wherein one of X and Y is $CR^5$ and the other is CH; or a stereoisomer, mixture of stereoisomers, and/or a pharmaceutically acceptable salt thereof.

10. The compound of claim 8, wherein one of X and Y is $CR^5$ and the other is N; or a stereoisomer, mixture of stereoisomers, and/or a pharmaceutically acceptable salt thereof.

11. The compound of claim 8, wherein $R^5$ is phenyl optionally substituted with 1, 2, or 3 $R^{5a}$ groups; or a stereoisomer, mixture of stereoisomers, and/or a pharmaceutically acceptable salt thereof.

12. The compound of claim 8, wherein $R^5$ is 5-membered heteroaryl optionally substituted with 1, 2, or 3 $R^{5a}$ groups; or a stereoisomer, mixture of stereoisomers, and/or a pharmaceutically acceptable salt thereof.

13. The compound of claim 1, wherein $R^{2a}$ and $R^{2b}$ are independently hydrogen or fluoro; or a stereoisomer, mixture of stereoisomers, and/or a pharmaceutically acceptable salt thereof.

14. The compound of claim 1, wherein $R^{2a}$ and $R^{2b}$ are each fluoro; or a stereoisomer, mixture of stereoisomers, and/or a pharmaceutically acceptable salt thereof.

15. The compound of claim 1, wherein $R^3$, $R^{3a}$, $R^{3b}$, $R^4$, $R^{4a}$, and $R^{4b}$ are each hydrogen; or a stereoisomer, mixture of stereoisomers, and/or a pharmaceutically acceptable salt thereof.

16. The compound of claim 1, wherein $R^3$, $R^{3a}$, $R^{3b}$, $R^4$, $R^{4a}$, and $R^{4b}$ are each fluoro; or a stereoisomer, mixture of stereoisomers, and/or a pharmaceutically acceptable salt thereof.

17. The compound of claim 7, wherein the bond from a to b is in the E-configuration; or a stereoisomer, mixture of stereoisomers, and/or a pharmaceutically acceptable salt thereof.

18. The compound of claim 1, selected from the group consisting of:
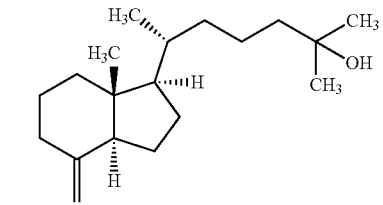
10
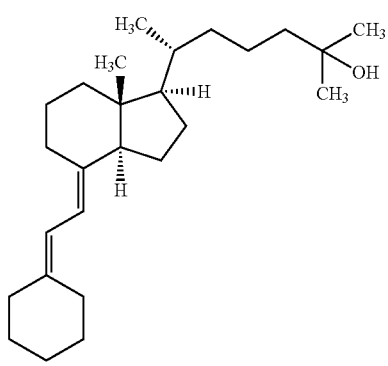
14
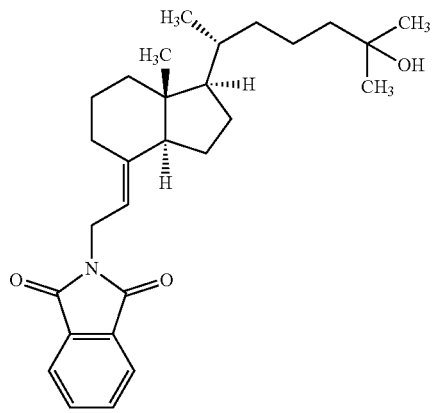
16
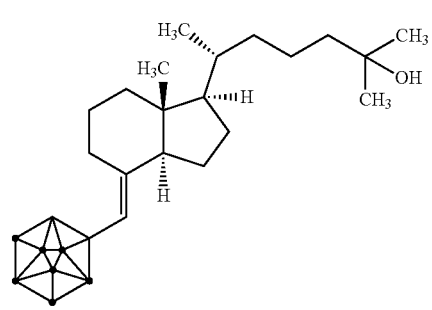
17
-continued
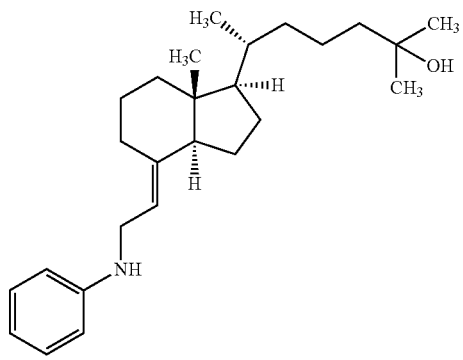
18
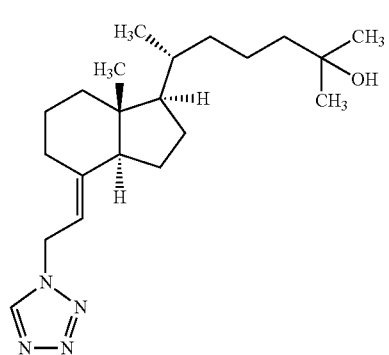
21
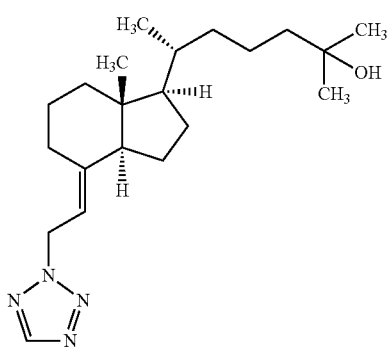
22
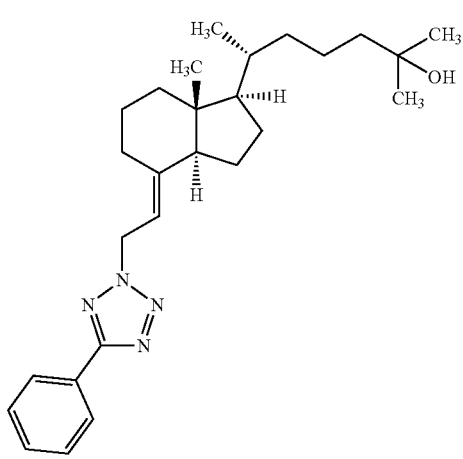
23

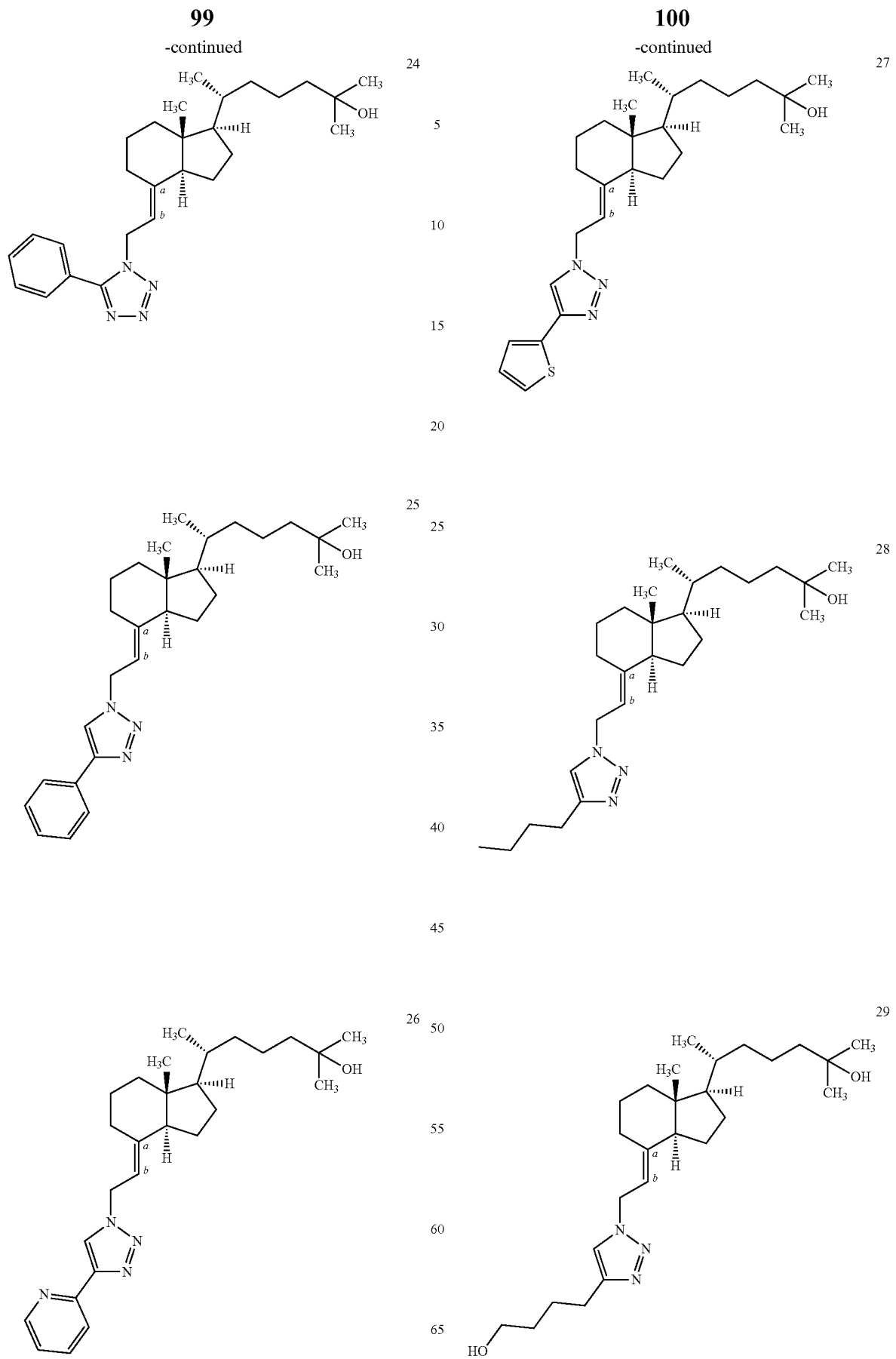

101
-continued
38
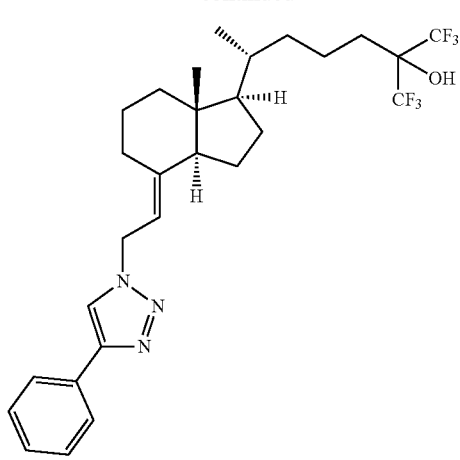
39
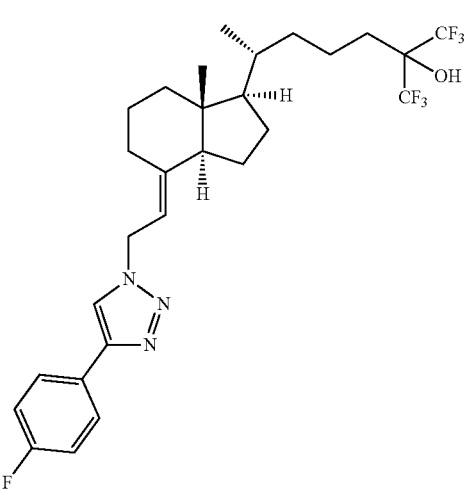
40
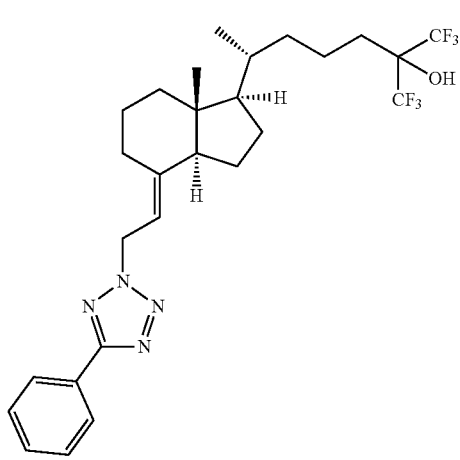
102
-continued
41
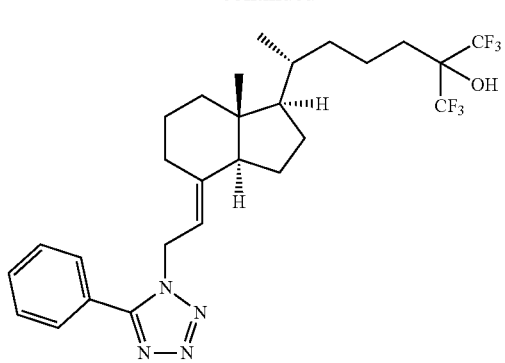
46
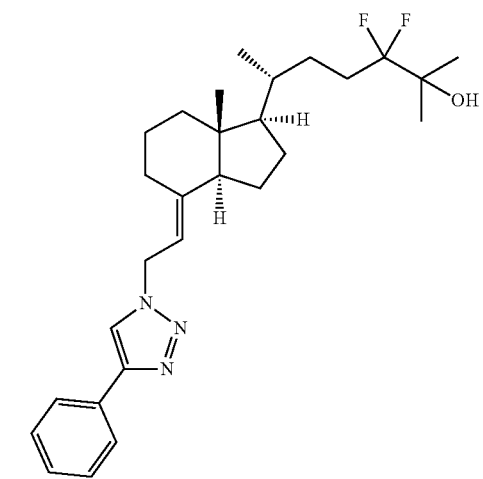
47
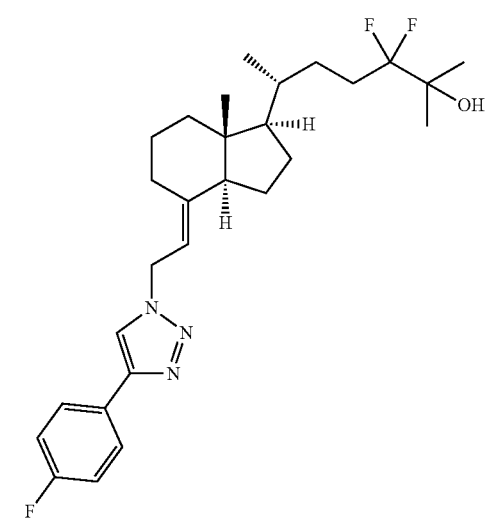

48
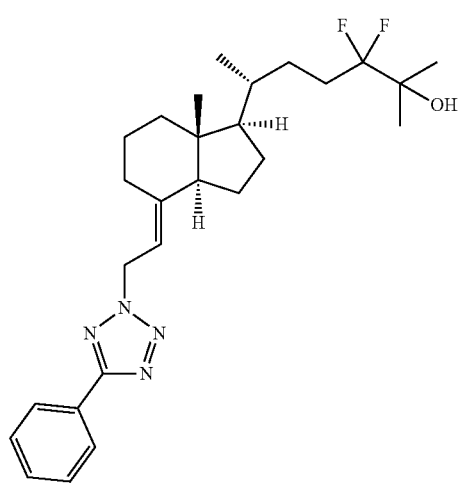
49
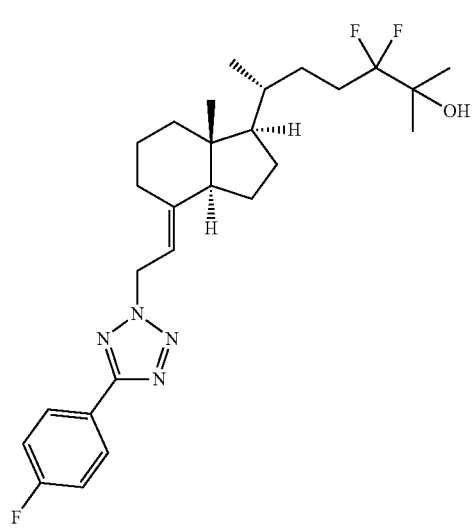
50
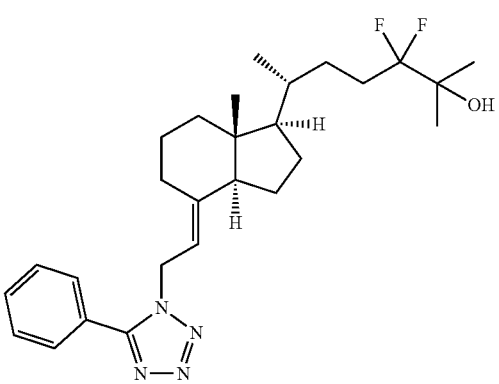
51
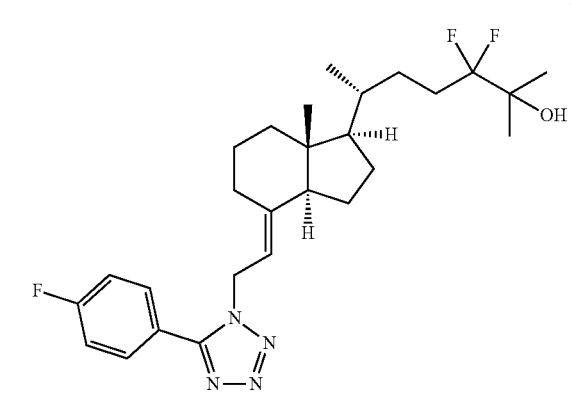
52
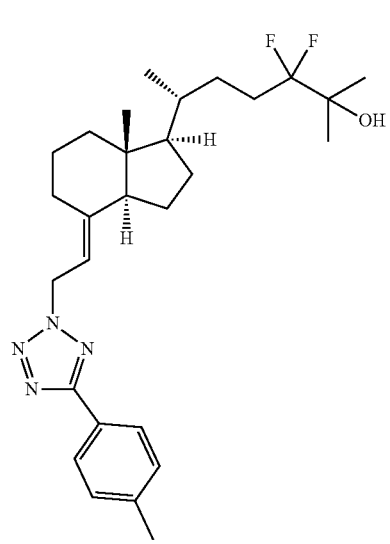
53
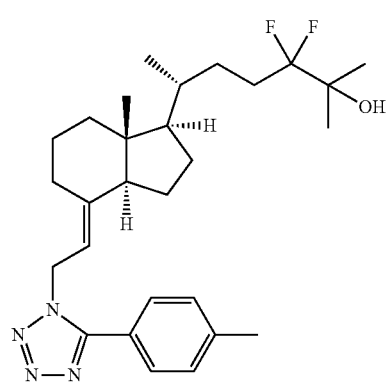

54
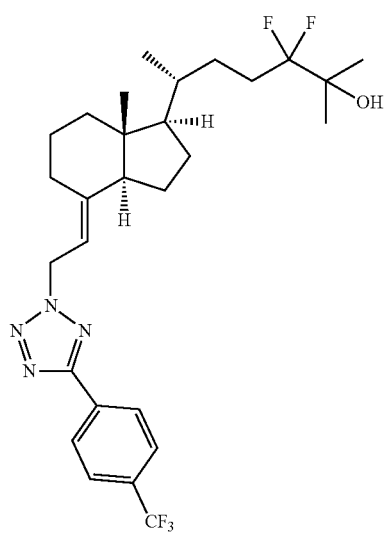
55
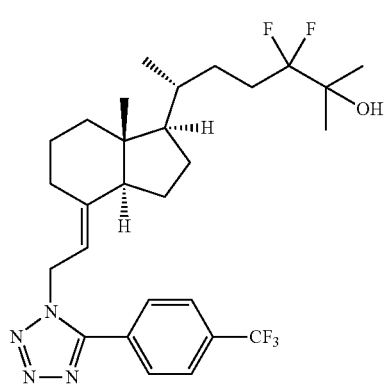
56
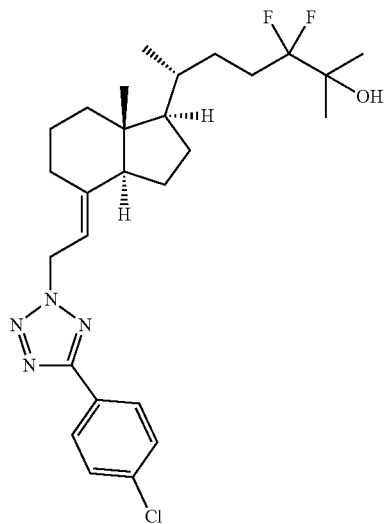
57
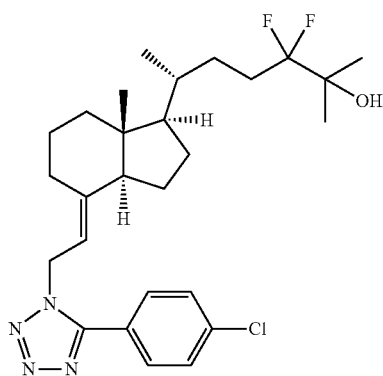
58
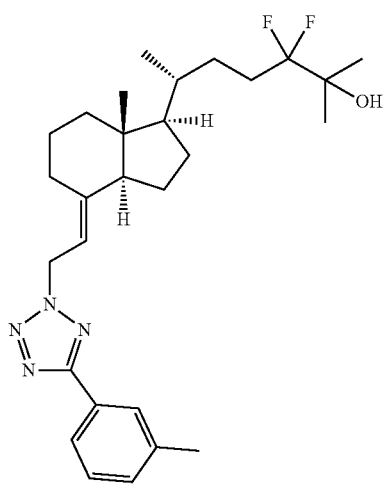
59
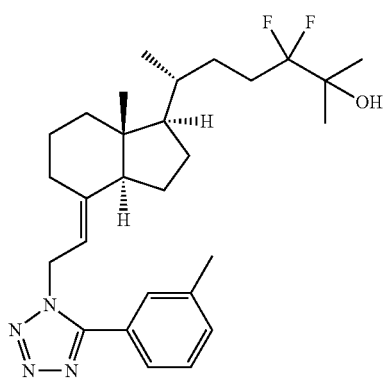

60
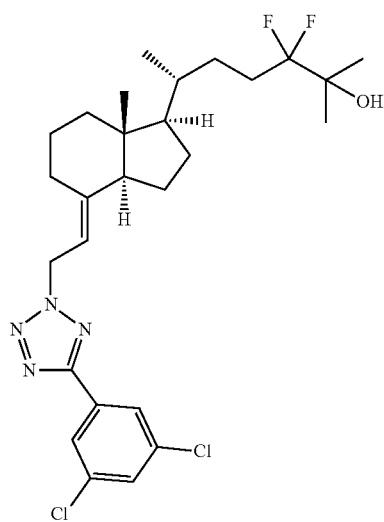
61
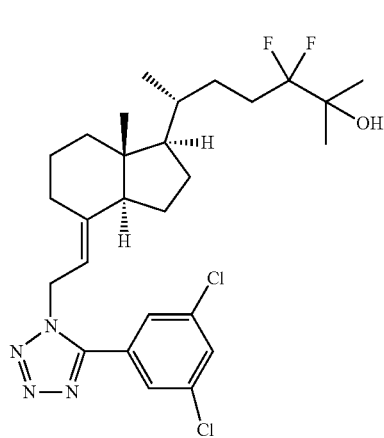
62
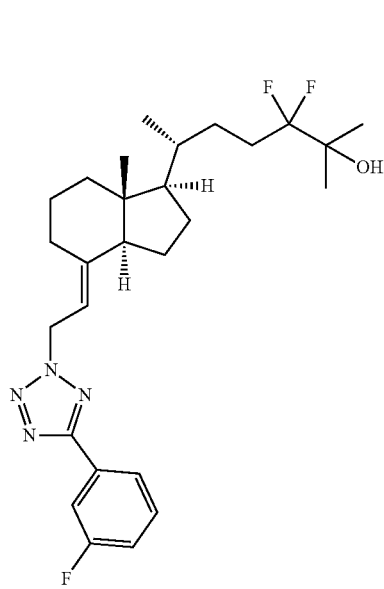
63
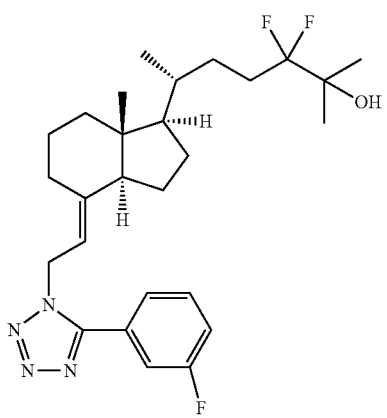
64
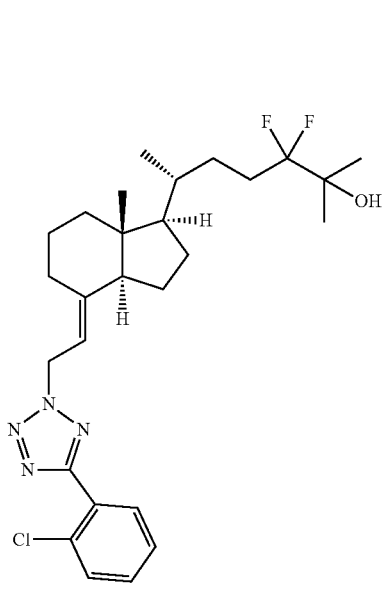

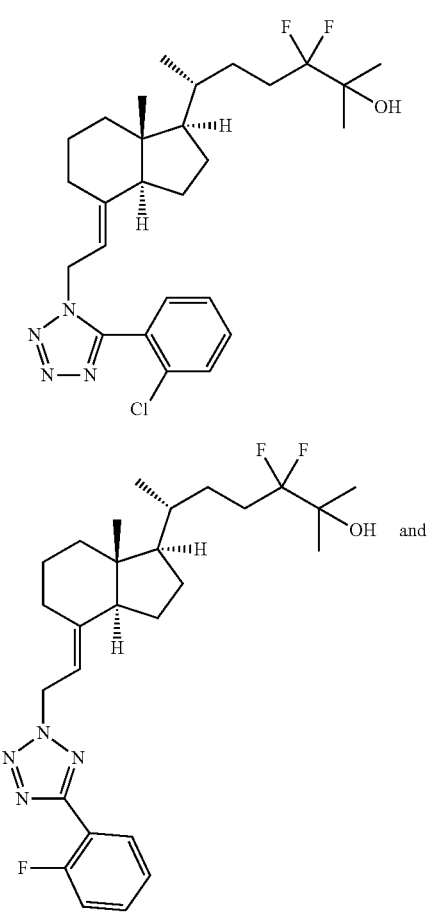

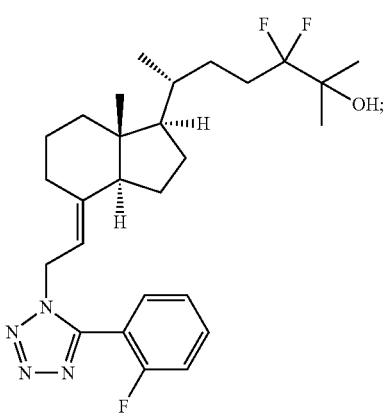

or a pharmaceutically acceptable salt thereof.

19. A pharmaceutical composition comprising a therapeutically effective amount of a compound of claim 1, or a stereoisomer, mixture of stereoisomers, and/or a pharmaceutically acceptable salt thereof; and a pharmaceutically acceptable carrier.

20. A method for inhibiting SREBPs in a subject, comprising a step of administering to the subject in need thereof a therapeutically effective amount of the compound of claim 1 or a pharmaceutically acceptable salt thereof.

21. A method for treating metabolic disease, a liver disease, obesity, diabetes, cardiovascular disease or hyperlipidemia in a subject, comprising a step of administering to the subject in need thereof a therapeutically effective amount of the compound of claim 1 or a pharmaceutically acceptable salt thereof.

\* \* \* \* \*